(12) United States Patent
Lewis et al.

(10) Patent No.: US 9,596,823 B2
(45) Date of Patent: Mar. 21, 2017

(54) TOBACCO INBRED AND HYBRID PLANTS AND TOBACCO PRODUCTS MADE THEREOF

(71) Applicant: North Carolina State University, Raleigh, NC (US)

(72) Inventors: Ramsey S. Lewis, Apex, NC (US); Ralph E. Dewey, Apex, NC (US)

(73) Assignee: North Carolina State University, Raleigh, NC (US)

( * ) Notice: Subject to any disclaimer, the term of this patent is extended or adjusted under 35 U.S.C. 154(b) by 86 days.

(21) Appl. No.: 14/636,876

(22) Filed: Mar. 3, 2015

(65) Prior Publication Data

US 2015/0245584 A1    Sep. 3, 2015

Related U.S. Application Data

(60) Provisional application No. 61/978,253, filed on Apr. 11, 2014, provisional application No. 61/978,267, filed on Apr. 11, 2014, provisional application No. 61/978,305, filed on Apr. 11, 2014, provisional application No. 61/978,312, filed on Apr. 11, 2014, provisional application No. 61/946,988, filed on Mar. 3, 2014, provisional application No. 61/946,983, filed on Mar. 3, 2014, provisional application No. 61/946,981, filed on Mar. 3, 2014, provisional application No. 61/946,978, filed on Mar. 3, 2014.

(51) Int. Cl.
| | |
|---|---|
| *A01H 5/12* | (2006.01) |
| *A24B 13/00* | (2006.01) |
| *A24D 3/04* | (2006.01) |
| *A24D 3/00* | (2006.01) |
| *A24B 13/02* | (2006.01) |
| *A24D 1/00* | (2006.01) |
| *C12N 9/10* | (2006.01) |
| *C12N 15/82* | (2006.01) |

(52) U.S. Cl.
CPC ............... *A01H 5/12* (2013.01); *A24B 13/00* (2013.01); *A24B 13/02* (2013.01); *A24D 1/00* (2013.01); *A24D 3/00* (2013.01); *A24D 3/043* (2013.01); *C12N 9/1007* (2013.01); *C12N 15/8243* (2013.01)

(58) Field of Classification Search
None
See application file for complete search history.

(56) References Cited

U.S. PATENT DOCUMENTS

| | | | |
|---|---|---|---|
| 4,693,976 A | 9/1987 | Schilperoort et al. |
| 4,732,856 A | 3/1988 | Federoff |
| 4,762,785 A | 8/1988 | Comai |
| 4,801,540 A | 1/1989 | Hiatt et al. |
| 4,940,838 A | 7/1990 | Schilperoort et al. |
| 4,945,050 A | 7/1990 | Sanford et al. |
| 5,004,863 A | 4/1991 | Umbeck |
| 5,013,658 A | 5/1991 | Dooner et al. |
| 5,034,323 A | 7/1991 | Jorgensen et al. |
| 5,104,310 A | 4/1992 | Saltin |
| 5,107,065 A | 4/1992 | Shewmaker et al. |
| 5,141,131 A | 8/1992 | Miller et al. |
| 5,149,645 A | 9/1992 | Hoekema et al. |
| 5,159,135 A | 10/1992 | Umbeck |
| 5,177,010 A | 1/1993 | Goldman et al. |
| 5,231,019 A | 7/1993 | Paszkowski et al. |
| 5,302,523 A | 4/1994 | Coffee et al. |
| 5,352,605 A | 10/1994 | Fraley et al. |
| 5,378,619 A | 1/1995 | Rogers |
| 5,384,253 A | 1/1995 | Krzyzek et al. |
| 5,463,174 A | 10/1995 | Moloney et al. |
| 5,464,763 A | 11/1995 | Schilperoort et al. |
| 5,464,765 A | 11/1995 | Coffee et al. |
| 5,469,976 A | 11/1995 | Burchell |
| 5,472,869 A | 12/1995 | Krzyzek et al. |
| 5,583,021 A | 12/1996 | Dougherty et al. |
| 5,595,733 A | 1/1997 | Carswell et al. |
| 5,614,399 A | 3/1997 | Quail et al. |
| 5,641,664 A | 6/1997 | D'Halluin et al. |
| 5,668,295 A | 9/1997 | Wahab et al. |
| 5,679,558 A | 10/1997 | Gobel et al. |
| 5,684,241 A | 11/1997 | Nakatani et al. |
| 5,712,135 A | 1/1998 | D'Halluin et al. |
| 5,713,376 A | 2/1998 | Berger |

(Continued)

FOREIGN PATENT DOCUMENTS

| | | |
|---|---|---|
| EP | 0 120 516 A3 | 10/1984 |
| EP | 0 267 159 A3 | 5/1988 |

(Continued)

OTHER PUBLICATIONS

International Preliminary Report on Patentability corresponding to International Application No. PCT/US2014/019381; Issued Sep. 8, 2015.
Invitation to Pay Additional Fees, PCT/US2015/018387, mailed Jun. 1, 2015, 8 pages.
Notification of Transmittal of the International Search Report and the Written Opinion of the International Searching Authority, or the Declaration, PCT/US2015/018393, Jun. 2, 2015, 11 pages.

(Continued)

*Primary Examiner* — Russell Kallis

(74) *Attorney, Agent, or Firm* — Myers Bigel, P.A.

(57) ABSTRACT

The present disclosure provides tobacco inbred plants Banket A1 SRC, CMS Banket A1 SRC, NC 2000 SRC, CMS NC 2000 SRC, NC 2002 SRC, CMS NC 2002 SRC, Burley 21 SRC, and CMS Burley 21 SRC. The present disclosure also provides parts of such plants and cured tobacco and tobacco products made from those parts. The present disclosure also includes progenies of the provided plants including hybrids.

17 Claims, No Drawings

(56) References Cited

U.S. PATENT DOCUMENTS

| | | | |
|---|---|---|---|
| 5,766,900 | A | 6/1998 | Shillito et al. |
| 5,929,304 | A | 7/1999 | Radin et al. |
| 6,002,070 | A | 12/1999 | D'Halluin et al. |
| 6,074,877 | A | 6/2000 | D'Halluin et al. |
| 6,907,887 | B2 | 6/2005 | Conkling |
| 6,953,040 | B2 | 10/2005 | Atchley et al. |
| 6,965,062 | B2 | 11/2005 | Rufty |
| 7,032,601 | B2 | 4/2006 | Atchley et al. |
| 7,700,834 | B2 | 4/2010 | Xu et al. |
| 7,700,851 | B2 | 4/2010 | Xu |
| 7,812,227 | B2 | 10/2010 | Xu |
| 7,855,318 | B2 | 12/2010 | Xu |
| 7,884,263 | B2 | 2/2011 | Dewey et al. |
| 8,058,504 | B2 | 11/2011 | Xu |
| 8,124,851 | B2 | 2/2012 | Dewey et al. |
| 8,319,011 | B2 | 11/2012 | Xu et al. |
| 9,247,706 | B2 * | 2/2016 | Dewey .................... A01H 5/12 |
| 2002/0042934 | A1 | 4/2002 | Staub et al. |
| 2004/0103449 | A1 | 5/2004 | Xu |
| 2004/0111759 | A1 | 6/2004 | Xu |
| 2004/0117869 | A1 | 6/2004 | Xu |
| 2004/0162420 | A1 | 8/2004 | Xu |
| 2005/0132444 | A1 | 6/2005 | Xu |
| 2005/0160493 | A9 | 7/2005 | Ratcliffe et al. |
| 2005/0178398 | A1 | 8/2005 | Breslin et al. |
| 2005/0223442 | A1 | 10/2005 | Xu |
| 2005/0244521 | A1 | 11/2005 | Strickland et al. |
| 2006/0037096 | A1 | 2/2006 | Xu |
| 2006/0037623 | A1 | 2/2006 | Lawrence |
| 2006/0041949 | A1 | 2/2006 | Xu |
| 2006/0157072 | A1 | 7/2006 | Albino et al. |
| 2006/0185686 | A1 | 8/2006 | Lawrence |
| 2006/0191548 | A1 | 8/2006 | Strickland et al. |
| 2007/0149408 | A1 | 6/2007 | Thomas et al. |
| 2007/0199097 | A1 | 8/2007 | Xu et al. |
| 2007/0292871 | A1 | 12/2007 | Xu |
| 2008/0076126 | A1 | 3/2008 | Xu |
| 2008/0202541 | A1 | 8/2008 | Dewey et al. |
| 2008/0245377 | A1 | 10/2008 | Marshall et al. |
| 2009/0119788 | A1 | 5/2009 | Mallmann et al. |
| 2009/0205072 | A1 | 8/2009 | Dewey et al. |
| 2010/0218270 | A1 | 8/2010 | Xu et al. |
| 2010/0235938 | A1 | 9/2010 | Xu et al. |
| 2010/0235945 | A1 | 9/2010 | Xu et al. |
| 2010/0235952 | A1 | 9/2010 | Xu et al. |
| 2011/0048437 | A1 | 3/2011 | Xu |
| 2011/0078817 | A1 | 3/2011 | Xu |
| 2011/0174322 | A1 | 7/2011 | Dewey et al. |
| 2011/0263328 | A1 | 10/2011 | Yamashita et al. |
| 2012/0117933 | A1 | 5/2012 | Dewey et al. |
| 2012/0118308 | A1 | 5/2012 | Dewey et al. |
| 2012/0216822 | A1 | 8/2012 | Lewis et al. |
| 2012/0222689 | A1 | 9/2012 | Xu et al. |
| 2014/0196730 | A1 | 7/2014 | Lewis et al. |
| 2014/0251353 | A1 | 9/2014 | Lewis et al. |

FOREIGN PATENT DOCUMENTS

| | | | |
|---|---|---|---|
| EP | 0 292 435 B1 | 11/1988 | |
| EP | 0 320 500 B1 | 6/1989 | |
| EP | 0 116 718 B1 | 5/1990 | |
| EP | 0 159 418 B1 | 5/1990 | |
| EP | 0 176 112 B1 | 5/1990 | |
| EP | 0 131 624 B1 | 9/1992 | |
| EP | 0 627 752 B1 | 7/1997 | |
| EP | 1 033 405 A3 | 9/2000 | |
| EP | 0 290 799 B9 | 11/2003 | |
| WO | WO 87/06614 A1 | 11/1987 | |
| WO | WO 92/09696 A1 | 6/1992 | |
| WO | WO 93/21335 A2 | 10/1993 | |
| WO | WO 94/01930 A1 | 1/1994 | |
| WO | WO 00/67558 A1 | 11/2000 | |
| WO | WO 02/072758 A2 | 9/2002 | |
| WO | WO 02/100199 A2 | 12/2002 | |
| WO | WO 03/078577 A2 | 9/2003 | |
| WO | WO 2004/035745 A2 | 4/2004 | |
| WO | WO 2005/038018 A2 | 4/2005 | |
| WO | WO 2005/038033 A2 | 4/2005 | |
| WO | WO 2005/046363 A2 | 5/2005 | |
| WO | WO 2005/111217 A2 | 11/2005 | |
| WO | WO 2005/116199 A2 | 12/2005 | |
| WO | WO 2006/022784 A1 | 3/2006 | |
| WO | WO 2006/091194 A1 | 8/2006 | |
| WO | WO 2006/120570 A2 | 11/2006 | |
| WO | WO 2008/070274 A2 | 6/2008 | |
| WO | WO 2008/076802 A2 | 6/2008 | |
| WO | WO 2009/064771 A2 | 5/2009 | |
| WO | WO 2011/088180 | * 7/2011 | ............... A01H 5/12 |
| WO | WO 2011/088180 A1 | 7/2011 | |
| WO | WO 2012/118779 A1 | 9/2012 | |
| WO | WO 2014/110363 | 7/2014 | |

OTHER PUBLICATIONS

U.S. Appl. No. 14/636,876, filed Mar. 3, 2015.
U.S. Appl. No. 14/636,894, filed Mar. 3, 2015.
U.S. Appl. No. 14/636,565, filed Mar. 3, 2015.
U.S. Appl. No. 60/337,684, filed Nov. 13, 2001, Xu.
U.S. Appl. No. 60/347,444, filed Jan. 11, 2002, Xu.
U.S. Appl. No. 60/363,684, filed Mar. 12, 2002, Xu.
U.S. Appl. No. 60/418,933, filed Oct. 16, 2002, Xu.
U.S. Appl. No. 60/485,368, filed Jul. 8, 2003, Xu.
U.S. Appl. No. 60/503,989, filed Sep. 18, 2003, Xu.
U.S. Appl. No. 60/566,235, filed Apr. 29, 2004, Xu.
U.S. Appl. No. 60/607,357, filed Sep. 3, 2004, Xu.
U.S. Appl. No. 60/646,764, filed Jan. 25, 2005, Xu.
U.S. Appl. No. 60/665,097, filed Mar. 24, 2005, Xu.
U.S. Appl. No. 60/665,451, filed Mar. 24, 2005, Xu.
Julio, E. et al. Molecular Breeding (2008), vol. 21, pp. 369-381.
Nikova, V. et al. Euphytica (1997), vol. 94, pp. 375-378.
Notification of Transmittal of the International Search Report and the Written Opinion of the International Searching Authority, or the Declaration in correspondence PCT Application No. PCT/US2012/026864 mailed May 4, 2012 (13 pages).
Gavilano et al., "Genetic Engineering of *Nicotiana tabacum* for Reduced Nornicotine Content" *J. Agric. Food Chem.* (2006) 54:9071-9078.
Julio et al., "Reducing the content of nornicotine in tobacco via targeted mutation breeding," *Mol. Breeding* (2008) 21:369-381.
Adams et al., "Genes duplicated by polyploidy show unequal contributions to the transcriptome and organ-specific reciprocal silencing,"*PNAS*, 100(8):4649-4654 (2003).
Allen et al., "RNAi-mediated replacement of morphine with the nonnarcotic alkaloid reticuline in opium poppy," *Nature Biotechnology*, 22(12):1559-1566 (2004).
Alonso et al., "A Hox gene mutation that triggers nonsense-mediated RNA decay and affects alternative splicing during *Drosophila* development," *Nucleic Acids Research*, 31 (14):3873-3880 (2003).
Arciga-Reyes et al., "UPF1 is required for nonsense-mediated mRNA decay (NMD) and RNAi in *Arabidopsis*" *The Plant Journal*, 47:480-489 (2006).
Arndt et al., "Colocalization of antisense RNAs and ribozymes with their target mRNAs," *Genome*, 40:785-797 (1997).
ARS-GRIN: PI 551280, "*Nicotiana tabacum*," http://www.ars-grin.gov/cgi-bin/npgs/acc/display.pl?1446216, accessed Feb. 2009).
Bak et al., "Transgenic Tobacco and *Arabidopsis* Plants Expressing the Two Multifunctional Sorghum Cytochrome P450 Enzymes, CYP79A1 and CYP71E1, Are Cyanogenic and Accumulate Metabolites Derived from Intermediates in Dhurrin Biosynthesis," *Plant Physiol.*, 123:1437-1448 (2000).
Bartoszewski et al., "Cloning of a Wound Inducible *Lycopersicon esculentum* Cytochrome P450 Gene and Lack of Regeneration of Transgenic Plants with Sense or Antisense Constructs," *J. AmSoc. Hort. Sci*, 127(4):535-539 (2002).
Baseggio et al., "Size and genomic location of the pMGA multigene family of *Mycoplasma gallisepticum*," *Microbiology*, 142:1429-1435 (1996).

(56) References Cited

OTHER PUBLICATIONS

Batard et al., "Increasing Expression of P450 and P450-Reductase Proteins from Monocots in Heterologous Systems," *Arch. Biochem. Biophys.*, 379:161-169 (2000).

Baulcombe, "Fast Forward Genetics Based on Virus-Induced Gene Silencing," *Current Opinion in Plant Biology*, 2:109-113 (1999).

Bolitho et al., "Antisense apple ACC-oxidase RNA reduces ethylene production in transgenic tomato fruit," *Plant Science*, 122:91-99 (1997).

Bosher et al., "RNA interference: genetic wand and genetic watchdog," *Nat. Cell Biol.*, 2:E31-E36 (2000).

Bosl et al., "The role of noise and positive feedback in the onset of autosomal dominant diseases," *BMC Systems Biology*,4:1-15 (2010).

Boyette et al., "Results of year 2000 TSNA sampling program in flue-cured tobacco," *Recent Advances in Tobacco Science*, 27:17-22 (2001).

Branch, "A good antisense molecule is hard to tlnd," *TIES*, 23:45-50 (1998).

Brignetti et al., "Viral pathogenicity determinants are suppressors of transgene silencing in *Nicotiana benthamiana*," *EMBO J.*, 17(22):6739-6746 (1998).

Burns et al., "Large-scale analysis of gene expression, protein localization, and gene disruption in *Saccharomyces cerevisiae*," *Genes Dev.*, 8:1087-1105 (1994).

Burton et al., Changes in Chemical Composition of Burley Tobacco During Senescence and Curing. 2. Acylated Pyridine Alkaloids, *American Chemical Society*, pp. 579-583 (1988).

Burton et al., "Distribution of Tobacco Constituents in Tobacco Leaf Tissue. 1. Tobacco-Specific Nitrosamines, Nitrate, Nitrite, and Alkaloids," *J. Agric. Food Chem.*, 40:1050-1055 (1992).

Burton et al., "Changes in Chemical Composition of Burley Tobacco during Senescence and Curing. 2. Acylated Pyridine Alkaloids," *J .Agric. Food Chem.*, 38(3):579-584 (1998).

Bush et al., "Formation of tobacco-specific nitrosamines in air-cured tobacco," *Rec. Adv. Tob. Sci*, 27:23-46 (2001).

Byers et al., "Killing the messenger: new insights into nonsense-mediated mRNA decay" *The Journal of Clinical Investigation*, 109(1):3-6 (2002).

Byzova et al., "Transforming petals into sepaloid organs in *Arabidopsis* and oilseed rape: implementation of the hairpin RNA-mediated gene silencing technology in an organ-specific manner," *Planta*, 218:379-387 (2004).

Callis et al., "Introns increase gene expression in cultured maize cells," *Genes and Dev.*, 1:1183-1200 (1987).

Carron et al., "Genetic modification of condensed tannin biosynthesis in *Lotus comiculatus*. 1. Heterologous antisense dihydroflavonol reductase down-regulates tannin accumulation in hairy roof cultures," *Theoretical and Applied Genetics*, 87(8): 1006-1015 (1994).

Caruthers, "Chapter 1: New Methods for Chemically Synthesizing Deoxyoligonucleotides," Methods of DNA and RNA Sequencing, Weissman (ed.), Praeger Publishers, New York, pp. 1-22 (1983).

Chai et al., "Reducing the maize amylopectin content through RNA interference manipulation," *Zhi W u Sheng Li Yu Fen Zi Sheng Wu Xue Xue Buo*, 31:625-630 (2005) (English Abstract only).

Chakrabarti et al., "Inactivation of the cytochrome P450 gene CYP82E2 by degenerative mutations was a key event in the evolution of the alkaloid profile of modem tobacco," *New Phytologist*, 175:565-574 (2007).

Chakrabarti et al., "CYP82E4-mediated nicotine to nomicotine conversion in tobacco is regulated by a senescence-specific signaling pathway," *Plant Mol. Biol.*, 66: 415-427 (2008).

Chang et al., Predicting and Testing Physical Locations of Genetically Mapped Loci on Tomato. Pachytene Chromosome, *Genetics*, 176:2131-2138 (2007).

Chao et al., "A silent mutation induces exon skipping in the phenylalanine hydroxylase gene in phenylketonuria," *Hum. Genet.*, 108:14-19 (2001).

Chappell, "Biochemistry and Molecular Biology of the Isoprenoid Biosynthetic Pathway in Plants," *Annu. Rev. Plant Physiol. Plant Mol. Biol.*, 46:521-547 (1995).

Chapple, "Molecular-Genetic Analysis of Plant Cytochrome P450-Dependent Monooxygenases," *Annu. Rev. Plant Physiol. Plant Mol. Biol.*, 49:311-343 (1998).

Chelvarajan et al., Study of Nicotine Demethylation in *Nicotiana otophora*, *J. Agric. Food Chem.*, 41:858-862 (1993).

Cheung et al., "A Floral Transmitting Tissue-Specific Glycoprotein Attracts Pollen Tubes and Stimulates Their Growth," *Cell*, 82:383-393 (1995).

Chintapakorn, et al., "Antisense-Mediated Down-Regulation of Putrescine N-Methyltransferase Activity in Transgenic *Nicotiana tabacum* L. can Lead to Elevated Levels of Anatabine at the Expense of Nicotine," *Plant Molecular Biology*, 53:87-105 (2003).

Cho et al., "Transcriptome Analysis and Physical Mapping of Barley Genes in Wheat-Barley Chromosome Addition Lines," *Genetics*, 172:1277-1285 (2006).

Chou et al., "Chromosome Rearrangements in *Arabidopsis thaliana* Generated Through Cre-lox Site Specific Recombination," Plant and Animal Genome VII Conference, Abstract No. P133, 1 page (1999).

Chuang et al., "Specific and heritable genetic interference by double-stranded RNA in *Arabidopsis thaliana*," *PNAS*, 97(9):4985-4990 (2000).

Cogoni et al., "Post-transcriptional gene silencing across kingdoms," *Curr. Opin. Genet. Dev.*, 10:638-643 (2000).

Colbert et al., "High-throughput screening for induced point mutations," *Plant Physiology*, 126:480-484 (2001).

Collier et al., "A Method for Specific Amplification and P C R Sequencing of Individual Members of Multigene Families: Application to the Study of Steroid 21-Hydroxylase Deficiency," *PCR Methods and Applications*, 1:181-186 (1992).

Colliver et al., "Differential modification of flavonoid and isoflavonoid biosynthesis with an antisense chalcone synthase construct in transgenic *Lotus comiculatus*," *Plant Mol. Biol.*, 35(4):509-522 (1997).

Crookshanks et al., "The potato tuber transcriptome: analysis of 6077 expressed sequence tags," *FEBS Lett.*, 506:123-126 (2001).

Davuluri et al., "Fruit-specific RNAi-mediated suppression of DET1 enhances carotenoid and favonoid content in tomatoes," *Nat. Biotechnol.*, 23:890-895 (2005).

Dekeyser et al., Transient Gene Expression in Intact and Organized Rice Tissues, *Plant Cell*, 2:591-602 (1990).

Dewey et al., Meeting Abstract dated Sep. 27, 2005, 1 page.

Dewey et al., Power point presentation titled "Functional characterization of the nicotine N-Demethylase gene of tobacco," Philip Morris USA, 21 pages, 2006.

Donato et al., "Fluorescence-Based Assays in Intact Cells Expressing Individual Activities for Screening Nine Cytochrome P450 (P450) Human P450 Enzymes," *Drug Metab. Dispos.*, 32(7):699-706 (2004).

D'Souza et al., "Missense and silent tau gene mutations cause frontotemporal dementia with parkinsonism-chromosome 17 type, by affecting multiple alternative RNA splicing regulatory elements" *PNAS*, 96:5598-5603 (1999).

EBI Accession AV557806, dated Jun. 16, 2000, 2 pages.

Einset, "Differential expression of antisense in regenerated tobacco plants transformed with an antisense version of a tomato ACC oxidase gene," *Plant Cell Tissue and Organ Culture*, 46(2): 137-141 (1996).

Elkind et al., "Abnormal plant development and down-regulation of phenylpropanoid biosynthesis in transgenic tobacco containing a heterologous phenylalanine ammonia-lyase gene," *PNAS*, 87(22):9057-61 (1990).

EMBL Database Report for Accession No. EU182719, Dec. 2, 2007 (XP002511576).

Escobar et al., "RNAi-mediated oncogene silencing confers resistance to crown gall tumorigenesis," *PNAS*, 98: 13437-13442 (2001).

European Search Report completed on Feb. 10, 2010, in European Application No. EP 07 86 5628, 4 pages.

European Search Report completed on Mar. 31, 2011, in European Application No. EP 10 01 5540, 8 pages.

(56) References Cited

OTHER PUBLICATIONS

Falcon-Perez et al., "Functional Domain Analysis of the Yeast ABC Transporter Ycflp by Site-directed Mutagenesis," *J. Biol. Chem.*, 274(33):23584-23590 (1999).
Fang et al., "Multiple cis regulatory elements for maximal expression of the cauliflower mosaic virus 35S promoter in transgenic plants," *Plant Cell*, 1:141-150 (1989).
Fannin et al., "Nicotine demethylation in *Nicotiana*," *Med Sci. Res.*, 20:807-808 (1992).
Faske et al., "Transgenic Tobacco Plants Expressing Pea Chloroplast Nmdh eDNA in Sense and Antisense Orientation," *Plant Physiol*, 115(2): 705-715 (1997).
Fedoroff et al., "Cloning of the bronze locus in maize by a simple and generalizable procedure using the transposable controlling element Activator (Ac)," *PNAS*, 81 :3825-3829 (1984).
Fire et al., "Potent and specific genetic interference by double-stranded RNA in *Caenorhabditis elegans*," *Nature*, 391:806-811 (1998).
Force et al., "Preservation of Duplicate Genes by Complementary, Degenerative Mutations," *Genetics*, 151:1531-1545 (1999).
Forsthoefel et al., "T-DNA Insertion Mutagenesis in *Arabidopsis*: Prospects and Perspectives," *Aust. J. Plant Physiol.*, 19:353-366 (1992).
Frank et al., "Cloning of Wound-Induced Cytochrome P450 Monooxygenases Expressed in Pea," *Plant Physiol.*, 110:1035-1046 (1996).
Freeman et al.,"Quantitative RT-PCR: Pitfalls and Potential," *BioTechniques*, 26:112-125 (1999).
Fromm et al., "An octopine synthase enhancer element directs tissue-specific expression and binds ASF-1, a factor from tobacco nuclear extracts," *Plant Cell*, 1:977-984 (1989).
Gavilano, "Isolation, Cloning and Characterization of Novel Tobacco Cytochrome P450 Genes Involved in Secondary Metabolism," Plant Biology Meeting, American Society of Plant Biologists, Abstract No. 992, 1 page (2004).
Gavilano et al. "Genetic Engineering of *Nicotiana tabacum* for Reduced Nomicotine Content" *J. Agric. Food Chem.*, 54:9071-9078 (2006).
Gavilano et al., "Functional Analysis of Nicotine Demethylase Genes Reveals Insights into the Evolution of Modem Tobacco," *J. Biol. Chem.*, 282:249-256 (2007).
Gavilano et al., "Isolation and Characterization of the Cytochrome P450 Gene CYP82E5v2 that Mediates Nicotine to Nornicotine Conversion in the Green Leaves of Tobacco," *Plant Cell Physiol.*, 48(11):1567-1574 (2007).
GenBank Accession No. CAA64635, dated Sep. 12, 1996, 2 pages.
GenBank Accession No. BAA35080, dated Sep. 26, 2000, 2 pages.
GenBank Accession No. AAK62347, dated Jun. 14, 2001, 2 pages.
GenBank Accession No. AAK62343, dated Feb. 11, 2002, 2 pages.
GenBank Accession No. AAK62346, dated Feb. 11, 2002, 2 pages.
GenBank Accession No. AEK08729 dated Feb. 23, 2005, 2 pages.
GenBank Accession No. AAK62342, Sep. 20, 2005, 2 pages.
GenBank Accession No. ABA07804, dated Oct. 13, 2005, 2 pages.
GenBank Accession No. ABA07805, dated Oct. 13, 2005, 2 pages.
GenBank Accession No. ABA07807, dated Oct. 13, 2005, 2 pages.
GenBank Accession No. DQ131885, dated Oct. 13, 2005, 2 pages.
GenBank Accession No. DQ131886, dated Oct. 13, 2005, 2 pages.
GenBank Accession No. DQ131888, dated Oct. 13, 2005, 2 pages.
GenBank Accession No. DQ219341, dated Oct. 1, 2006, 2 pages.
GenBank Accession No. DQ219342, dated Oct. 1, 2006, 2 pages.
GenBank Accession No. DQ219343, dated Oct. 1, 2006, 2 pages.
GenBank Accession No. DQ219344, dated Oct. 1, 2006, 2 pages.
GenBank Accession No. DQ219345, dated Oct. 1, 2006, 2 pages.
GenBank Accession No. DQ219346, dated Oct. 1, 2006, 2 pages.
GenBank Accession No. DQ219347, dated Oct. 1, 2006,2 pages.
GenBank Accession No. DQ219348, dated Oct. 1, 2006, 2 pages.
GenBank Accession No. DQ219349, dated Oct. 1, 2006, 2 pages.
GenBank Accession No. DQ219350, dated Oct. 1, 2006, 2 pages.
GenBank Accession No. DQ219351, dated Oct. 1, 2006, 2 pages.
GenBank Accession No. DQ219352, dated Oct. 1, 2006, 2 pages.
GenBank Accession No. DQ350312, dated Dec. 31, 2006, 2 pages.
GenBank Accession No. DQ350313, dated Dec. 31, 2006, 2 pages.
GenBank Accession No. DQ350314, dated Dec. 31, 2006, 2 pages.
GenBank Accession No. DQ350315, dated Dec. 31, 2006, 2 pages.
GenBank Accession No. DQ350316, dated Dec. 31, 2006, 2 pages.
GenBankAccession No. DQ350317, dated Dec. 31, 2006, 2 pages.
GenBank Accession No. DQ350318, dated Dec. 31, 2006, 2 pages.
GenBank Accession No. DQ350319, dated Dec. 31, 2006, 2 pages.
GenBank Accession No. DQ350320, dated Dec. 31, 2006, 2 pages.
GenBank Accession No. DQ350321, dated Dec. 31, 2006, 2 pages.
GenBank Accession No. DQ350322, dated Dec. 31, 2006, 2 pages.
GenBank Accession No. DQ350323, dated Dec. 31, 2006, 2 pages.
GenBank Accession No. DQ350324, dated Dec. 31, 2006, 2 pages.
GenBank Accession No. DQ350325, dated Dec. 31, 2006, 2 pages.
GenBank Accession No. DQ350326, dated Dec. 31, 2006, 2 pages.
GenBank Accession No. DQ350327, dated Dec. 31, 2006, 2 pages.
GenBank Accession No. DQ350328, dated Dec. 31, 2006, 2 pages.
GenBank Accession No. DQ350329, dated Dec. 31, 2006, 2 pages.
GenBank Accession No. DQ350330, dated Dec. 31, 2006, 2 pages.
GenBank Accession No. DQ350331, dated Dec. 31, 2006, 2 pages.
GenBank Accession No. DQ350332, dated Dec. 31, 2006, 2 pages.
GenBank Accession No. DQ350333, dated Dec. 31, 2006, 2 pages.
GenBank Accession No. DQ350334, dated Dec. 31, 2006, 2 pages.
GenBank Accession No. DQ350335, dated Dec. 31, 2006, 2 pages.
GenBank Accession No. DQ350336, dated Dec. 31, 2006, 2 pages.
GenBank Accession No. DQ350337, dated Dec. 31, 2006, 2 pages.
GenBank Accession No. DQ350338, dated Dec. 31, 2006, 2 pages.
GenBank Accession No. DQ350339, dated Dec. 31, 2006, 2 pages.
GenBank Accession No. DQ350340, dated Dec. 31, 2006, 2 pages.
GenBank Accession No. DQ350341, dated Dec. 31, 2006, 2 pages.
GenBank Accession No. DQ350342, dated Dec. 31, 2006, 2 pages.
GenBank Accession No. DQ350343, dated Dec. 31, 2006, 2 pages.
GenBank Accession No. DQ350344, dated Dec. 31, 2006, 2 pages.
GenBank Accession No. DQ350345, dated Dec. 31, 2006, 2 pages.
GenBank Accession No. DQ350346, dated Dec. 31, 2006, 2 pages.
GenBank Accession No. DQ350347, dated Dec. 31, 2006, 2 pages.
GenBank Accession No. DQ350348, dated Dec. 31, 2006, 2 pages.
GenBank Accession No. DQ350349, dated Dec. 31, 2006, 2 pages.
GenBank Accession No. DQ350350, dated Dec. 31, 2006, 2 pages.
GenBank Accession No. DQ350351, dated Dec. 31, 2006, 2 pages.
GenBank Accession No. DQ350352, dated Dec. 31, 2006, 2 pages.
GenBank Accession No. DQ350353, dated Dec. 31, 2006, 2 pages.
GenBank Accession No. DQ350354, dated Dec. 31, 2006, 2 pages.
GenBank Accession No. DQ350355, dated Dec. 31, 2006, 2 pages.
GenBank Accession No. DQ350356, dated Dec. 31, 2006, 2 pages.
GenBank Accession No. DQ350357, dated Dec. 31, 2006, 2 pages.
GenBank Accession No. DQ350358, dated Dec. 31, 2006, 2 pages.
GenBank Accession No. DQ350359, dated Dec. 31, 2006, 2 pages.
GenBank Accession No. DQ350360, dated Dec. 31, 2006, 2 pages.
GenBank Accession No. DQ350361, dated Dec. 31, 2006, 2 pages.
GenBank Accession No. DQ350362, dated Dec. 31, 2006, 2 pages.
GenBank Accession No. DQ350363, dated Dec. 31, 2006, 2 pages.
GenBank Accession No. DQ205656, dated Jan. 18, 2007, 2 pages.
GenBank Accession No. ABA07806, dated Mar. 7, 2007, 2 pages.
GenBank Accession No. DQ131887, dated Mar. 7, 2007, 2 pages.
Ghosh, "Polyamines and plant alkaloids," *Indian J. Exp. Biol.*, 38:1086-1091 (2000).
Goldrick et al., "Molecular Genetic Analysis of the User Group Associated with Two Mouse Light Chain Genetic Markers," *J.ExpMed* 162:713-728 (1985).
Graham-Lorence et al., "P450s: Structural similarities and functional differences," *FASEB J.* 10:206-214 (1996).
Guo et al., "Protein Tolerance to Random Amino Acid Change," *PNAS*, 101(25):9205-9210 (2004).
Hao et al., "Mechanism of Nicotine N-Demethylation in Tobacco Cell Suspension Cultures," *Phytochemistry*, 41(2):477-482 (1995).
Hao et al., "Nicotine N-Demethylase in Cell-Free Preparations from Tobacco Cell Cultures," *Phytochemistry*, 42(2):325-329 (1996).
Hao et al., "Evidence in Favour of an Oxidative N-Demethylation of Nicotine to Nomicotine in Tobacco Cell Cultures," *Journal Plant Physiology*, 152:420-426 (1998).
Haseloff et al., "Simple RNA enzymes with new and highly specific endoribonuclease activities," *Nature*, 334:585-591 (1998).

(56) References Cited

OTHER PUBLICATIONS

Hayes et al., "Blotting techniques for the study of DNA, RNA, and proteins," *BMJ*, 299(14):965-968 (1989).
Hecht et al., "The relevance of tobacco-specific nitrosamines to human cancer," *Cancer Surveys*, 8(2):273-294 (1989).
Hecht, "Biochemistry, Biology, and Carcinogenicity of Tobacco-Specific N-Nitrosamines," *Chemical Research in Toxicology*, 11(6):559-603 (1998).
Helene et al., "Control of Gene Expression by Triple Helix-Forming Oligonucleotides," *Ann. N.Y. Acad. Sci.*, 660:27-36 (1992).
Helene, "The anti-gene strategy: control of gene expression by triplex-fanning-oligonucleotides," *Anti-Cancer Drug Des.*, 6:569-584 (1991).
Helliwell et al., "High-throughput vectors for efficient gene silencing in plants," *Funct. Plant Biol.*, 29:1217-1225 (2002).
Henikoff et al., "Single-Nucleotide Mutations for Plant Functional Genomics," *Annu. Rev. Plant Biol.*, 54:375-401 (2003).
Herbik et al., "Isolation, characterization and cDNA cloning of nicotianamine synthase from barley," *Eur J Biochem*, 265(1): 231-9 (1999).
Hibino et al., "Increase of Cinnamaldehyde Groups in Lignin of Transgenic Tobacco Plants Carrying an Antisense Gene for Cinnamyl Alcohol Dehydrogenase," *Biosci. Biotec. Biochem*, 59:929-931 (1995).
Hildering et al., "Chimeric Structure of the Tomato Plant After Seed Treatment with EMS and X-Rays," The Use of Induced Mutations in Plant Breeding, Pergamon Press, pp. 317-320 (1965).
Hill et al., "Functional analysis of conserved histidines in ADP-glucose pyrophosphorylase from *Escerichia coli*," *Biochem. Biophys. Res. Commun.*, 244:573-577 (1998) (Abstract only).
Hoekema et al., "A binary plant vector strategy based on separation of the vir- and T-region of the *Agrobacterium tumefaciens* Ti-plasmid," *Nature*, 303:179-180 (1983).
Hoffmann et al., "Tobacco-specific N-nitrosamines and Areca-derived N-nitrosamines: chemistry, biochemistry, carcinogenicity, and relevance to humans," *Journal of Toxicology and Environmental Health*, 41:1-52 (1994).
Huang et al., "Insights into Regulation and Function of the Major Stress-hlducedhsp70 Molecular Chaperone In Vivo: Analysis of Mice with Targeted Gene Disruption of the hsp70. 1 or hsp70.3 Gene," *Mol Cell Biol*, 21(24):8575-8591 (2001).
Ingelbrecht et al., "Posttranscriptional silencing of reporter transgenes in tobacco correlates with DNA methylation," *PNAS*, 91:10502-10506 (1994).
International Preliminary Report on Patentability in PCT/US07/087386 mailed Jun. 25, 2009, 6 pages.
International Search Report and the Written Opinion of the International Searching Authority, or the Declaration mailed on May 4, 2012, in International Application No. PCT/US2012/026864 (13 pages).
International Search Report and the Written Opinion of the International Searching Authority, or the Declaration mailed on Jul. 4, 2012, in International Application No. PCT/US2012/026795 (15 pages).
Isshiki et al., "Nonsense-mediated decay of mutant waxy mRNA in rice," *Plant Physiology*, 125:1388-1395 (2001).
Jack et. al., "Relative stability of nicotine to nornicotine conversion in three burley cultivars," Coresta Congress, Kyoto, Agro-Phyto groups, Abstract AP2 (2004).
Johnston et al., "Dosage-sensitive function of retinoblastoma related and convergent epigenetic control are required during the *Arabidopsis* life cycle," *PLoS Genet*, 6(6):e1000988 (2010).
Jorgensen et al., "Chalcone synthase cosuppression phenotypes in petunia flowers: comparison of sense vs. antisense constructs and single-copy vs. complex T-DNA sequences," *Plant Mol. Biol.*, 31:957-973 (1996).
Julio et al. "Reducing the content of nornicotine in tobacco via targeted mutation breeding," *Mol. Breeding*, 21:369-381 (2008).
Julio et al., Targeted Mutation Breeding as a tool for tobacco crop improvement, presentation made in Oct. 2008.

Kafri et al., "The regulatory utilization of genetic redundancy through responsive backup circuits," *PNAS*, 103(31):11653-11658 (2006).
Kempin et al., "Targeted disruption in *Arabidopsis*," *Nature*, 389:802-803 (1997).
Keskin et al., "A new, structurally nonredundant, diverse data set of protein-protein interfaces and its implications," *Protein Science*, 13:1043-1055 (2004).
Kim et al., "*Arabidopsis* CYP85A2, a Cytochrome P450, Mediates the Baeyer-Villiger Oxidation of Castasterone to Brassinolide in Brassinosteroid Biosynthesis," *Plant Cell*, 17:2397-2412 (2005).
Klahre et al., "High molecular weight RNAs and small interfering RNAs induce systemic posttranscriptional gene silencing in plants," *PNAS*, 99:11981-11986 (2002).
Klink et al., The Efficacy of RNAi in the Study of the Plant Cytoskeleton, *J Plant Growth Regul.*, 19:371-384 (2000).
Koornneef, "Chapter 1: Classical mutagenesis in higher plants," *Molecular Plant Biology*, Gilmartin and Bowler, ed., Oxford University Press, pp. 1-11 (2002).
Koshinsky et al., "Cre-lox site-specific recombination between *Arabidopsis* and tobacco chromosomes," *Plant J.* 23(6):715-722 (2000).
Kusaba et al., "*Low glutelin content1*: A Dominant Mutation That Suppresses the Glutelin Multigene Family via RNA Silencing in Rice," *Plant Cell*, 15:1455-1467 (2003).
Kynast et al., "Dissecting the maize genome by using chromosome addition and radiation hybrid lines," *PNAS*, 101(26):9921-9926 (2004).
Lazaret al., "Transforming Growth Factor α Mutation of Aspartic Acid 47 and Leucine 48 Results in Different Biological Activities," *Mol. Cell. Biol.*, 8(3):1247-1252 (1988).
Levin et al., "Methods of double-stranded RNA-mediated gene inactivation in *Arabidopsis* and their use to define an essential gene in methionine biosynthesis," *Plant Mol. Biol.*, 44:759-775 (2000).
Lewis et al., Three nicotine demethylase genes mediate nornicotine biosynthesis in *Nicotiana tabacum* L.: Functional characterization of the CYP82E10 gene, *Phytochemistry*, 71:1988-1998 (2010).
Lewis, et al. "RNA interference (RNAi)-induced suppression of nicotine demethylase activity reduces levels of a key carcinogen in cured tobacco leaves." *Plant Biotechnology Journal*, 6:1-9 (2008).
Liu et al., "High-Stearic and High-Oleic Cottonseed Oils Produced by Hairpin RNA-Mediated Post-Transcriptional Gene Silencing," *Plant Physiol.*, 129:1732-1743 (2002).
Liu et al., "Identification and characterization of HTD2: a novel gene negatively regulating tiller bud outgrowth in rice," *Planta*, 230(4):649-658 (2009).
Liu et al. "Genetic and transformation studies reveal negative regulation of ERS 1 ethylene receptor signaling in *Arabidopsis*," *BMC Plant Biol*, 10:60-73 (2010).
Maher, "DNA Triple-Helix Formation: An Approach to Artificial Gene Repressors?" *BioEssays*, 14(12):807-815 (1992).
Maniatis et al., "Regulation of inducible and tissue-specific gene expression," *Science*, 236:1237-1245 (1987).
Mansoor et al. "Engineering novel traits in plants through RNA interference," *Trends in Plant Science*, 11(11):1-7 (2006).
Maquat, "Nonsense-mediated mRNA decay," *Curr. Biol.*, 12(6):R196-R197 (2002).
Matthew, "RNAi for plant functional genomics," *Comparative and Functional Genomics*, 5:240-244 (2004).
McDougall et al., "Detection of Viral DNA and RNA by In Situ Hybridization," *J. Histochem. Cytochem.*, 34:33-38 (1986).
McKinney et al., "Sequence-based identification of T-DNA insertion mutations in *Arabidopsis*: actin mutants act2-1 and act4-1 ," *Plant J.*, 8(4):613-622 (1995).
Mesnard et al., "Evidence for the involvement of tetrahydrofolate in the demethylation of nicotine by *Nicotiana plumbaginifolia* cell-suspension cultures," *Planta*, 214:911-919 (2002).
Mette et al., "Transcriptional silencing and promoter methylation triggered by double-stranded RNA," *EMBO J.* 19(19):5194-5201 (2000).
Mol et al., "Regulation of plant gene expression by antisense RNA," *FEBS Lett.*, 268(2):427-430 (1990).

(56) References Cited

OTHER PUBLICATIONS

Napoli et al., "Introduction of a Chimeric Chalcone Synthase Gene into Petunia Results in Reversible Co-Suppression of Homologous Genes in trans," *Plant Cell*, 2:279-289 (1990).
Nawrath et al., "Salicylic Acid Induction-Deficient Mutants of *Arabidopsis* Express PR-2 and PR-5 and Accumulate High Levels of Camalexin after Pathogen Inoculation," *Plant Cell*, 11:1393-1404 (1999).
Needleman et al., "A General Method Applicable to the Search for Similarities in the Amino Acid Sequence of Two Proteins," *J. Mol. Biol*, 48:443-453 (1970).
Nelson et al., "Comparative Genomics of Rice and *Arabidopsis*. Analysis of 727 Cytochrome P450 Genes and Pseudogenes from a Monocot and a Dicot," *Plant Physiol.*, 135:756-772 (2004).
Nelson et al., "Comparison of cytochrome P450 (CYP) genes from the mouse and human genomes, including nomenclature recommendations for genes, pseudogenes and alternative-splice variants," *Pharmacogenetics*, 14:1-18 (2004).
Ng et al., "Specific Detection and Confirmation of *Campylobacter jejuni* by DNA Hybridization and PCR," *Appl. Environ. Microbiol.* 63(11):4558-4563 (1997).
Nishihara et al., "Flavanoid components and flower color change in transgenic tobacco plants by suppression of chalcone isomerase gene," *FEBS Lett.*, 579:6074-6078 (2005).
Odell et al., "Identification of DNA sequences required for activity of the cauliflower mosaic virus 35S promoter," *Nature*, 313:810-812 (1985).
Office Action mailed on Oct. 18, 2006, in U.S. Appl. No. 10/293,252.
Office Action mailed on Oct. 30, 2006, in U.S. Appl. No. 10/686,947.
Office Action mailed on Nov. 14, 2006, in U.S. Appl. No. 10/387,346.
Office Action mailed on Nov. 14, 2006, in U.S. Appl. No. 10/340,861.
Office Action mailed on May 4, 2007, in U.S. Appl. No. 10/943,507.
Office Action mailed on Jun. 12, 2007, in U.S. Appl. No. 10/934,944.
Ogita et al., "Application of RNAi to confirm theobromine as the major intermediate for caffeine biosynthesis in coffee plants with potential for construction of decaffeinated varieties," *Plant Mol. Biol.*, 54:931-941 (2004).
Ohshima et al., "Nucleotide sequence of the PR-I gene of *Nicotiana tabacum*," *FEBS Letters*, 225:243-246 (1987).
Oliver et al., "Inhibition of tobacco NADH-hydroxypyruvate reductase by expression of a heterologous antisense RNA derived from a cucumber cDNA: Implications for the mechanism of action of antisense RNAs," *Mol. Gen Genet*, 239(3):425-34 (1993).
Pearson et al., "Improved tools for biological sequence comparison," *PNAS*, 85:2444-2448 (1988).
Peele et al., "Formation of Tobacco-specific Nitrosamines in Flue-cured Tobacco," CORESTA Meeting, Agro-Phyto Groups, Suzhou, China (1999).
Pickett et al., "Seeing Double: Appreciating Genetic Redundancy," *Plant Cell*, 7:1347-1356 (1995).
Plant Variety Protection Office (USDA-AMS, Beltsville, MD, http://www.ars-grin.gov/cgi-bin/npgs/htmllpvp.pl?Tobbaco, accessed Feb. 2009).
Puchta et al., "Two different but related mechanisms are used in plants for the repair of genomic double-strand breaks by homologous recombination," *PNAS*, 93:5055-5060 (1996).
Qin et al., "Cre recombinase-mediated site-specific recombination between plant chromosomes," *PNAS*, 91:1706-1710 (1994).
Qiu et al. "A computational study of off-target effects of RNA interference." *Nucleic Acids Research*, 33(6)1834-1847 (2005).
Ralston et al., "Cloning, Heterologous Aristolochene-1,3-Dihydroxylase from Expression, and Functional Characterization of 5-epi-Tobacco (*Nicotiana tabacum*)," *Arch. Biochem. Biophys.*, 393(2):222-235 (2001).
Reid et al., "Studies on the Fermentation of Tobacco 1. The Microflora of Cured and Fermenting Cigar-leaf Tobacco," Bulletin 356, Pennsylvania Agricultural Experiment Station, State College, PA, 18 pages (1938).
Rodermel et al., "Nuclear-Organelle Interactions: Nuclear Antisense Gene Inhibits Ribulose Biphosphate Carboxylase Enzyme Levels in Transformed Tobacco Plants," *Cell*, 55:673-681(1988).
Rohr et al., "Tandem inverted repeat system for selection of effective transgenic RNAi strains of *Chlamydomonas*," *Plant J.* 40:611-621 (2004).
Salehuzzaman et al., "Isolation and characterization of a cDNA encoding granule-bound starch synthase in cassava (*Afanihot esculenta* Crantz) and its antisense expression in potato," *PlantMd. Biol*, 23(5):947-62 (1993).
Schenk et al., "Coordinated plant defense responses in *Arabidopsis* revealed by microarray analysis," *PNAS*, 97(21):11655-11660 (2000).
Schnable et al., "Genetic recombination in plants," *Curr. Opin. Plant Biol.*, 1:123-129 (1998).
Schopfer et al., "Identification of elicitor-induced cytochrome P450s of soybean (*Glycine max* L.) using differential display of mRNA," *Mol. Gen. Genet.*, 258:315-322 (1998).
Seal et al., "Isolation of a *Pseudomonas solanacearum*-Specific DNA Probe by Subtraction Hybridization and Construction of Species-Specific Oligonucleotide Primers for Sensitive Detection by the Polymerase Chain Reaction," *Appl. Environ. Microbiol.*, 58(2):3751-3758 (1992).
Sequence 6912fl obtained from the Internet at http://mrg.pscsiken.go.ip/nicotiana/menu/069.html on Dec. 6, 2007, 1 page.
Shah et al., "Expression of Silent Mutations in Disease Phenotype," Abstract for presentation at 11th International Congress of Human Genetics, 1 page, (2006).
Shen et al., "Resistance Gene Candidates Identified by PCR with Degenerate Oligonucleotide Primers Map to Clusters of Resistance Genes in Lettuce," *Molecular Plant-Microbe Interactions*, 11(8):815-823 (1998).
Shew et al. (Eds.), "Compendium of Tobacco Diseases," published by American Phytopathology Society, 99 pages (1991).
Siminszky et al., "Conversion of nicotine to nornicotine in *Nicotiana tabacum* is mediated by CYP82E4, a cytochrome P450 monooxygenase," *PNAS*, 102(41):14919-14924 (2005).
Sinvany-Villalobo et al., "Expression in Multigene Families. Analysis of Chloroplast and Mitochondrial Proteases," *Plant Physiol*, 135:1336-1345 (2004).
Skarnes, "Entrapment Vectors: A New Tool for Mammalian Genetics," *Bio/Technology*, 8:827-831 (1990).
Smith et al., "Comparison of Biosequences," *Adv. Appl. Math.*, 2:482-489 (1981).
Smith et al., "Total silencing by intron-spliced hairpin RNAs," *Nature*, 407:319-320 (2000).
Spradling et al., "Gene disruptions using P transposable elements: An integral component of the *Drosophila* genome project," *PNAS*, 92:10824-10830 (1995).
Stalberg et al., "Deletion analysis of a 2S seed storage protein promoter of *Brassica napus* in transgenic tobacco," *Plant Mol. Biol.*, 23:671-683 (1993).
Sundaresan et al., "Patterns of gene action in plant development revealed by enhancer trap and gene trap transposable elements," *Genes Dev.*, 9:1797-1810 (1995).
Sureka et al., "Positive Feedback and Noise Activate the Stringent Response Regulator Rel in Mycobacteria," *PLoS One*, 3(3):d 771 (2008).
Takeda et al., "Differentiation between Wild and Vaccine-Derived Strains of Poliovirus by Stringent Microplate Hybridization of PCR Products," *J Clin. Microbial.*, 32:202-204 (1994).
Takemoto et al., "Molecular Cloning of a Defense-Response-Related Cytochrome P450 Gene from Tobacco," *Plant Cell Physiol.*, 40(12):1232-1242 (1999).
Takken et al. "A functional cloning strategy, based on a binary P Y X-expression vector, to isolate HR-inducing cDNAs of plant pathogens." *The Plant Journal*, 24(2): 275-283 (2000).

(56) References Cited

OTHER PUBLICATIONS

Tang et al., "Using RNAi to improve plant nutritional value: from mechanism to application," *Trends in Biotechnology*, 22(9):463-469 (2004).
Tavernarakis et al., "Heritable and inducible genetic interference by double-stranded RNA encoded by transgenes," *Nat. Genet.*, 24:180-183 (2000).
Temple et al., "Modulation of glutamine synthetase gene expression in tobacco by the introduction of an alfalfa glutamine synthetase gene in sense and antisense orientation: molecular and biochenlical analysis," *Mol Gen Genet*, 236(2-3):315-25 (1993).
Thomas et al., "Size constraints for targeting post-transcriptional gene silencing and for RNA directed methylation in *Nicotiana benthamiana* using a potato virus X vector," *Plant J.*, 25(4):417-425 (2001).
Thornton et al., "From structure to function: Approaches and limitations," *Nature Structural Biology, StructuralGenomics Supplement*, pp. 991-994 (2000).
Till et al., "Discovery of induced point mutations in maize genes by Tilling," *BMC Plant Biology*, 4:12 (2004).
Toscano et al., "A silent mutation (2939G>A, exon 6; CYP2D6*59) leading to impaired expression and function of CYP2D6," *Pharmacogenet. Genomics*, 16(10):767-770 (2006).
Travella, et al. "RNA Interference-Based Gene Silencing as an Efficient Tool for Functional Genomics in Hexaploid Bread Wheat." *Plant Physiology*, 142:6-20 (2006).
Trevanion et al., "NADP-Malate Dehydrogenase in the C4 Plant *Flaveria bidentis,*" *Plant Physiol*, 113(4):1153-1165 (1997).
Turner et al., "Post-transcriptional gene-silencing and RNA interference: genetic immunity, mechanisms and applications," *J. Chem. Technol. Biotechnol.*, 75:869-882 (2000).
United States, "Tobacco in the United States," Miscellaneous Publication No. 867, U.S. Dept. of Agriculture, Agricultural Marketing Service, 27 pages (1979).
Vaistij et al., "Spreading of RNA Targeting and DNA Methylation in RNA Silencing Requires Transcription of the Target Gene and a Putative RNA-Dependent RNA Polymerase," *Plant Cell*, 14:857-867 (2002).
Van der Krol et al., "An anti-sense chalcone synthase gene in transgenic plants inhibits flower pigmentation," *Nature*, 333:866-869 (1988).
Van der Krol et al., "Antisense genes in plants: an overview," *Gene*, 72:45-50 (1988).
Vaucheret et al., "Post-transcriptional gene silencing in plants," *J.Cell Sci.*, 114:3083-3091 (2001).
Veena et al.,"Glyoxalase I from *Brassica juncea*. molecular cloning, regulation and its overexpression confer tolerance in transgenic tobacco under stress," *Plant Journal*, 17(4):385-395 (1999).
Verdaguer et al., "Functional organization of the cassava vein mosaic virus (CsVMV) promoter," *Plant Mol. Biol.*, 37(6):1055-1067 (1998).
Verkerk, "Chimerism of the tomato plant after seed irradiation with fast neutrons," *Neth. J. Agric. Sci.*, 19:197-203 (1971).
Voss et al., "The role of enhancers in the regulation of cell-type-specific transcriptional control," *Trends Biochem. Sci.*, 11(7):287-289 (1986).
Wang et al., "Suppression of a P450 hydroxylase gene in plant trichome glands enhances natural product-based aphid resistance," *Nat. Biotechnol.*, 19:371-374 (2001).
Wang et al., "Isolation and characterization of the CYP7JD16 trichome-specific promoter from *Nicotania tabacum* L," *J Exp. Botany*, 53(376):1891-1897 (2002).
Wang et al., "Elucidation of the functions of genes central to diterpene metabolism in tobacco trichomes using post-transcriptional gene silencing," *Planta*, 216:686-691 (2003).
Waterhouse et al., "Virus resistance and gene silencing in plants can be induced by simultaneous expression of sense and antisense RNA," *PNAS*, 95:13959-13964 (1998).
Weigel et al., "A developmental switch sufficient for flower initiation in diverse plants," *Nature*, 377:495-500 (1995).

Weising et al., "Foreign Genes in Plants: Transfer, Structure, Expression, and Applications," *Ann. Rev. Genetics*, 22:421-477 (1988).
Werck-Reichhart et al., "Cytochromes P450: a success story," *Genome Biology*, 1 (6):reviews3003.1-3003.9 (2000).
Werck-Reichhart et al., "Cytochromes P450," The *Arabidopsis Book*, American Society of Plant Biologists, 28 pages (2002).
Wernsman et al., "Time and site of nicotine conversion in tobacco," *Tobacco Science*, 167(22):226-228 (1968).
Wernsman et al., "Relative Stability of Alleles at the Nicotine Conversion Locus of Tobacco," *Tobacco Science*, 14:34-36 (1970).
Wernsman et al., "Chapter Seventeen: Tobacco." *Cultivar Development. Crop Species.*, W. H. Fehr (ed.), MacMillan Publishing Go., Inc., New York, N.Y., pp. 669-698 (1987).
Wesley et al., "Construct design for efficient, effective and high-throughput gene silencing in plants," *The Plant Journal*, 27(6): 581-590 (2001).
Wetmur, "DNA Probes: Applications ofthe Principles ofNucleic Acid Hybridization" *Critical Reviews in Bio. and Mol. Biol.*, 26:227-259, (1991).
Whitbred et al., "Molecular Characterization of CYP73A9 and CYP82Al P450 Genes Involved in Plant Defense in Pea," *Plant Physiol.*, 124:47-58 (2000).
Wu et al. "Herbivory Rapidly Activates MAPK Signaling in Attacked and Unattacked Leaf Regions but Not between Leaves of *Nicotiana attenuata.*" *The Plant Cell*, 19:1096-1122 (2007).
Xiong et al., "Different effects on ACC oxidase gene silencing triggered by RNA interference in transgenic tomato," *Plant Cell*, 23:639-646 (2004).
Xu et al. "Computational Estimation and Experimental Verification of Off-Target Silencing during Posttranscriptional Gene Silencing in Plants," *Plant Physiology*, 142:429-440 (2006).
Xu et al., "Biochemical and molecular characterizations of nicotine demethylase in tobacco," *Physiologia Plantarum*, 129(2):307-319 (2007).
Zwart et al., "Rapid Screening for Freshwater Bacterial Groups by Using Reverse Line Blot Hybridization," *Appl. Environ. Microbiol.*, 69(10):5875-5883 (2003).
ARS-GRIN: PI 543792, "*Nicotiana tabacum*—'TN 90'" http://www.ars-grin.gov/cgi-bin/npgs/acc/display.pl?1438728, Retrieved Date: Sep. 2013 (2pp).
Horlow et al., "Transfer of cytoplasmic male sterility by spontaneous androgenesis in tobacco (*Nicotiana tabacum* L.)" *Euphytica* 66:45-53 (1993).
Notification Concerning Transmittal of International Preliminary Report on Patentability in corresponding PCT Application No. PCT/US2012/026864 mailed Sep. 12, 2013 (8 pp).
Notification of Transmittal of the International Search Report and the Written Opinion of the International Searching Authority, or the Declaration, PCT/US2014/011035, Apr. 23, 2014, 11 pages.
Ruiz et al., "Nicotine free and salt-tolerant tobacco plants obtained by grafting to salinity-resistant rootstocks of tomato," *Physiologia Plantarum*, vol. 124, No. 4, Aug. 1, 2005, pp. 465-475.
Chen et al., "Toxicological analysis of low-nicotine and nicotine-free cigarettes," *Toxicology*, vol. 249, No. 2-3, Jul. 30, 2008, 19 pages.
Invitation to Pay Additional Fees, PCT/US2014/019381, Jun. 23, 2014, 8 pages.
Jack et al., "Relative Stability of Nicotine to Nornicotine Conversion in Three Burley Cultivars," 18 pages, 36 slides (basis for Jack et al., published in COREST Congress Abstract AP2, Kyoto (2004) Agro Phyto Groups; 32 pages (unpaginated, abstract appearing on p. 11)).
Mann et al., "Inheritance of the Conversion of Nicotine to Nornicotine in Varieties of *Nicotiana tabacum* L. and Related Amphiploids," *Crop Sci.*, 4:349-53 (1964).
Bindler et al., "CORESTA Task Force Genetically Modified Tobacco: Detection Methods," 1999, 41 pages.
Saunders et al., "The Use of AFLP Techniques for DNA Finger-printing in Plants," CEQ 2000XL, Beckman Coulter, 2001, 8 pages.
Slater et al., Plant biotechnology: the genetic manipulation of plants 39 (Oxford University Press 2008) Chapter 2, pp. 37-53, $2^{nd}$ ed.

(56) References Cited

OTHER PUBLICATIONS

T. David Reed, "Curing Tobacco," 2008 Flue-cured Tobacco Production Guide, pp. 61-64.
International Search Report and Written Opinion Corresponding to International Application No. PCT/US2014/019381; Date of Mailing: Aug. 28, 2014.
Invitation to Pay Additional Fees, PCT/US2015/018408, mailed May 18, 2015, 8 pages.
NCSU Office of the Dean, *Electronic Administrative Briefings*, Jun. 2008, 11 pages.
Chen et al., "Toxicological analysis of low-nicotine and nicotine free cigarettes," *Toxicology*, vol. 249, No. 2-3, Jul. 30, 2008, 19 pages.
Hadden, et al., UT Extension Publications (1999) SP277S-5/99 (Rev) Black Root Rot of Tobacco; University of Tennessee (AES), Knoxville; 5 pages.
Notification of Transmittal of the International Search Report and the Written Opinion of the International Searching Authority, or the Declaration, PCT/US2015/018408, Jul. 6, 2015, 11 pages.
Notification of Transmittal of the International Preliminary Report on Patentability and the Written Opinion of the International Searching Authority, PCT/US2014/011035, Jul. 23, 2015, 8 pages.
International Preliminary Report on Patentability and Written Opinion corresponding to International Application No. PCT/US2015/018387; Date of Mailing: Sep. 16, 2016; 11 pages.

\* cited by examiner

SEQUENCE LISTING

```
<160> NUMBER OF SEQ ID NOS: 12

<210> SEQ ID NO 1
<211> LENGTH: 1554
<212> TYPE: DNA
<213> ORGANISM: Nicotiana tabacum
<220> FEATURE:
<221> NAME/KEY: Mutation
<222> LOCATION: (986)..(986)
<223> OTHER INFORMATION: G to A

<400> SEQUENCE: 1
atgctttctc ccatagaagc cattgtagga ctagtaacct tcacatttct cttcttcttc    60
ctatggacaa aaaaatctca aaaaccttca aaacccttac caccgaaaat ccccggagga   120
```

```
tggccggtaa tcggccatct tttccacttc aatgacgacg gcgacgaccg tccattagct      180
cgaaaactcg gagacttagc tgacaaatac ggccccgttt tcacttttcg gctaggcctt      240
ccccttgtct tagttgtaag cagttacgaa gctgtaaaag actgtttctc tacaaatgac      300 gccattttt ccaatcgtcc agcttttctt tacggcgatt accttggcta caataatgcc       360
atgctatttt tggccaatta cggaccttac tggcgaaaaa atcgaaaatt agttattcag      420
gaagttctct ccgctagtcg tctcgaaaaa ttcaaacacg tgagatttgc aagaattcaa      480
gcgagcatta agaatttata tactcgaatt gatggaaatt cgagtacgat aaatttaact      540
gattggttag aagaattgaa ttttggtctg atcgtgaaga tgatcgctgg aaaaaattat      600
gaatccggta aaggagatga acaagtggag agatttaaga aagcgtttaa ggattttatg      660
attttatcaa tggagtttgt gttatgggat gcatttccaa ttccattatt taaatgggtg      720
gattttcaag ggcatgttaa ggctatgaaa aggacttta aagatataga ttctgttttt        780
cagaattggt tagaggaaca tattaataaa agagaaaaa tggaggttaa tgcagaaggg        840
aatgaacaag atttcattga tgtggtgctt tcaaaaatga gtaatgaata tcttggtgaa      900
ggttactctc gtgatactgt cattaaagca acggtgttta gtttggtctt ggatgcagca      960
gacacagttg ctcttcacat aaattaggga atggcattat tgataaacaa tcaaaaggcc     1020
ttgacgaaag cacaagaaga gatagacaca aaagttggta aggacagatg ggtagaagag     1080
agtgatatta aggatttggt atacctccaa gctattgtta agaagtgtt acgattatat       1140 ccaccaggac ctttgttagt accacacgaa aatgtagaag attgtgttgt tagtggatat     1200
cacattccta aagggacaag attattcgca aacgtcatga aactgcaacg tgatcctaaa     1260
ctctggtctg atcctgatac tttcgatcca gagagattca ttgctactga tattgacttt     1320
cgtggtcagt actataagta tatcccgttt ggttctggaa gacgatcttg tccagggatg     1380
acttatgcat tgcaagtgga acacttaaca atggcacatt tgatccaagg tttcaattac     1440
agaactccaa atgacgagcc cttggatatg aaggaaggtg caggcataac tatacgtaag     1500
gtaaatcctg tggaactgat aatagcgcct cgcctggcac ctgagcttta ttaa           1554
```

<210> SEQ ID NO 2
<211> LENGTH: 1554
<212> TYPE: DNA
<213> ORGANISM: Nicotiana tabacum
<220> FEATURE:
<221> NAME/KEY: Mutation
<222> LOCATION: (1266)..(1266)
<223> OTHER INFORMATION: G to A

<400> SEQUENCE: 2

```
atggtttctc ccgtagaagc cattgtagga ctagtaaccc ttacacttct cttctacttc       60
ctatggccca aaaaatttca aataccttca aaaccattac caccgaaaat tcccggaggg      120
tggccggtaa tcggccatct tttctacttc gatgatgacg gcgacgaccg tccattagct      180
cgaaaactcg gagacttagc tgacaaatac ggcccggttt tcactttccg gctaggcctt      240
ccgcttgtgt tagttgtaag cagttacgaa gctgtaaaag actgcttctc tacaaatgac      300
gccattttct ccaatcgtcc agcttttctt tacggtgaat accttggcta cagtaatgcc      360
atgctatttt tgacaaaata cggaccttat tggcgaaaaa atagaaaatt agtcattcag      420
gaagttctct ctgctagtcg tctcgaaaaa ttgaagcacg tgagatttgg taaaattcaa      480
acgagcatta agagtttata cactcgaatt gatggaaatt cgagtacgat aaatctaact      540
```

```
gattggttag aagaattgaa ttttggtctg atcgtgaaaa tgatcgctgg gaaaaattat     600
gaatccggta aaggagatga acaagtggag agatttagga aagcgtttaa ggattttata     660
attttatcaa tggagtttgt gttatgggat gcttttccaa ttccattgtt caaatgggtg     720
gattttcaag gccatgttaa ggccatgaaa aggacattta aggatataga ttctgttttt     780
cagaattggt tagaggaaca tgtcaagaaa agagaaaaaa tggaggttaa tgcacaaggg     840
aatgaacaag atttcattga tgtggtgctt tcaaaaatga gtaatgaata tcttgatgaa     900
ggttactctc gtgatactgt cataaaagca acagtgttta gtttggtctt ggatgctgcg     960
gacacagttg ctcttcacat gaattgggga atggcattac tgataaacaa tcaacatgcc    1020
ttgaagaaag cacaagaaga gatcgataaa aaagttggta aggaaagatg ggtagaagag    1080
agtgatatta aggatttggt ctacctccaa gctattgtta agaagtgtt acgattatat      1140 ccaccaggac ctttattagt acctcatgaa aatgtagagg attgtgttgt tagtggatat    1200
cacattccta aagggactag actattcgcg aacgttatga aattgcagcg cgatcctaaa    1260
ctctgatcaa atcctgataa gtttgatcca gagagattct tcgctgatga tattgactac    1320
cgtggtcagc actatgagtt tatcccattt ggttctggaa gacgatcttg tccggggatg    1380
acttatgcat tacaagtgga acacctaaca atagcacatt tgatccaggg tttcaattac    1440
aaaactccaa atgacgagcc cttggatatg aaggaaggtg caggattaac tatacgtaaa    1500
gtaaatcctg tagaagtgac aattacggct cgcctggcac tgagcttta ttaa            1554
```

<210> SEQ ID NO 3
<211> LENGTH: 328
<212> TYPE: PRT
<213> ORGANISM: Nicotiana tabacum

<400> SEQUENCE: 3

```
Met Leu Ser Pro Ile Glu Ala Ile Val Gly Leu Val Thr Phe Thr Phe
1               5                  10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
```

```
                195                 200                 205
Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
                260                 265                 270

Lys Met Glu Val Asn Ala Glu Gly Asn Glu Gln Asp Phe Ile Asp Val
                275                 280                 285

Val Leu Ser Lys Met Ser Asn Glu Tyr Leu Gly Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn
                325

<210> SEQ ID NO 4
<211> LENGTH: 421
<212> TYPE: PRT
<213> ORGANISM: Nicotiana tabacum

<400> SEQUENCE: 4

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
                20                  25                  30

Leu Pro Pro Lys Ile Pro Gly Gly Trp Pro Val Ile Gly His Leu Phe
                35                  40                  45

Tyr Phe Asp Asp Asp Gly Asp Asp Arg Pro Leu Ala Arg Lys Leu Gly
                50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Glu Tyr Leu Gly Tyr Ser Asn Ala Met Leu Phe Leu Thr Lys Tyr Gly
                115                 120                 125

Pro Tyr Trp Arg Lys Asn Arg Lys Leu Val Ile Gln Glu Val Leu Ser
                130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
                195                 200                 205

Val Glu Arg Phe Arg Lys Ala Phe Lys Asp Phe Ile Ile Leu Ser Met
                210                 215                 220

Glu Phe Val Leu Trp Asp Ala Phe Pro Ile Pro Leu Phe Lys Trp Val
225                 230                 235                 240
```

```
Asp Phe Gln Gly His Val Lys Ala Met Lys Arg Thr Phe Lys Asp Ile
            245                 250                 255

Asp Ser Val Phe Gln Asn Trp Leu Glu Glu His Val Lys Lys Arg Glu
        260                 265                 270

Lys Met Glu Val Asn Ala Gln Gly Asn Glu Gln Asp Phe Ile Asp Val
    275                 280                 285

Val Leu Ser Lys Met Ser Asn Glu Tyr Leu Asp Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu
            420

<210> SEQ ID NO 5
<211> LENGTH: 1554
<212> TYPE: DNA
<213> ORGANISM: Nicotiana tabacum

<400> SEQUENCE: 5
atgctttctc ccatagaagc cattgtagga ctagtaacct tcacatttct cttcttcttc        60
ctatggacaa aaaatctca aaaaccttca aaacccttac caccgaaaat ccccggagga       120
tggccggtaa tcggccatct tttccacttc aatgacgacg cgacgaccg tccattagct       180 cgaaaactcg gagacttagc tgacaaatac ggccccgttt tcacttttcg gctaggcctt       240
ccccttgtct tagttgtaag cagttacgaa gctgtaaaag actgtttctc tacaaatgac       300
gccatttttt ccaatcgtcc agcttttctt tacggcgatt accttggcta caataatgcc       360
atgctatttt tggccaatta cggaccttac tggcgaaaaa atcgaaaatt agttattcag       420
gaagttctct ccgctagtcg tctcgaaaaa ttcaaacacg tgagatttgc aagaattcaa       480
gcgagcatta agaatttata tactcgaatt gatggaaatt cgagtacgat aaatttaact       540
gattggttag aagaattgaa ttttggtctg atcgtgaaga tgatcgctgg aaaaaattat       600
gaatccggta aggagatgaa acaagtggag agatttaaga aagcgtttaa ggattttatg       660
attttatcaa tggagtttgt gttatgggat gcatttccaa ttccattatt taaatgggtg       720
gattttcaag gcatgttaa ggctatgaaa aggactttta agatataga ttctgttttt       780 cagaattggt tagaggaaca tattaataaa agagaaaaaa tggaggttaa tgcagaaggg       840
aatgaacaag atttcattga tgtggtgctt tcaaaaatga gtaatgaata tcttggtgaa       900
ggttactctc gtgatactgt cattaaagca acggtgttta gtttggtctt ggatgcagca       960
gacacagttg ctcttcacat gaattgggga atggcattat tgataaacaa tcaaaaggcc      1020
ttgacgaaag cacaagaaga gatagacaca aaagttggta aggacagatg ggtagaagag      1080
```

```
agtgatatta aggatttggt atacctccaa gctattgtta aagaagtgtt acgattatat      1140
ccaccaggac ctttgttagt accacacgaa aatgtagaag attgtgttgt tagtggatat      1200
cacattccta aagggacaag attattcgca aacgtcatga aactgcaacg tgatcctaaa      1260
ctctggtctg atcctgatac tttcgatcca gagagattca ttgctactga tattgacttt      1320
cgtggtcagt actataagta tatcccgttt ggttctggaa gacgatcttg tccagggatg      1380
acttatgcat tgcaagtgga acacttaaca atggcacatt tgatccaagg tttcaattac      1440
agaactccaa atgacgagcc cttggatatg aaggaaggtg caggcataac tatacgtaag      1500
gtaaatcctg tggaactgat aatagcgcct cgcctggcac ctgagcttta ttaa          1554
```

<210> SEQ ID NO 6
<211> LENGTH: 1554
<212> TYPE: DNA
<213> ORGANISM: Nicotiana tabacum

<400> SEQUENCE: 6

```
atggtttctc ccgtagaagc cattgtagga ctagtaaccc ttacacttct cttctacttc       60
ctatggccca aaaaatttca ataccttca aaaccattac caccgaaaat tcccggaggg       120
tggccggtaa tcggccatct tttctacttc gatgatgacg gcgacgaccg tccattagct      180
cgaaaactcg gagacttagc tgacaaatac ggcccggttt tcactttccg gctaggcctt      240
ccgcttgtgt tagttgtaag cagttacgaa gctgtaaaag actgcttctc tacaaatgac      300
gccattttct ccaatcgtcc agcttttctt tacggtgaat accttggcta cagtaatgcc      360
atgctatttt tgacaaaata cggaccttat tggcgaaaaa atagaaaatt agtcattcag      420
gaagttctct ctgctagtcg tctcgaaaaa ttgaagcacg tgagatttgg taaaattcaa      480
acgagcatta agagtttata cactcgaatt gatggaaatt cgagtacgat aaatctaact      540
gattggttag aagaattgaa ttttggtctg atcgtgaaaa tgatcgctgg gaaaaattat      600
gaatccggta aggagatga acaagtggag agatttagga aagcgtttaa ggattttata      660
attttatcaa tggagtttgt gttatgggat gcttttccaa ttccattgtt caaatgggtg      720
gattttcaag gccatgttaa ggccatgaaa aggacattta aggatataga ttctgttttt      780
cagaattggt tagaggaaca tgtcaagaaa agagaaaaaa tggaggttaa tgcacaaggg      840
aatgaacaag atttcattga tgtggtgctt tcaaaaatga gtaatgaata tcttgatgaa      900
ggttactctc gtgatactgt cataaaagca acagtgttta gtttggtctt ggatgctgcg      960
gacacagttg ctcttcacat gaattgggga atggcattac tgataaacaa tcaacatgcc      1020
ttgaagaaag cacaagaaga gatcgataaa aaagttggta aggaaagatg ggtagaagag      1080
agtgatatta aggatttggt ctacctccaa gctattgtta aagaagtgtt acgattatat      1140
ccaccaggac ctttattagt acctcatgaa aatgtagagg attgtgttgt tagtggatat      1200
cacattccta aagggactag actattcgcg aacgttatga aattgcagcg cgatcctaaa      1260
ctctggtcaa atcctgataa gtttgatcca gagagattct tcgctgatga tattgactac      1320
cgtggtcagc actatgagtt tatcccattt ggttctggaa gacgatcttg tccggggatg      1380
acttatgcat tacaagtgga acacctaaca atagcacatt tgatccaggg tttcaattac      1440
aaaactccaa atgacgagcc cttggatatg aaggaaggtg caggattaac tatacgtaaa      1500
gtaaatcctg tagaagtgac aattacggct cgcctggcac ctgagcttta ttaa           1554
```

<210> SEQ ID NO 7

<211> LENGTH: 517
<212> TYPE: PRT
<213> ORGANISM: Nicotiana tabacum

<400> SEQUENCE: 7

```
Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
```

```
                385                 390                 395                 400
His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
                420                 425                 430

Phe Ile Ala Thr Asp Ile Asp Phe Arg Gly Gln Tyr Tyr Lys Tyr Ile
                435                 440                 445

Pro Phe Gly Ser Gly Arg Arg Ser Cys Pro Gly Met Thr Tyr Ala Leu
450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
                500                 505                 510

Ala Pro Glu Leu Tyr
                515

<210> SEQ ID NO 8
<211> LENGTH: 517
<212> TYPE: PRT
<213> ORGANISM: Nicotiana tabacum

<400> SEQUENCE: 8

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
                35                  40                  45

His Phe Asn Asp Asp Gly Asp Asp Arg Pro Leu Ala Arg Lys Leu Gly
            50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
            130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
                195                 200                 205

Val Glu Arg Phe Lys Lys Ala Phe Lys Asp Phe Met Ile Leu Ser Met
            210                 215                 220

Glu Phe Val Leu Trp Asp Ala Phe Pro Ile Pro Leu Phe Lys Trp Val
225                 230                 235                 240
```

```
Asp Phe Gln Gly His Val Lys Ala Met Lys Arg Thr Phe Lys Asp Ile
            245                 250                 255

Asp Ser Val Phe Gln Asn Trp Leu Glu Glu His Ile Asn Lys Arg Glu
        260                 265                 270

Lys Met Glu Val Asn Ala Glu Gly Asn Glu Gln Asp Phe Ile Asp Val
    275                 280                 285

Val Leu Ser Lys Met Ser Asn Glu Tyr Leu Gly Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Tyr Tyr Lys Tyr Ile
        435                 440                 445

Pro Phe Gly Ser Gly Arg Arg Ser Cys Pro Gly Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 9
<211> LENGTH: 1554
<212> TYPE: DNA
<213> ORGANISM: Nicotiana tabacum

<400> SEQUENCE: 9
atggtttctc ccgtagaagc catcgtagga ctagtaactc ttacacttct cttctacttc      60
atacggacca aaaatctca aaaccttca aaaccattac caccgaaaat ccccggaggg       120
tggccggtaa tcggccatct tttctatttc gatgacgaca gcgacgaccg tccattagca     180
cgaaaactcg gagacttagc tgacaaatac ggcccggttt tcactttcg gctaggcctt      240 ccgcttgtgt tagttgtaag cagttacgaa gctataaaag actgcttctc tacaaatgat    300 gccatttct ccaatcgtcc agcttttctt tatggcgaat accttggcta caataatgcc     360
atgctatttt tgacaaaata cggaccttac tggcgaaaaa atagaaaatt agtcattcag    420
gaagttctct gtgctagtcg tctcgaaaaa ttgaagcacg tgagatttgg tgaaattcag    480
acgagcatta agaatttata cactcgaatt gatggaaatt cgagtacgat aaatctaacc   540
```

-continued

```
gattggttag aagaattgaa ttttggtctg atcgtgaaaa tgatcgctgg gaaaaattat    600
gaatccggta aaggagatga acaagtggag agatttagga aagcgtttaa ggattttata    660
atttatcaa tggagtttgt gttatgggat gctttccaa ttccattgtt caaatgggtg     720
gattttcaag gccatgttaa ggccatgaaa aggacattta aggatataga ttctgttttt    780
cagaattggt tagaggaaca tgtcaagaaa aagaaaaaa tggaggttaa tgcagaagga    840
aatgaacaag atttcattga tgtggtgctt tcaaaaatga gtaatgaata tcttgatgaa    900
ggctactctc gtgatactgt cataaaagca acagtgttta gtttagtctt ggatgctgcg    960
gacacagttg ctcttcacat gaattgggga atggcattat tgataaacaa tcaacatgcc   1020
ttgaagaaag cgcaagaaga gatagataaa aaagttggta aggatagatg ggtagaagag   1080
agtgatatta aggatttggt atacctccaa actattgtta agaagtgtt acgattatat    1140
ccaccgggac ctttattagt accccatgaa aatgtagagg attgtgttgt tagtggatat   1200
cacattccta aagggactag actattcgcg aacgttatga aattacagcg cgatcctaaa   1260
ctctggtcaa atcctgataa gttcgatcca gagagatttt tcgctgctga tattgacttt   1320
cgtggtcaac actatgagtt tatcccattt ggttctggaa gacgatcttg tccggggatg   1380
acttatgcaa tgcaagtgga acacctaaca atcgcacact tgatccaggg tttcaattac   1440
aaaactccaa atgacgagcc cttggatatg aaggaaggtg caggattaac tatacgtaag   1500
gtaaatccta tagaagtggt aattacgcct cgcctgacac ctgagcttta ttaa        1554
```

<210> SEQ ID NO 10
<211> LENGTH: 517
<212> TYPE: PRT
<213> ORGANISM: Nicotiana tabacum

<400> SEQUENCE: 10

```
Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Ser Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
        115                 120                 125

Pro Tyr Trp Arg Lys Asn Arg Lys Leu Val Ile Gln Glu Val Leu Cys
    130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190
```

```
Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
        210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu His Val Lys Lys Glu
        260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Asp Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
            325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
            355                 360                 365

Leu Gln Thr Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
        435                 440                 445

Pro Phe Gly Ser Gly Arg Arg Ser Cys Pro Gly Met Thr Tyr Ala Met
450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
            485                 490                 495

Thr Ile Arg Lys Val Asn Pro Ile Glu Val Val Ile Thr Pro Arg Leu
            500                 505                 510

Thr Pro Glu Leu Tyr
        515

<210> SEQ ID NO 11
<211> LENGTH: 1554
<212> TYPE: DNA
<213> ORGANISM: Nicotiana tabacum
<220> FEATURE:
<221> NAME/KEY: Mutation
<222> LOCATION: (1141)..(1141)
<223> OTHER INFORMATION: C to T

<400> SEQUENCE: 11
atggtttctc ccgtagaagc catcgtagga ctagtaactc ttacacttct cttctacttc    60
atacggacca aaaatctca aaaaccttca aaaccattac caccgaaaat ccccggaggg   120
```

-continued

| | |
|---|---|
| tggccggtaa tcggccatct tttctatttc gatgacgaca gcgacgaccg tccattagca | 180 |
| cgaaaactcg gagacttagc tgacaaatac ggcccggttt tcactttcg gctaggcctt | 240 |
| ccgcttgtgt tagttgtaag cagttacgaa gctataaaag actgcttctc tacaaatgat | 300 |
| gccattttct ccaatcgtcc agcttttctt tatggcgaat accttggcta caataatgcc | 360 |
| atgctatttt tgacaaaata cggaccttac tggcgaaaaa atagaaaatt agtcattcag | 420 |
| gaagttctct gtgctagtcg tctcgaaaaa ttgaagcacg tgagatttgg tgaaattcag | 480 |
| acgagcatta agaatttata cactcgaatt gatggaaatt cgagtacgat aaatctaacc | 540 |
| gattggttag aagaattgaa ttttggtctg atcgtgaaaa tgatcgctgg gaaaaattat | 600 |
| gaatccggta aaggagatga acaagtggag agatttagga aagcgtttaa ggatttata | 660 |
| attttatcaa tggagtttgt gttatgggat gcttttccaa ttccattgtt caaatgggtg | 720 |
| gattttcaag gccatgttaa ggccatgaaa aggacattta aggatataga ttctgtttt | 780 |
| cagaattggt tagaggaaca tgtcaagaaa aagaaaaaa tggaggttaa tgcagaagga | 840 |
| aatgaacaag atttcattga tgtggtgctt tcaaaaatga gtaatgaata tcttgatgaa | 900 |
| ggctactctc gtgatactgt cataaaagca acagtgttta gtttagtctt ggatgctgcg | 960 |
| gacacagttg ctcttcacat gaattgggga atggcattat tgataaacaa tcaacatgcc | 1020 |
| ttgaagaaag cgcaagaaga gatagataaa aaagttggta aggatagatg ggtagaagag | 1080 |
| agtgatatta aggatttggt atacctccaa actattgtta agaagtgtt acgattatat | 1140 |
| tcaccgggac ctttattagt accccatgaa aatgtagagg attgtgttgt tagtggatat | 1200 |
| cacattccta aagggactag actattcgcg aacgttatga aattacagcg cgatcctaaa | 1260 |
| ctctggtcaa atcctgataa gttcgatcca gagagatttt tcgctgctga tattgacttt | 1320 |
| cgtggtcaac actatgagtt tatcccattt ggttctggaa gacgatcttg tccggggatg | 1380 |
| acttatgcaa tgcaagtgga cacctaaca atcgcacact tgatccaggg tttcaattac | 1440 |
| aaaactccaa atgacgagcc cttggatatg aaggaaggtg caggattaac tatacgtaag | 1500 |
| gtaaatccta tagaagtggt aattacgcct cgcctgacac ctgagcttta ttaa | 1554 |

<210> SEQ ID NO 12
<211> LENGTH: 571
<212> TYPE: PRT
<213> ORGANISM: Nicotiana tabacum

<400> SEQUENCE: 12

```
Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Ser Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
        115                 120                 125
```

-continued

```
Pro Tyr Trp Arg Lys Asn Arg Lys Leu Val Ile Gln Glu Val Leu Cys
        130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
        355                 360                 365

Leu Gln Thr Ile Val Lys Glu Val Leu Arg Leu Tyr Ser Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
        435                 440                 445

Pro Phe Gly Ser Gly Arg Arg Ser Cys Pro Gly Met Thr Tyr Ala Met
450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
            500                 505                 510

Thr Pro Glu Leu Tyr Gly Thr Ala Ala Ala Thr Cys Cys Thr Ala Thr
        515                 520                 525

Ala Gly Ala Ala Gly Thr Gly Gly Thr Ala Ala Thr Ala Cys Gly
530                 535                 540
```

-continued

```
Cys Cys Thr Cys Gly Cys Cys Thr Gly Ala Cys Ala Cys Cys Thr Gly
545                 550                 555                 560

Ala Gly Cys Thr Thr Thr Ala Thr Thr Ala Ala
                565             570
```

TOBACCO INBRED AND HYBRID PLANTS AND TOBACCO PRODUCTS MADE THEREOF

CROSS REFERENCE TO RELATED APPLICATIONS

This application claims benefit under 35 U.S.C. §119(e) of U.S. provisional application Ser. No. 61/946,978, filed Mar. 3, 2014, U.S. provisional application Ser. No. 61/946,981, filed Mar. 3, 2014, U.S. provisional application Ser. No. 61/946,983, filed Mar. 3, 2014, U.S. provisional application Ser. No. 61/946,988, filed Mar. 3, 2014, U.S. provisional application Ser. No. 61/978,253, filed Apr. 11, 2014, U.S. provisional application Ser. No. 61/978,267, filed Apr. 11, 2014, U.S. provisional application Ser. No. 61/978,305, filed Apr. 11, 2014, and U.S. provisional application Ser. No. 61/978,312, filed Apr. 11, 2014, all of which are incorporated herein by reference in their entireties.

INCORPORATION OF SEQUENCE LISTING

The Sequence Listing is hereby incorporated by reference in its entirety, including the file named P34119US02.txt, which is 38,330 bytes in size and was generated on Feb. 23, 2015, which is likewise herein incorporated by reference in its entirety.

FIELD

The present disclosure provides tobacco inbred plants Banket A1 SRC, CMS Banket A1 SRC, NC 2000 SRC, CMS NC 2000 SRC, NC 2002 SRC, CMS NC 2002 SRC, Burley 21 SRC, and CMS Burley 21 SRC. The present disclosure also provides parts of such plants and cured tobacco and tobacco products made from those parts. The present disclosure also includes progenies of the provided plants including hybrids.

BACKGROUND

Tobacco (*Nicotiana tabacum* L.) is an important commercial crop in the United States as well as in other countries. In tobacco plants, N-demethylation of nicotine results in nornicotine, a secondary alkaloid known to be a precursor for formation of N-Nitrosonornicotine ("NNN") in cured leaves. NNN is an undesired component of cured leaves.

The predominant alkaloid found in commercial tobacco varieties is nicotine, typically accounting for 90-95% of the total alkaloid pool. The remaining alkaloid fraction is comprised primarily of three additional pyridine alkaloids: nornicotine, anabasine, and anatabine. Nornicotine is generated directly from nicotine through the activity of the enzyme nicotine N-demethylase. Nornicotine usually represents less than 5% of the total pyridine alkaloid pool, but through a process termed "conversion," tobacco plants that initially produce very low amounts of nornicotine give rise to progeny that metabolically "convert" a large percentage of leaf nicotine to nornicotine. In tobacco plants that have genetically converted (termed "converters"), the great majority of nornicotine production occurs during the senescence and curing of the mature leaf (Wernsman and Matzinger (1968), *Tob. Sci.,* 12:226-228). Burley tobaccos are particularly prone to genetic conversion, with rates as high as 20% per generation observed in some cultivars.

During the curing and processing of the tobacco leaf, a portion of the nornicotine is metabolized to the compound NNN, a tobacco-specific nitrosamine (TSNA) that has been asserted to be carcinogenic in laboratory animals (Hecht and Hoffmann (1990), *Cancer Surveys,* 8:273-294; Hoffmann et al. (1994), *J. Toxicol. Environ. Health,* 41:1-52; Hecht (1998), *Chem. Res. Toxicol.,* 11:559-603). In flue-cured tobaccos, TSNAs are found to be predominantly formed through the reaction of alkaloids with the minute amounts of nitrogen oxides present in combustion gases formed by the direct-fired heating systems found in traditional curing barns (Peele and Gentry (1999), "Formation of Tobacco-specific Nitrosamines in Flue-cured Tobacco," CORESTA Meeting, Agro-Phyto Groups, Suzhou, China). Retrofitting these curing barns with heat-exchangers virtually eliminated the mixing of combustion gases with the curing air and dramatically reduced the formation of TSNAs in tobaccos cured in this manner (Boyette and Hamm (2001), *Rec. Adv. Tob. Sci.,* 27:17-22.). In contrast, in the air-cured Burley tobaccos, TSNA formation proceeds primarily through reaction of tobacco alkaloids with nitrite, a process catalyzed by leaf-borne microbes (Bush et al. (2001), *Rec. Adv. Tob. Sci.,* 27:23-46). Thus far, attempts to reduce TSNAs through modification of curing conditions while maintaining acceptable quality standards have not proven to be successful for the air-cured tobaccos.

SUMMARY

In an aspect, the present disclosure includes a seed of tobacco cultivar Banket A1 SRC, a representative sample seed of the cultivar having been deposited with the American Type Culture Collection (ATCC) under ATCC Accession No. PTA-121043.

In another aspect, the present disclosure includes a tobacco plant, or part thereof, produced by growing the seed of tobacco cultivar Banket A1 SRC, a representative sample seed of the cultivar having been deposited with the ATCC under ATCC Accession No. PTA-121043.

In a further aspect, the present disclosure includes a harvested leaf, or part thereof, of a tobacco plant, or part thereof, produced by growing the seed of tobacco cultivar Banket A1 SRC, a representative sample seed of the cultivar having been deposited with the ATCC under ATCC Accession No. PTA-121043.

In an aspect, the present disclosure includes a harvested leaf, or part thereof, of a tobacco plant, produced by growing the seed of tobacco cultivar Banket A1 SRC, a representative sample seed of the cultivar having been deposited with the ATCC under ATCC Accession No. PTA-121043, where the leaf has a reduced amount of nornicotine and/or N'-nitrosonornicotine (NNN).

In an aspect, the present disclosure includes a harvested leaf, or part thereof, produced by growing the seed of tobacco cultivar Banket A1 SRC, a representative sample seed of the cultivar having been deposited with the ATCC under ATCC Accession No. PTA-121043, where the leaf has a reduced amount of nornicotine and/or N'-nitrosonornicotine (NNN), where the reduced amount of nornicotine and/or N'-nitrosonomicotine (NNN) is reduced in a smoke stream produced from the leaf.

In a further aspect, the present disclosure includes a tobacco product, prepared from a tobacco plant, or part thereof, produced by growing the seed of tobacco cultivar Banket A1 SRC, a representative sample seed of the cultivar having been deposited with the ATCC under ATCC Accession No. PTA-121043, where the product is selected from the group consisting of pipe tobacco, cigar tobacco, cigarette tobacco, chewing tobacco, leaf tobacco, shredded tobacco, cut tobacco and any combination thereof.

In an aspect, the present disclosure includes a tobacco product, prepared from a tobacco plant, or part thereof, produced by growing the seed of tobacco cultivar Banket A1 SRC, a representative sample seed of the cultivar having been deposited with the ATCC under ATCC Accession No. PTA-121043, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar Banket A1 SRC, a representative sample seed of the cultivar having been deposited with the ATCC under ATCC Accession No. PTA-121043, where the product is selected from the group consisting of a cigarillo, a non-ventilated recess filter cigarette, a vented recess filter cigarette, a cigar, snuff, and chewing tobacco, and where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar Banket A1 SRC, a representative sample seed of the cultivar having been deposited with the ATCC under ATCC Accession No. PTA-121043, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and second product comprises a reduced amount of nornicotine and/or N'-nitrosonornicotine (NNN).

In an aspect, the present disclosure includes a part of a tobacco plant, produced by growing the seed of tobacco cultivar Banket A1 SRC, a representative sample seed of the cultivar having been deposited with the ATCC under ATCC Accession No. PTA-121043, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present disclosure includes a tissue culture produced from a protoplast or cell from a tobacco plant, or part thereof, produced by growing the seed of tobacco cultivar Banket A1 SRC, a representative sample seed of the cultivar having been deposited with the ATCC under ATCC Accession No. PTA-121043, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar Banket A1 SRC, a representative sample seed of the cultivar having been deposited with the ATCC under ATCC Accession No. PTA-121043, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar Banket A1 SRC.

In an aspect, the present disclosure includes an $F_1$ progeny plant of tobacco cultivar Banket A1 SRC, a representative sample seed of the cultivar having been deposited with the ATCC under ATCC Accession No. PTA-121043.

In another aspect, the present disclosure includes an $F_1$ progeny plant of tobacco cultivar Banket A1 SRC, a representative sample seed of the cultivar having been deposited with the ATCC under ATCC Accession No. PTA-121043, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is a tobacco plant produced by growing the seed of tobacco cultivar Banket A1 SRC, a representative sample seed of the cultivar having been deposited with the ATCC under ATCC Accession No. PTA-121043, where at least one tobacco plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Banket A1 SRC, a representative sample seed of the cultivar having been deposited with the ATCC under ATCC Accession No. PTA-121043.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Banket A1 SRC, a representative sample seed of the cultivar having been deposited with the ATCC under ATCC Accession No. PTA-121043, where the plant of tobacco cultivar Banket A1 SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Banket A1 SRC, a representative sample seed of the cultivar having been deposited with the ATCC under ATCC Accession No. PTA-121043, where the plant of tobacco cultivar Banket A1 SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Banket A1 SRC, a representative sample seed of the cultivar having been deposited with the ATCC under ATCC Accession No. PTA-121043, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar Banket A1 SRC, a representative sample seed of the cultivar having been deposited with the ATCC under ATCC Accession No. PTA-121043, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar Banket A1 SRC, a representative sample seed of the cultivar having been deposited with the ATCC under ATCC Accession No. PTA-121043, and where at least one tobacco plant is cytoplasmic male sterile (CMS).

In an aspect, the present disclosure also includes a harvested leaf of an $F_1$ progeny plant produced by growing a seed produced by crossing two tobacco plants and harvesting the resultant tobacco seed, where at least one tobacco plant is a tobacco plant produced by growing the seed of tobacco cultivar Banket A1 SRC, a representative sample seed of the cultivar having been deposited with the ATCC under ATCC Accession No. PTA-121043, where at least one tobacco plant is cytoplasmic male sterile (CMS).

In another aspect, the present disclosure further includes a harvested leaf of an $F_1$ progeny plant having a reduced amount of nornicotine and/or N'-nitrosonornicotine (NNN) produced by growing a seed produced by a method of comprising crossing two tobacco plants and harvesting the resultant tobacco seed, where at least one tobacco plant is a tobacco plant produced by growing the seed of tobacco cultivar Banket A1 SRC, a representative sample seed of the cultivar having been deposited with the ATCC under ATCC Accession No. PTA-121043, where at least one tobacco plant is cytoplasmic male sterile (CMS).

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar Banket A1 SRC, a representative sample seed of the cultivar having been deposited with the ATCC under ATCC Accession No. PTA-121043, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing an $F_1$ progeny seed produced by a method comprising crossing two tobacco plants and harvesting the resultant tobacco seed, where at least one tobacco plant is produced by growing a seed of tobacco cultivar Banket A1 SRC, a representative sample seed of the cultivar having been deposited with the ATCC under ATCC Accession No. PTA-121043, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present disclosure further includes a tobacco product prepared from an $F_1$ progeny tobacco plant, or part thereof, where the plant or part thereof is produced by growing an $F_1$ progeny seed produced by a method comprising crossing two tobacco plants and harvesting the resultant tobacco seed, where at least one tobacco plant is produced by growing a seed of tobacco cultivar Banket A1 SRC, a representative sample seed of the cultivar having been deposited with the ATCC under ATCC Accession No. PTA-121043, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco.

In another aspect, the present disclosure includes a seed of tobacco cultivar CMS Banket A1 SRC, a representative sample seed of the cultivar having been deposited with the ATCC under ATCC Accession No. PTA-121054.

In an aspect, the present disclosure includes a tobacco plant, or part thereof, produced by growing the seed of tobacco cultivar CMS Banket A1 SRC, a representative sample seed of the cultivar having been deposited with the ATCC under ATCC Accession No. PTA-121054.

In another aspect, the present disclosure includes a harvested leaf, or part thereof, of a tobacco plant, or part thereof, produced by growing the seed of tobacco cultivar CMS Banket A1 SRC, a representative sample seed of the cultivar having been deposited with the ATCC under ATCC Accession No. PTA-121054.

In an aspect, the present disclosure includes a harvested leaf, or part thereof, of a tobacco plant, produced by growing the seed of tobacco cultivar CMS Banket A1 SRC, a representative sample seed of the cultivar having been deposited with the ATCC under ATCC Accession No. PTA-121054, where the leaf has a reduced amount of nornicotine and/or N'-nitrosonornicotine (NNN).

In another aspect, the present disclosure includes a harvested leaf, or part thereof, produced by growing the seed of tobacco cultivar CMS Banket A1 SRC, a representative sample seed of the cultivar having been deposited with the ATCC under ATCC Accession No. PTA-121054, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar CMS Banket A1 SRC, a representative sample seed of the cultivar having been deposited with the ATCC under ATCC Accession No. PTA-121054, where the product is selected from the group consisting of pipe tobacco, cigar tobacco, cigarette tobacco, chewing tobacco, leaf tobacco, shredded tobacco, cut tobacco and any combination thereof.

In an aspect, the present disclosure includes a tobacco product, prepared from a tobacco plant, or part thereof, produced by growing the seed of tobacco cultivar CMS Banket A1 SRC, a representative sample seed of the cultivar having been deposited with the ATCC under ATCC Accession No. PTA-121054, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar CMS Banket A1 SRC, a representative sample seed of the cultivar having been deposited with the ATCC under ATCC Accession No. PTA-121054, where the product is selected from the group consisting of a cigarillo, a non-ventilated recess filter cigarette, a vented recess filter cigarette, a cigar, snuff, and chewing tobacco where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar CMS Banket A1 SRC, a representative sample seed of the cultivar having been deposited with the ATCC under ATCC Accession No. PTA-121054, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and/or the second product comprises a reduced amount of nornicotine and/or N'-nitrosonornicotine (NNN).

In an aspect, the present disclosure includes a part of a tobacco plant, produced by growing the seed of tobacco cultivar CMS Banket A1 SRC, a representative sample seed of the cultivar having been deposited with the ATCC under ATCC Accession No. PTA-121054, where the part is selected from the group consisting of leaf, pollen, ovule, embryo, cotyledon, hypocotyl, meristematic cell, protoplast, root, root tip, pistil, anther, flower, shoot, stem, pod, and petiole.

In another aspect, the present disclosure includes a tissue culture produced from a protoplast or cell from a tobacco plant, or part thereof, produced by growing the seed of tobacco cultivar CMS Banket A1 SRC, a representative sample seed of the cultivar having been deposited with the ATCC under ATCC Accession No. PTA-121054, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar CMS Banket A1 SRC, a representative sample seed of the cultivar having been deposited with the ATCC under ATCC Accession No. PTA-121054, where the cell or protoplast of the tissue culture can be produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar CMS Banket A1 SRC.

In an aspect, the present disclosure includes an $F_1$ progeny plant of tobacco cultivar CMS Banket A1 SRC, a representative sample seed of the cultivar having been deposited with the ATCC under ATCC Accession No. PTA-121054.

In another aspect, the present disclosure includes an $F_1$ progeny plant of tobacco cultivar CMS Banket A1 SRC, a representative sample seed of the cultivar having been deposited with the ATCC under ATCC Accession No. PTA-121054, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is cytoplasmic male sterile (CMS), where the cytoplasmic male sterile plant is a plant of tobacco cultivar CMS Banket A1 SRC, a representative sample seed of the cultivar having been deposited with the ATCC under ATCC Accession No. PTA-121054.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS Banket A1 SRC, a representative sample seed of the cultivar having been deposited with the ATCC under ATCC Accession No. PTA-121054.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS Banket A1 SRC, a representative sample seed of the cultivar having been deposited with the ATCC under ATCC Accession No. PTA-121054, where the plant of tobacco cultivar CMS Banket A1 SRC is the female parent.

In another aspect, the present disclosure includes a method for producing a tobacco seed comprising crossing two tobacco plants and harvesting the resultant tobacco seed, where at least one tobacco plant is cytoplasmic male sterile (CMS), where the cytoplasmic male sterile plant is a plant of tobacco cultivar CMS Banket A1 SRC, a representative sample seed of the cultivar having been deposited with the ATCC under ATCC Accession No. PTA-121054.

In an aspect, the present disclosure also includes a container of $F_1$ progeny seeds produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Banket A1 SRC, a representative sample seed of the cultivar having been deposited with the ATCC under ATCC Accession No. PTA-121054.

In an aspect, the present disclosure includes an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Banket A1 SRC, a representative sample seed of the cultivar having been deposited with the ATCC under ATCC Accession No. PTA-121054.

In an aspect, the present disclosure also includes a harvested leaf of an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Banket A1 SRC, a representative sample seed of the cultivar having been deposited with the ATCC under ATCC Accession No. PTA-121054.

In another aspect, the present disclosure further includes a harvested leaf of an $F_1$ progeny plant having a reduced amount of nornicotine and/or N'-nitrosonornicotine (NNN) produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Banket A1 SRC, a representative sample seed of the cultivar having been deposited with the ATCC under ATCC Accession No. PTA-121054.

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Banket A1 SRC, a representative sample seed of the cultivar having been deposited with the ATCC under ATCC Accession No. PTA-121054.

In an aspect, the present disclosure includes a tobacco product prepared from an $F_1$ progeny tobacco plant, or part thereof, where the plant or part thereof is produced by growing an $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Banket A1 SRC, a representative sample seed of the cultivar having been deposited with the ATCC under ATCC Accession No. PTA-121054, and where the tobacco product is selected from the group consisting of pipe tobacco, cigar tobacco, cigarette tobacco, chewing tobacco, leaf tobacco, shredded tobacco, cut tobacco and any combination thereof.

In an aspect, the present disclosure further includes a tobacco product prepared from an $F_1$ progeny tobacco plant, or part thereof, where the plant or part thereof is produced by growing an $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Banket A1 SRC, a representative sample seed of the cultivar having been deposited with the ATCC under ATCC Accession No. PTA-121054, and where the tobacco product is selected from the group consisting of a cigarillo, a non-ventilated recess filter cigarette, a vented recess filter cigarette, a cigar, snuff, and chewing tobacco.

In an aspect, the present disclosure further includes a tobacco product prepared from an $F_1$ progeny tobacco plant, or part thereof, where the plant or part thereof is produced by growing an $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Banket A1 SRC, a representative sample seed of the cultivar having been deposited with the ATCC under ATCC Accession No. PTA-121054, and where the tobacco product is selected from the group consisting of a cigarillo, a non-ventilated recess filter cigarette, a vented recess filter cigarette, a cigar, snuff, and chewing tobacco, and further where the product has a reduced amount of nornicotine and/or N'-nitrosonornicotine (NNN).

In an aspect, the present disclosure includes a method for producing a tobacco seed comprising crossing two tobacco plants and harvesting the resultant tobacco seed, where at least one tobacco plant is cytoplasmic male sterile, where the cytoplasmic male sterile plant is a plant of tobacco cultivar CMS Banket A1 SRC, a representative sample seed of the cultivar having been deposited with the ATCC under ATCC Accession No. PTA-121054.

In an aspect, the present disclosure includes a method of vegetatively propagating a plant of a tobacco cultivar comprising the steps of (a) collecting tissue capable of being propagated from a plant of a tobacco cultivar Banket A1 SRC, a representative sample seed of the cultivar having been deposited with the ATCC under ATCC Accession No. PTA-121043 or CMS Banket A1 SRC, a representative sample seed of the cultivar having been deposited with the ATCC under ATCC Accession No. PTA-121054; (b) cultivating the tissue to obtain a proliferated shoot; and (c) rooting the proliferated shoots to obtain a rooted plantlet.

In an aspect, the present disclosure includes a method of vegetatively propagating a plant of a tobacco cultivar comprising the steps of (a) collecting tissue capable of being propagated from a plant of a tobacco cultivar Banket A1 SRC, a representative sample seed of the cultivar having been deposited with the ATCC under ATCC Accession No. PTA-121043 or CMS Banket A1 SRC, a representative sample seed of the cultivar having been deposited with the ATCC under ATCC Accession No. PTA-121054; (b) cultivating the tissue to obtain a proliferated shoot; (c) rooting the proliferated shoots to obtain a rooted plantlet; and (d) growing a plant from the rooted plantlet.

In an aspect, the present disclosure includes a method of introducing a desired trait into a tobacco cultivar comprising: (a) crossing a plant of a first tobacco cultivar Banket A1 SRC, a representative sample seed of the cultivar having been deposited with the ATCC under ATCC Accession No. PTA-121043 or CMS Banket A1 SRC, a representative sample seed of the cultivar having been deposited with the ATCC under ATCC Accession No. PTA-121054, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of said first tobacco cultivar, Banket A1 SRC or CMS Banket A1 SRC; and (e) repeating steps (c) and (d) three or more times (e.g., 3, 4, 5, 6, 7, 8, 9, 10, and the like) in succession to produce selected fourth or higher backcross progeny that comprise the desired trait. In additional aspects, steps (c) and (d) can be repeated one or more times (e.g., 1, 2, 3, 4, 5, 6, 7, 8, 9, 10, and the like) in succession to produce second or higher backcross progeny comprising the desired trait.

In an aspect, the present disclosure includes a method of introducing a desired trait into a tobacco cultivar comprising: (a) crossing a plant of a first tobacco cultivar Banket A1 SRC, a representative sample seed of the cultivar having been deposited with the ATCC under ATCC Accession No. PTA-121043, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar Banket A1 SRC, a representative sample seed of the cultivar having been deposited with the ATCC under ATCC Accession No. PTA-121043 to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar, Banket A1 SRC; and (e) repeating steps (c) and (d) three or more times in succession to produce selected fourth or higher backcross progeny that comprise the desired trait, where the trait is cytoplasmic male sterility (CMS). In additional aspects, steps (c) and (d) can be repeated one or more times in succession to produce second or higher backcross progeny comprising the desired trait, where the trait is CMS.

In an aspect, the present disclosure includes a method of introducing a desired trait into a tobacco cultivar comprising: (a) crossing a plant of a first tobacco cultivar Banket A1 SRC, a representative sample seed of the cultivar having been deposited with the ATCC under ATCC Accession No. PTA-121043, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar Banket A1 SRC, a representative sample seed of the cultivar having been deposited with the ATCC under ATCC Accession No. PTA-121043 to produce a backcross $BC_1F_1$ progeny seed; (d) growing the $BC_1F_1$ progeny seed and selecting a backcross $BC_1F_1$ progeny plant comprising the desired trait and the physiological and essentially all of morphological characteristics of the first tobacco cultivar Banket A1 SRC; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens* or *Nicotiana glauca*. In additional aspects, steps (c) and (d) can be repeated one or more times in succession to produce second or higher backcross progeny comprising the desired trait, where the trait is CMS and the CMS trait is obtained from the cytoplasm of *Nicotiana suaveolens* or *Nicotiana glauca*.

In an aspect, the present disclosure includes a method of introducing a desired trait into a tobacco cultivar comprising: (a) crossing a plant of a first tobacco cultivar Banket A1 SRC, a representative sample seed of the cultivar having been deposited with the ATCC under ATCC Accession No. PTA-121043 with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar, Banket A1 SRC to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of tobacco cultivar Banket A1 SRC; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens*, and where the second tobacco plant is CMS Banket A1 SRC. In additional aspects, steps (c) and (d) can be repeated one or more times in succession to produce second or higher backcross progeny comprising the desired trait, where the trait is CMS and the CMS trait is obtained from the cytoplasm of *Nicotiana suaveolens*.

In an aspect, the present disclosure includes a tobacco plant produced by a method comprising introducing a desired trait into a tobacco cultivar comprising: (a) crossing a plant of a first tobacco cultivar Banket A1 SRC, a representative sample seed of the cultivar having been deposited with the ATCC under ATCC Accession No. PTA-121043 or CMS Banket A1 SRC, a representative sample seed of the cultivar having been deposited with the ATCC under ATCC Accession No. PTA-121054, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar Banket A1 SRC or CMS Banket A1 SRC to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar Banket A1 SRC or CMS Banket A1 SRC; and (e) repeating steps (c) and (d) three or more times in succession to produce selected fourth or higher backcross progeny that comprise the desired trait. In additional aspects, steps (c) and (d) can be repeated one or more times in succession to produce second or higher backcross progeny that comprise the desired trait.

In another aspect, the present disclosure includes a method of introducing a desired trait into a tobacco cultivar comprising: (a) crossing a plant of a first tobacco cultivar Banket A1 SRC, a representative sample seed of the cultivar having been deposited with the ATCC under ATCC Accession No. PTA-121043 or CMS Banket A1 SRC, a representative sample seed of the cultivar having been deposited with the ATCC under ATCC Accession No. PTA-121054 with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of the first tobacco cultivar Banket A1 SRC, a representative sample seed of the cultivar having been deposited with the ATCC under ATCC Accession No. PTA-121043 or CMS Banket A1 SRC, a representative sample seed of the cultivar having been deposited with the ATCC under ATCC Accession No. PTA-121054 to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, Banket A1 SRC or CMS Banket A1 SRC; and (e) repeating steps (c) and (d) one or more times in succession to produce a selected second, third, fourth or higher backcross progeny plant that comprises the desired trait and essentially all of the physiological and morphological characteristics of the first tobacco cultivar, Banket A1 SRC or CMS Banket A1 SRC.

In another aspect, the present disclosure includes a method of introducing a desired trait into a tobacco cultivar comprising: (a) crossing a plant of a first tobacco cultivar Banket A1 SRC, a representative sample seed of the cultivar having been deposited with the ATCC under ATCC Accession No. PTA-121043 or CMS Banket A1 SRC, a representative sample seed of the cultivar having been deposited with the ATCC under ATCC Accession No. PTA-121054, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of the first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, Banket A1 SRC or CMS Banket A1 SRC; and (e) repeating steps (c) and (d) one or more times in succession to produce a selected second, third, fourth or higher backcross progeny plant that comprises the desired trait and essentially all of the physiological and morphological characteristics of the first tobacco cultivar, Banket A1 SRC or CMS Banket A1 SRC.

In another aspect, the present disclosure includes a method of introducing a desired trait into a tobacco cultivar comprising: (a) crossing a plant of a first tobacco cultivar Banket A1 SRC, a representative sample seed of the cultivar having been deposited with the ATCC under ATCC Accession No. PTA-121043 or CMS Banket A1 SRC, a representative sample seed of the cultivar having been deposited with the ATCC under ATCC Accession No. PTA-121054, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of the first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, Banket A1 SRC or CMS Banket A1 SRC; and (e) repeating steps (c) and (d) one or more times in succession to produce a selected second, third, fourth or higher backcross progeny plant that comprises the desired trait and essentially all of the physiological and morphological characteristics of the first tobacco cultivar, Banket A1 SRC or CMS Banket A1 SRC, where the plant has a desired trait of disease resistance.

In another aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the second tobacco plant comprises a nucleotide sequence selected from the group consisting of the nucleotide sequence of SEQ ID NO: 1, SEQ ID NO: 2, SEQ ID NO: 11, and any combination thereof.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the second tobacco plant does not have the nucleotide sequence selected from the group consisting of the nucleotide sequence of SEQ ID NO: 1, SEQ ID NO: 2, SEQ ID NO: 11, and any combination thereof, and the third tobacco plant is a tobacco plant comprising a nucleotide sequence selected from the group consisting of the nucleotide sequence of SEQ ID NO: 1, SEQ ID NO: 2, SEQ ID NO: 11, and any combination thereof.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the first tobacco plant comprises the sequence set forth in SEQ ID NO: 1 or SEQ ID NO: 2.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the third tobacco plant is a tobacco plant comprising a nucleotide sequence selected from the group consisting of the nucleotide sequence of SEQ ID NO: 1, SEQ ID NO: 2, SEQ ID NO: 11, and any combination thereof.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the first tobacco plant is a plant of tobacco cultivar Banket A1 SRC, a representative sample seed of the cultivar having been deposited with the ATCC under ATCC Accession No. PTA-121043, or tobacco cultivar CMS Banket A1 SRC, a representative sample seed of the cultivar having been deposited with the ATCC under ATCC Accession No. PTA-121054.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the third tobacco plant is a plant of tobacco cultivar Banket A1 SRC, a representative sample seed of the cultivar having been deposited with the ATCC under ATCC Accession No. PTA-121043, or tobacco cultivar CMS Banket A1 SRC, a representative sample seed of the cultivar having been deposited with the ATCC under ATCC Accession No. PTA-121054.

In another aspect, the present disclosure includes a method of producing a plant of a tobacco cultivar Banket A1 SRC, a representative sample seed of the cultivar having been deposited with the ATCC under ATCC Accession No. PTA-121043 or tobacco cultivar CMS Banket A1 SRC, a representative sample seed of the cultivar having been deposited with the ATCC under ATCC Accession No. PTA-121054 comprising at least one (e.g., 1, 2, 3, 4, 5, 6, 7, 8, and the like) additional desired trait comprising the steps of: (a) collecting tissue capable of being propagated from a plant of a tobacco cultivar Banket A1 SRC, a representative sample seed of the cultivar having been deposited with the ATCC under ATCC Accession No. PTA-121043 or CMS Banket A1 SRC, a representative sample seed of the cultivar having been deposited with the ATCC under ATCC Accession No. PTA-121054; and (b) introducing a at least one transgene (nucleic acid construct) conferring at least one desired trait into the tissue.

In another aspect, the present disclosure includes a method of producing an herbicide resistant tobacco plant comprising transforming a tobacco plant, or part thereof, produced by growing a seed of tobacco cultivar Banket A1 SRC, a representative sample seed of the cultivar having been deposited with the ATCC under ATCC Accession No. PTA-121043 or tobacco cultivar CMS Banket A1 SRC, a representative sample seed of the cultivar having been deposited with the ATCC under ATCC Accession No. PTA-121054 with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present disclosure includes an herbicide resistant tobacco plant produced by a method comprising transforming a tobacco plant, or part thereof, produced by growing a seed of a tobacco cultivar Banket A1 SRC, a representative sample seed of the cultivar having been deposited with the ATCC under ATCC Accession No. PTA-121043 or CMS Banket A1 SRC, a representative sample seed of the cultivar having been deposited with the ATCC under ATCC Accession No. PTA-121054 with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present disclosure includes a method of producing a pest and/or insect resistant tobacco plant where the method comprises transforming a tobacco plant produced by growing a seed of tobacco cultivar Banket A1 SRC, a representative sample seed of the cultivar having been deposited with the ATCC under ATCC Accession No. PTA-121043 or tobacco cultivar CMS Banket A1 SRC, a representative sample seed of the cultivar having been deposited with the ATCC under ATCC Accession No. PTA-121054, with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of tobacco cultivar Banket A1 SRC, a representative sample seed of the cultivar having been deposited with the ATCC under ATCC Accession No. PTA-121043 or tobacco cultivar CMS Banket A1 SRC, a representative sample seed of the cultivar having been deposited with the ATCC under ATCC Accession No. PTA-121054, with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of tobacco cultivar Banket A1 SRC, a representative sample seed of the cultivar having been deposited with the ATCC under ATCC Accession No. PTA-121043 or tobacco cultivar CMS Banket A1 SRC, a representative sample seed of the cultivar having been deposited with the ATCC under ATCC Accession No. PTA-121054, with at least one transgene (nucleic acid construct) that confers pest and/or insect resistance, where the transgene (nucleic acid construct) encodes a *Bacillus thuringiensis* (BT) endotoxin.

In another aspect, the present disclosure includes a method of producing a disease resistant tobacco plant, the method comprising transforming a tobacco plant produced by growing a seed of tobacco cultivar Banket A1 SRC, a representative sample seed of the cultivar having been deposited with the ATCC under ATCC Accession No. PTA-121043 or tobacco cultivar CMS Banket A1 SRC, a representative sample seed of the cultivar having been deposited with the ATCC under ATCC Accession No. PTA-121054 with at least one transgene (nucleic acid construct) that confers disease resistance.

In a further aspect, the present disclosure includes a disease resistant tobacco plant produced by transforming a tobacco plant produced by growing a seed of tobacco cultivar Banket A1 SRC, a representative sample seed of the cultivar having been deposited with the ATCC under ATCC Accession No. PTA-121043 or tobacco cultivar CMS Banket A1 SRC, a representative sample seed of the cultivar having been deposited with the ATCC under ATCC Accession No. PTA-121054 with at least one transgene (nucleic acid construct) that confers disease resistance.

In an aspect, the present disclosure includes a seed of tobacco cultivar NC 2000 SRC, a representative sample seed of the cultivar having been deposited with the American Type Culture Collection (ATCC) under ATCC Accession No. PTA-121053.

In another aspect, the present disclosure includes a tobacco plant, or part thereof, produced by growing the seed of tobacco cultivar NC 2000 SRC, a representative sample seed of the cultivar having been deposited with the ATCC under ATCC Accession No. PTA-121053.

In a further aspect, the present disclosure includes a harvested leaf, or part thereof, of a tobacco plant, or part thereof, produced by growing the seed of tobacco cultivar NC 2000 SRC, a representative sample seed of the cultivar having been deposited with the ATCC under ATCC Accession No. PTA-121053.

In an aspect, the present disclosure includes a harvested leaf, or part thereof, of a tobacco plant, produced by growing the seed of tobacco cultivar NC 2000 SRC, a representative sample seed of the cultivar having been deposited with the ATCC under ATCC Accession No. PTA-121053, where the leaf has a reduced amount of nornicotine and/or N'-nitrosonornicotine (NNN).

In an aspect, the present disclosure includes a harvested leaf, or part thereof, produced by growing the seed of tobacco cultivar NC 2000 SRC, a representative sample seed of the cultivar having been deposited with the ATCC under ATCC Accession No. PTA-121053, where the leaf has a reduced amount of nornicotine and/or N-nitrosonomicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar NC 2000 SRC, a representative sample seed of the cultivar having been deposited with the ATCC under ATCC Accession No. PTA-121053, where the product is selected from the group consisting of pipe tobacco, cigar tobacco, cigarette tobacco, chewing tobacco, leaf tobacco, shredded tobacco, cut tobacco and any combination thereof.

In an aspect, the present disclosure includes a tobacco product, prepared from a tobacco plant, or part thereof, produced by growing the seed of tobacco cultivar NC 2000 SRC, a representative sample seed of the cultivar having been deposited with the ATCC under ATCC Accession No. PTA-121053, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar NC 2000 SRC, a representative sample seed of the cultivar having been deposited with the ATCC under ATCC Accession No. PTA-121053, where the product is selected from the group consisting of a cigarillo, a non-ventilated recess filter cigarette, a vented recess filter cigarette, a cigar, snuff, and chewing tobacco, and where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar NC 2000 SRC, a representative sample seed of the cultivar having been deposited with the ATCC under ATCC Accession No. PTA-121053, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and second product comprises a reduced amount of nornicotine and/or N'-nitrosonornicotine (NNN).

In an aspect, the present disclosure includes a part of a tobacco plant, produced by growing the seed of tobacco cultivar NC 2000 SRC, a representative sample seed of the cultivar having been deposited with the ATCC under ATCC Accession No. PTA-121053, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present disclosure includes a tissue culture produced from a protoplast or cell from a tobacco plant, or part thereof, produced by growing the seed of tobacco cultivar NC 2000 SRC, a representative sample seed of the cultivar having been deposited with the ATCC under ATCC Accession No. PTA-121053, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar NC 2000 SRC, a representative sample seed of the cultivar having been deposited with the ATCC under ATCC Accession No. PTA-121053, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar NC 2000 SRC.

In an aspect, the present disclosure includes an $F_1$ progeny plant of tobacco cultivar NC 2000 SRC, a representative sample seed of the cultivar having been deposited with the ATCC under ATCC Accession No. PTA-121053.

In another aspect, the present disclosure includes an $F_1$ progeny plant of tobacco cultivar NC 2000 SRC, a representative sample seed of the cultivar having been deposited with the ATCC under ATCC Accession No. PTA-121053, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is a tobacco plant produced by growing the seed of tobacco cultivar NC 2000 SRC, a representative sample seed of the cultivar having been deposited with the ATCC under ATCC Accession No. PTA-121053, where at least one tobacco plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC 2000 SRC, a representative sample seed of the cultivar having been deposited with the ATCC under ATCC Accession No. PTA-121053.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC 2000 SRC, a representative sample seed of the cultivar having been deposited with the ATCC under ATCC Accession No. PTA-121053, where the plant of tobacco cultivar NC 2000 SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC 2000 SRC, a representative sample seed of the cultivar having been deposited with the ATCC under ATCC Accession No. PTA-121053, where the plant of tobacco cultivar NC 2000 SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC 2000 SRC, a representative sample seed of the cultivar having been deposited with the ATCC under ATCC Accession No. PTA-121053, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar NC 2000 SRC, a representative sample seed of the cultivar having been deposited with the ATCC under ATCC Accession No. PTA-121053, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar NC 2000 SRC, a representative sample seed of the cultivar having been deposited with the ATCC under ATCC Accession No. PTA-121053, and where at least one tobacco plant is cytoplasmic male sterile (CMS).

In an aspect, the present disclosure also includes a harvested leaf of an $F_1$ progeny plant produced by growing a seed produced by crossing two tobacco plants and harvesting the resultant tobacco seed, where at least one tobacco plant is a tobacco plant produced by growing the seed of tobacco cultivar NC 2000 SRC, a representative sample seed of the cultivar having been deposited with the ATCC under ATCC Accession No. PTA-121053, where at least one tobacco plant is cytoplasmic male sterile (CMS).

In another aspect, the present disclosure further includes a harvested leaf of an $F_1$ progeny plant having a reduced amount of nornicotine and/or N'-nitrosonornicotine (NNN) produced by growing a seed produced by a method of comprising crossing two tobacco plants and harvesting the resultant tobacco seed, where at least one tobacco plant is a tobacco plant produced by growing the seed of tobacco cultivar NC 2000 SRC, a representative sample seed of the cultivar having been deposited with the ATCC under ATCC Accession No. PTA-121053, where at least one tobacco plant is cytoplasmic male sterile (CMS).

In an aspect, the present disclosure also includes a harvested leaf of an $F_1$ progeny plant having a reduced amount of nornicotine and/or N'-nitrosonomicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar NC 2000 SRC, a representative sample seed of the cultivar having been deposited with the ATCC under ATCC Accession No. PTA-121053, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing an $F_1$ progeny seed produced by a method comprising crossing two tobacco plants and harvesting the resultant tobacco seed, where at least one tobacco plant is produced by growing a seed of tobacco cultivar NC 2000 SRC, a representative sample seed of the cultivar having been deposited with the ATCC under ATCC Accession No. PTA-121053, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present disclosure further includes a tobacco product prepared from an $F_1$ progeny tobacco plant, or part thereof, where the plant or part thereof is produced by growing an $F_1$ progeny seed produced by a method comprising crossing two tobacco plants and harvesting the resultant tobacco seed, where at least one tobacco plant is produced by growing a seed of tobacco cultivar NC 2000 SRC, a representative sample seed of the cultivar having been deposited with the ATCC under ATCC Accession No. PTA-121053, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco.

In another aspect, the present disclosure includes a seed of tobacco cultivar CMS NC 2000 SRC, a representative sample seed of the cultivar having been deposited with the ATCC under ATCC Accession No. PTA-121045.

In an aspect, the present disclosure includes a tobacco plant, or part thereof, produced by growing the seed of tobacco cultivar CMS NC 2000 SRC, a representative sample seed of the cultivar having been deposited with the ATCC under ATCC Accession No. PTA-121045.

In another aspect, the present disclosure includes a harvested leaf, or part thereof, of a tobacco plant, or part thereof, produced by growing the seed of tobacco cultivar CMS NC 2000 SRC, a representative sample seed of the cultivar having been deposited with the ATCC under ATCC Accession No. PTA-121045.

In an aspect, the present disclosure includes a harvested leaf, or part thereof, of a tobacco plant, produced by growing the seed of tobacco cultivar CMS NC 2000 SRC, a representative sample seed of the cultivar having been deposited with the ATCC under ATCC Accession No. PTA-121045, where the leaf has a reduced amount of nornicotine and/or N'-nitrosonornicotine (NNN).

In another aspect, the present disclosure includes a harvested leaf, or part thereof, produced by growing the seed of tobacco cultivar CMS NC 2000 SRC, a representative sample seed of the cultivar having been deposited with the ATCC under ATCC Accession No. PTA-121045, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar CMS NC 2000 SRC, a representative sample seed of the cultivar having been deposited with the ATCC under ATCC Accession No. PTA-121045, where the product is selected from the group consisting of pipe tobacco, cigar tobacco, cigarette tobacco, chewing tobacco, leaf tobacco, shredded tobacco, cut tobacco and any combination thereof.

In an aspect, the present disclosure includes a tobacco product, prepared from a tobacco plant, or part thereof, produced by growing the seed of tobacco cultivar CMS NC 2000 SRC, a representative sample seed of the cultivar having been deposited with the ATCC under ATCC Accession No. PTA-121045, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar CMS NC 2000 SRC, a representative sample seed of the cultivar having been deposited with the ATCC under ATCC Accession No. PTA-121045, where the product is selected from the group consisting of a cigarillo, a non-ventilated recess filter cigarette, a vented recess filter cigarette, a cigar, snuff, and chewing tobacco where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar CMS NC 2000 SRC, a representative sample seed of the cultivar having been deposited with the ATCC under ATCC Accession No. PTA-121045, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and/or the second product comprises a reduced amount of nornicotine and/or N'-nitrosonornicotine (NNN).

In an aspect, the present disclosure includes a part of a tobacco plant, produced by growing the seed of tobacco cultivar CMS NC 2000 SRC, a representative sample seed of the cultivar having been deposited with the ATCC under ATCC Accession No. PTA-121045, where the part is selected from the group consisting of leaf, pollen, ovule, embryo, cotyledon, hypocotyl, meristematic cell, protoplast, root, root tip, pistil, anther, flower, shoot, stem, pod, and petiole.

In another aspect, the present disclosure includes a tissue culture produced from a protoplast or cell from a tobacco plant, or part thereof, produced by growing the seed of tobacco cultivar CMS NC 2000 SRC, a representative sample seed of the cultivar having been deposited with the ATCC under ATCC Accession No. PTA-121045, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar CMS NC 2000 SRC, a representative sample seed of the cultivar having been deposited with the ATCC under ATCC Accession No. PTA-121045, where the cell or protoplast of the tissue culture can be produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar CMS NC 2000 SRC.

In an aspect, the present disclosure includes an $F_1$ progeny plant of tobacco cultivar CMS NC 2000 SRC, a representative sample seed of the cultivar having been deposited with the ATCC under ATCC Accession No. PTA-121045.

In another aspect, the present disclosure includes an $F_1$ progeny plant of tobacco cultivar CMS NC 2000 SRC, a representative sample seed of the cultivar having been deposited with the ATCC under ATCC Accession No. PTA-121045, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is cytoplasmic male sterile (CMS), where the cytoplasmic male sterile plant is a plant of tobacco cultivar CMS NC 2000 SRC, a representative sample seed of the cultivar having been deposited with the ATCC under ATCC Accession No. PTA-121045.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS NC 2000 SRC, a representative sample seed of the cultivar having been deposited with the ATCC under ATCC Accession No. PTA-121045.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS NC 2000 SRC, a representative sample seed of the cultivar having been deposited with the ATCC under ATCC Accession No. PTA-121045, where the plant of tobacco cultivar CMS NC 2000 SRC is the female parent.

In another aspect, the present disclosure includes a method for producing a tobacco seed comprising crossing two tobacco plants and harvesting the resultant tobacco seed, where at least one tobacco plant is cytoplasmic male sterile (CMS), where the cytoplasmic male sterile plant is a plant of tobacco cultivar CMS NC 2000 SRC, a representative sample seed of the cultivar having been deposited with the ATCC under ATCC Accession No. PTA-121045.

In an aspect, the present disclosure also includes a container of $F_1$ progeny seeds produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2000 SRC, a representative sample seed of the cultivar having been deposited with the ATCC under ATCC Accession No. PTA-121045.

In an aspect, the present disclosure includes an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2000 SRC, a representative sample seed of the cultivar having been deposited with the ATCC under ATCC Accession No. PTA-121045.

In an aspect, the present disclosure also includes a harvested leaf of an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2000 SRC, a representative sample seed of the cultivar having been deposited with the ATCC under ATCC Accession No. PTA-121045.

In another aspect, the present disclosure further includes a harvested leaf of an $F_1$ progeny plant having a reduced amount of nornicotine and/or N'-nitrosonomicotine (NNN) produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2000 SRC, a representative sample seed of the cultivar having been deposited with the ATCC under ATCC Accession No. PTA-121045.

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2000 SRC, a representative sample seed of the cultivar having been deposited with the ATCC under ATCC Accession No. PTA-121045.

In an aspect, the present disclosure includes a tobacco product prepared from an $F_1$ progeny tobacco plant, or part thereof, where the plant or part thereof is produced by growing an $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2000 SRC, a representative sample seed of the cultivar having been deposited with the ATCC under ATCC Accession No. PTA-121045, and where the tobacco product is selected from the group consisting of pipe tobacco, cigar tobacco, cigarette tobacco, chewing tobacco, leaf tobacco, shredded tobacco, cut tobacco and any combination thereof.

In an aspect, the present disclosure further includes a tobacco product prepared from an $F_1$ progeny tobacco plant, or part thereof, where the plant or part thereof is produced by growing an $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2000 SRC, a representative sample seed of the cultivar having been deposited with the ATCC under ATCC Accession No. PTA-121045, and where the tobacco product is selected from the group consisting of a cigarillo, a non-ventilated recess filter cigarette, a vented recess filter cigarette, a cigar, snuff, and chewing tobacco.

In an aspect, the present disclosure further includes a tobacco product prepared from an $F_1$ progeny tobacco plant, or part thereof, where the plant or part thereof is produced by growing an $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2000 SRC, a representative sample seed of the cultivar having been deposited with the ATCC under ATCC Accession No. PTA-121045, and where the tobacco product is selected from the group consisting of a cigarillo, a non-ventilated recess filter cigarette, a vented recess filter cigarette, a cigar, snuff, and chewing tobacco, and further where the product has a reduced amount of nornicotine and/or N'-nitrosonornicotine (NNN).

In an aspect, the present disclosure includes a method for producing a tobacco seed comprising crossing two tobacco plants and harvesting the resultant tobacco seed, where at least one tobacco plant is cytoplasmic male sterile, where the cytoplasmic male sterile plant is a plant of tobacco cultivar CMS NC 2000 SRC, a representative sample seed of the cultivar having been deposited with the ATCC under ATCC Accession No. PTA-121045.

In an aspect, the present disclosure includes a method of vegetatively propagating a plant of a tobacco cultivar comprising the steps of (a) collecting tissue capable of being propagated from a plant of a tobacco cultivar NC 2000 SRC, a representative sample seed of the cultivar having been deposited with the ATCC under ATCC Accession No. PTA-121053 or CMS NC 2000 SRC, a representative sample seed of the cultivar having been deposited with the ATCC under ATCC Accession No. PTA-121045; (b) cultivating the tissue to obtain a proliferated shoot; and (c) rooting the proliferated shoots to obtain a rooted plantlet.

In an aspect, the present disclosure includes a method of vegetatively propagating a plant of a tobacco cultivar comprising the steps of (a) collecting tissue capable of being propagated from a plant of a tobacco cultivar NC 2000 SRC, a representative sample seed of the cultivar having been deposited with the ATCC under ATCC Accession No. PTA-121053 or CMS NC 2000 SRC, a representative sample seed of the cultivar having been deposited with the ATCC under ATCC Accession No. PTA-121045; (b) cultivating the tissue to obtain a proliferated shoot; (c) rooting the proliferated shoots to obtain a rooted plantlet; and (d) growing a plant from the rooted plantlet.

In an aspect, the present disclosure includes a method of introducing a desired trait into a tobacco cultivar comprising: (a) crossing a plant of a first tobacco cultivar NC 2000 SRC, a representative sample seed of the cultivar having been deposited with the ATCC under ATCC Accession No. PTA-121053 or CMS NC 2000 SRC, a representative sample seed of the cultivar having been deposited with the ATCC under ATCC Accession No. PTA-121045, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of said first tobacco cultivar, NC 2000 SRC or CMS NC 2000 SRC; and (e) repeating steps (c) and (d) three or more times (e.g., 3, 4, 5, 6, 7, 8, 9, 10, and the like) in succession to produce selected fourth or higher backcross progeny that comprise the desired trait. In additional aspects, steps (c) and (d) can be repeated one or more times (e.g., 1, 2, 3, 4, 5, 6, 7, 8, 9, 10, and the like) in succession to produce second or higher backcross progeny comprising the desired trait.

In an aspect, the present disclosure includes a method of introducing a desired trait into a tobacco cultivar comprising: (a) crossing a plant of a first tobacco cultivar NC 2000 SRC, a representative sample seed of the cultivar having been deposited with the ATCC under ATCC Accession No. PTA-121053, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar NC 2000 SRC, a representative sample seed of the cultivar having been deposited with the ATCC under ATCC Accession No. PTA-121053 to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar, NC 2000 SRC; and (e) repeating steps (c) and (d) three or more times in succession to produce selected fourth or higher backcross progeny that comprise the desired trait, where the trait is cytoplasmic male sterility (CMS). In additional aspects, steps (c) and (d) can be repeated one or more times in succession to produce second or higher backcross progeny comprising the desired trait, where the trait is CMS.

In an aspect, the present disclosure includes a method of introducing a desired trait into a tobacco cultivar comprising: (a) crossing a plant of a first tobacco cultivar NC 2000 SRC, a representative sample seed of the cultivar having been deposited with the ATCC under ATCC Accession No. PTA-121053, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar NC 2000 SRC, a representative sample seed of the cultivar having been deposited with the ATCC under ATCC Accession No. PTA-121053 to produce a backcross $BC_1F_1$ progeny seed; (d) growing the $BC_1F_1$ progeny seed and selecting a backcross $BC_1F_1$ progeny plant comprising the desired trait and the physiological and essentially all of morphological characteristics of the first tobacco cultivar NC 2000 SRC; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens* or *Nicotiana glauca*. In additional aspects, steps (c) and (d) can be repeated one or more times in succession to produce second or higher backcross progeny comprising the desired trait, where the trait is CMS and the CMS trait is obtained from the cytoplasm of *Nicotiana suaveolens* or *Nicotiana glauca*.

In an aspect, the present disclosure includes a method of introducing a desired trait into a tobacco cultivar comprising: (a) crossing a plant of a first tobacco cultivar NC 2000 SRC, a representative sample seed of the cultivar having been deposited with the ATCC under ATCC Accession No. PTA-121053 with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar, NC 2000 SRC to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of tobacco cultivar NC 2000 SRC; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens*, and where the second tobacco plant is CMS NC 2000 SRC. In additional aspects, steps (c) and (d) can be repeated one or more times in succession to produce second or higher backcross progeny comprising the desired trait, where the trait is CMS and the CMS trait is obtained from the cytoplasm of *Nicotiana suaveolens*.

In an aspect, the present disclosure includes a tobacco plant produced by a method comprising introducing a desired trait into a tobacco cultivar comprising: (a) crossing a plant of a first tobacco cultivar NC 2000 SRC, a representative sample seed of the cultivar having been deposited with the ATCC under ATCC Accession No. PTA-121053 or CMS NC 2000 SRC, a representative sample seed of the cultivar having been deposited with the ATCC under ATCC Accession No. PTA-121045, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar NC 2000 SRC or CMS NC 2000 SRC to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar NC 2000 SRC or CMS NC 2000 SRC; and (e) repeating steps (c) and (d) three or more times in succession to produce selected fourth or higher backcross progeny that comprise the desired trait. In additional aspects, steps (c) and (d) can be repeated one or more times in succession to produce second or higher backcross progeny that comprise the desired trait.

In another aspect, the present disclosure includes a method of introducing a desired trait into a tobacco cultivar comprising: (a) crossing a plant of a first tobacco cultivar NC 2000 SRC, a representative sample seed of the cultivar having been deposited with the ATCC under ATCC Accession No. PTA-121053 or CMS NC 2000 SRC, a representative sample seed of the cultivar having been deposited with the ATCC under ATCC Accession No. PTA-121045 with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of the first tobacco cultivar NC 2000 SRC, a representative sample seed of the cultivar having been deposited with the ATCC under ATCC Accession No. PTA-121053 or CMS NC 2000 SRC, a representative sample seed of the cultivar having been deposited with the ATCC under ATCC Accession No. PTA-121045 to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, NC 2000 SRC or CMS NC 2000 SRC; and (e) repeating steps (c) and (d) one or more times in succession to produce a selected second, third, fourth or higher backcross progeny plant that comprises the desired trait and essentially all of the physiological and morphological characteristics of the first tobacco cultivar, NC 2000 SRC or CMS NC 2000 SRC.

In another aspect, the present disclosure includes a method of introducing a desired trait into a tobacco cultivar comprising: (a) crossing a plant of a first tobacco cultivar NC 2000 SRC, a representative sample seed of the cultivar having been deposited with the ATCC under ATCC Accession No. PTA-121053 or CMS NC 2000 SRC, a representative sample seed of the cultivar having been deposited with the ATCC under ATCC Accession No. PTA-121045, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of the first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, NC 2000 SRC or CMS NC 2000 SRC; and (e) repeating steps (c) and (d) one or more times in succession to produce a selected second, third, fourth or higher backcross progeny plant that comprises the desired trait and essentially all of the physiological and morphological characteristics of the first tobacco cultivar, NC 2000 SRC or CMS NC 2000 SRC.

In another aspect, the present disclosure includes a method of introducing a desired trait into a tobacco cultivar comprising: (a) crossing a plant of a first tobacco cultivar NC 2000 SRC, a representative sample seed of the cultivar having been deposited with the ATCC under ATCC Accession No. PTA-121053 or CMS NC 2000 SRC, a representative sample seed of the cultivar having been deposited with the ATCC under ATCC Accession No. PTA-121045, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of the first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, NC 2000 SRC or CMS NC 2000 SRC; and (e) repeating steps (c) and (d) one or more times in succession to produce a selected second, third, fourth or higher backcross progeny plant that comprises the desired trait and essentially all of the physiological and morphological characteristics of the first tobacco cultivar, NC 2000 SRC or CMS NC 2000 SRC, where the plant has a desired trait of disease resistance.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the first tobacco plant is a plant of tobacco cultivar NC 2000 SRC, a representative sample seed of the cultivar having been deposited with the ATCC under ATCC Accession No. PTA-121053, or tobacco cultivar CMS NC 2000 SRC, a representative sample seed of the cultivar having been deposited with the ATCC under ATCC Accession No. PTA-121045.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the third tobacco plant is a plant of tobacco cultivar NC 2000

SRC, a representative sample seed of the cultivar having been deposited with the ATCC under ATCC Accession No. PTA-121053, or tobacco cultivar CMS NC 2000 SRC, a representative sample seed of the cultivar having been deposited with the ATCC under ATCC Accession No. PTA-121045.

In another aspect, the present disclosure includes a method of producing a plant of a tobacco cultivar NC 2000 SRC, a representative sample seed of the cultivar having been deposited with the ATCC under ATCC Accession No. PTA-121053 or tobacco cultivar CMS NC 2000 SRC, a representative sample seed of the cultivar having been deposited with the ATCC under ATCC Accession No. PTA-121045 comprising at least one (e.g., 1, 2, 3, 4, 5, 6, 7, 8, and the like) additional desired trait comprising the steps of: (a) collecting tissue capable of being propagated from a plant of a tobacco cultivar NC 2000 SRC, a representative sample seed of the cultivar having been deposited with the ATCC under ATCC Accession No. PTA-121053 or CMS NC 2000 SRC, a representative sample seed of the cultivar having been deposited with the ATCC under ATCC Accession No. PTA-121045; and (b) introducing a at least one transgene (nucleic acid construct) conferring at least one desired trait into the tissue.

In another aspect, the present disclosure includes a method of producing an herbicide resistant tobacco plant comprising transforming a tobacco plant, or part thereof, produced by growing a seed of tobacco cultivar NC 2000 SRC, a representative sample seed of the cultivar having been deposited with the ATCC under ATCC Accession No. PTA-121053 or tobacco cultivar CMS NC 2000 SRC, a representative sample seed of the cultivar having been deposited with the ATCC under ATCC Accession No. PTA-121045 with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present disclosure includes an herbicide resistant tobacco plant produced by a method comprising transforming a tobacco plant, or part thereof, produced by growing a seed of a tobacco cultivar NC 2000 SRC, a representative sample seed of the cultivar having been deposited with the ATCC under ATCC Accession No. PTA-121053 or CMS NC 2000 SRC, a representative sample seed of the cultivar having been deposited with the ATCC under ATCC Accession No. PTA-121045 with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present disclosure includes a method of producing a pest and/or insect resistant tobacco plant where the method comprises transforming a tobacco plant produced by growing a seed of tobacco cultivar NC 2000 SRC, a representative sample seed of the cultivar having been deposited with the ATCC under ATCC Accession No. PTA-121053 or tobacco cultivar CMS NC 2000 SRC, a representative sample seed of the cultivar having been deposited with the ATCC under ATCC Accession No. PTA-121045, with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of tobacco cultivar NC 2000 SRC, a representative sample seed of the cultivar having been deposited with the ATCC under ATCC Accession No. PTA-121053 or tobacco cultivar CMS NC 2000 SRC, a representative sample seed of the cultivar having been deposited with the ATCC under ATCC Accession No. PTA-121045, with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of tobacco cultivar NC 2000 SRC, a representative sample seed of the cultivar having been deposited with the ATCC under ATCC Accession No. PTA-121053 or tobacco cultivar CMS NC 2000 SRC, a representative sample seed of the cultivar having been deposited with the ATCC under ATCC Accession No. PTA-121045, with at least one transgene (nucleic acid construct) that confers pest and/or insect resistance, where the transgene (nucleic acid construct) encodes a *Bacillus thuringiensis* (BT) endotoxin.

In another aspect, the present disclosure includes a method of producing a disease resistant tobacco plant, the method comprising transforming a tobacco plant produced by growing a seed of tobacco cultivar NC 2000 SRC, a representative sample seed of the cultivar having been deposited with the ATCC under ATCC Accession No. PTA-121053 or tobacco cultivar CMS NC 2000 SRC, a representative sample seed of the cultivar having been deposited with the ATCC under ATCC Accession No. PTA-121045 with at least one transgene (nucleic acid construct) that confers disease resistance.

In a further aspect, the present disclosure includes a disease resistant tobacco plant produced by transforming a tobacco plant produced by growing a seed of tobacco cultivar NC 2000 SRC, a representative sample seed of the cultivar having been deposited with the ATCC under ATCC Accession No. PTA-121053 or tobacco cultivar CMS NC 2000 SRC, a representative sample seed of the cultivar having been deposited with the ATCC under ATCC Accession No. PTA-121045 with at least one transgene (nucleic acid construct) that confers disease resistance.

In an aspect, the present disclosure includes a seed of tobacco cultivar NC 2002 SRC, a representative sample seed of the cultivar having been deposited with the American Type Culture Collection (ATCC) under ATCC Accession No. PTA-121058.

In another aspect, the present disclosure includes a tobacco plant, or part thereof, produced by growing the seed of tobacco cultivar NC 2002 SRC, a representative sample seed of the cultivar having been deposited with the ATCC under ATCC Accession No. PTA-121058.

In a further aspect, the present disclosure includes a harvested leaf, or part thereof, of a tobacco plant, or part thereof, produced by growing the seed of tobacco cultivar NC 2002 SRC, a representative sample seed of the cultivar having been deposited with the ATCC under ATCC Accession No. PTA-121058.

In an aspect, the present disclosure includes a harvested leaf, or part thereof, of a tobacco plant, produced by growing the seed of tobacco cultivar NC 2002 SRC, a representative sample seed of the cultivar having been deposited with the ATCC under ATCC Accession No. PTA-121058, where the leaf has a reduced amount of nornicotine and/or N'-nitrosonomicotine (NNN).

In an aspect, the present disclosure includes a harvested leaf, or part thereof, produced by growing the seed of tobacco cultivar NC 2002 SRC, a representative sample seed of the cultivar having been deposited with the ATCC under ATCC Accession No. PTA-121058, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar NC 2002 SRC, a representative sample seed of the cultivar having been deposited with the ATCC under ATCC Accession No. PTA-121058, where the product is selected from the group consisting of pipe tobacco, cigar tobacco, cigarette tobacco, chewing tobacco, leaf tobacco, shredded tobacco, cut tobacco and any combination thereof.

In an aspect, the present disclosure includes a tobacco product, prepared from a tobacco plant, or part thereof, produced by growing the seed of tobacco cultivar NC 2002 SRC, a representative sample seed of the cultivar having been deposited with the ATCC under ATCC Accession No. PTA-121058, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar NC 2002 SRC, a representative sample seed of the cultivar having been deposited with the ATCC under ATCC Accession No. PTA-121058, where the product is selected from the group consisting of a cigarillo, a non-ventilated recess filter cigarette, a vented recess filter cigarette, a cigar, snuff, and chewing tobacco, and where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar NC 2002 SRC, a representative sample seed of the cultivar having been deposited with the ATCC under ATCC Accession No. PTA-121058, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and second product comprises a reduced amount of nornicotine and/or N'-nitrosonornicotine (NNN).

In an aspect, the present disclosure includes a part of a tobacco plant, produced by growing the seed of tobacco cultivar NC 2002 SRC, a representative sample seed of the cultivar having been deposited with the ATCC under ATCC Accession No. PTA-121058, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present disclosure includes a tissue culture produced from a protoplast or cell from a tobacco plant, or part thereof, produced by growing the seed of tobacco cultivar NC 2002 SRC, a representative sample seed of the cultivar having been deposited with the ATCC under ATCC Accession No. PTA-121058, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar NC 2002 SRC, a representative sample seed of the cultivar having been deposited with the ATCC under ATCC Accession No. PTA-121058, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar NC 2002 SRC.

In an aspect, the present disclosure includes an $F_1$ progeny plant of tobacco cultivar NC 2002 SRC, a representative sample seed of the cultivar having been deposited with the ATCC under ATCC Accession No. PTA-121058.

In another aspect, the present disclosure includes an $F_1$ progeny plant of tobacco cultivar NC 2002 SRC, a representative sample seed of the cultivar having been deposited with the ATCC under ATCC Accession No. PTA-121058, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is a tobacco plant produced by growing the seed of tobacco cultivar NC 2002 SRC, a representative sample seed of the cultivar having been deposited with the ATCC under ATCC Accession No. PTA-121058, where at least one tobacco plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC 2002 SRC, a representative sample seed of the cultivar having been deposited with the ATCC under ATCC Accession No. PTA-121058.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC 2002 SRC, a representative sample seed of the cultivar having been deposited with the ATCC under ATCC Accession No. PTA-121058, where the plant of tobacco cultivar NC 2002 SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC 2002 SRC, a representative sample seed of the cultivar having been deposited with the ATCC under ATCC Accession No. PTA-121058, where the plant of tobacco cultivar NC 2002 SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC 2002 SRC, a representative sample seed of the cultivar having been deposited with the ATCC under ATCC Accession No. PTA-121058, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar NC 2002 SRC, a representative sample seed of the cultivar having been deposited with the ATCC under ATCC Accession No. PTA-121058, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar NC 2002 SRC, a representative sample seed of the cultivar having been deposited with the ATCC under ATCC Accession No. PTA-121058, and where at least one tobacco plant is cytoplasmic male sterile (CMS).

In an aspect, the present disclosure also includes a harvested leaf of an $F_1$ progeny plant produced by growing a seed produced by crossing two tobacco plants and harvesting the resultant tobacco seed, where at least one tobacco plant is a tobacco plant produced by growing the seed of tobacco cultivar NC 2002 SRC, a representative sample seed of the cultivar having been deposited with the ATCC under ATCC Accession No. PTA-121058, where at least one tobacco plant is cytoplasmic male sterile (CMS).

In another aspect, the present disclosure further includes a harvested leaf of an $F_1$ progeny plant having a reduced amount of nornicotine and/or N'-nitrosonornicotine (NNN) produced by growing a seed produced by a method of comprising crossing two tobacco plants and harvesting the resultant tobacco seed, where at least one tobacco plant is a tobacco plant produced by growing the seed of tobacco cultivar NC 2002 SRC, a representative sample seed of the cultivar having been deposited with the ATCC under ATCC Accession No. PTA-121058, where at least one tobacco plant is cytoplasmic male sterile (CMS).

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar NC 2002 SRC, a representative sample seed of the cultivar having been deposited with the ATCC under ATCC Accession No. PTA-121058, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing an $F_1$ progeny seed produced by a method comprising crossing two tobacco plants and harvesting the resultant tobacco seed, where at least one tobacco plant is produced by growing a seed of tobacco cultivar NC 2002 SRC, a representative sample seed of the cultivar having been deposited with the ATCC under ATCC Accession No. PTA-121058, where at least one tobacco plant is cytoplasmic male sterile (CMS), and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present disclosure further includes a tobacco product prepared from an $F_1$ progeny tobacco plant, or part thereof, where the plant or part thereof is produced by growing an $F_1$ progeny seed produced by a method comprising crossing two tobacco plants and harvesting the resultant tobacco seed, where at least one tobacco plant is produced by growing a seed of tobacco cultivar NC 2002 SRC, a representative sample seed of the cultivar having been deposited with the ATCC under ATCC Accession No. PTA-121058, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco.

In another aspect, the present disclosure includes a seed of tobacco cultivar CMS NC 2002 SRC, a representative sample seed of the cultivar having been deposited with the ATCC under ATCC Accession No. PTA-121041.

In an aspect, the present disclosure includes a tobacco plant, or part thereof, produced by growing the seed of tobacco cultivar CMS NC 2002 SRC, a representative sample seed of the cultivar having been deposited with the ATCC under ATCC Accession No. PTA-121041.

In another aspect, the present disclosure includes a harvested leaf, or part thereof, of a tobacco plant, or part thereof, produced by growing the seed of tobacco cultivar CMS NC 2002 SRC, a representative sample seed of the cultivar having been deposited with the ATCC under ATCC Accession No. PTA-121041.

In an aspect, the present disclosure includes a harvested leaf, or part thereof, of a tobacco plant, produced by growing the seed of tobacco cultivar CMS NC 2002 SRC, a representative sample seed of the cultivar having been deposited with the ATCC under ATCC Accession No. PTA-121041, where the leaf has a reduced amount of nornicotine and/or N-nitrosonornicotine (NNN).

In another aspect, the present disclosure includes a harvested leaf, or part thereof, produced by growing the seed of tobacco cultivar CMS NC 2002 SRC, a representative sample seed of the cultivar having been deposited with the ATCC under ATCC Accession No. PTA-121041, where the leaf has a reduced amount of nornicotine and/or N-nitrosonornicotine (NNN), where the reduced amount of nornicotine and/or N-nitrosonomicotine (NNN) is reduced in a smoke stream produced from the leaf.

In a further aspect, the present disclosure includes a tobacco product, prepared from a tobacco plant, or part thereof, produced by growing the seed of tobacco cultivar CMS NC 2002 SRC, a representative sample seed of the cultivar having been deposited with the ATCC under ATCC Accession No. PTA-121041, where the product is selected from the group consisting of pipe tobacco, cigar tobacco, cigarette tobacco, chewing tobacco, leaf tobacco, shredded tobacco, cut tobacco and any combination thereof.

In an aspect, the present disclosure includes a tobacco product, prepared from a tobacco plant, or part thereof, produced by growing the seed of tobacco cultivar CMS NC 2002 SRC, a representative sample seed of the cultivar having been deposited with the ATCC under ATCC Accession No. PTA-121041, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar CMS NC 2002 SRC, a representative sample seed of the cultivar having been deposited with the ATCC under ATCC Accession No. PTA-121041, where the product is selected from the group consisting of a cigarillo, a non-ventilated recess filter cigarette, a vented recess filter cigarette, a cigar, snuff, and chewing tobacco where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar CMS NC 2002 SRC, a representative sample seed of the cultivar having been deposited with the ATCC under ATCC Accession No. PTA-121041, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and/or the second product comprises a reduced amount of nornicotine and/or N'-nitrosonornicotine (NNN).

In an aspect, the present disclosure includes a part of a tobacco plant, produced by growing the seed of tobacco cultivar CMS NC 2002 SRC, a representative sample seed of the cultivar having been deposited with the ATCC under ATCC Accession No. PTA-121041, where the part is selected from the group consisting of leaf, pollen, ovule, embryo, cotyledon, hypocotyl, meristematic cell, protoplast, root, root tip, pistil, anther, flower, shoot, stem, pod, and petiole.

In another aspect, the present disclosure includes a tissue culture produced from a protoplast or cell from a tobacco plant, or part thereof, produced by growing the seed of tobacco cultivar CMS NC 2002 SRC, a representative sample seed of the cultivar having been deposited with the ATCC under ATCC Accession No. PTA-121041, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar CMS NC 2002 SRC, a representative sample seed of the cultivar having been deposited with the ATCC under ATCC Accession No. PTA-121041, where the cell or protoplast of the tissue culture can be produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar CMS NC 2002 SRC.

In an aspect, the present disclosure includes an $F_1$ progeny plant of tobacco cultivar CMS NC 2002 SRC, a representative sample seed of the cultivar having been deposited with the ATCC under ATCC Accession No. PTA-121041.

In another aspect, the present disclosure includes an $F_1$ progeny plant of tobacco cultivar CMS NC 2002 SRC, a representative sample seed of the cultivar having been deposited with the ATCC under ATCC Accession No. PTA-121041, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is cytoplasmic male sterile (CMS), where the cytoplasmic male sterile plant is a plant of tobacco cultivar CMS NC 2002 SRC, a representative sample seed of the cultivar having been deposited with the ATCC under ATCC Accession No. PTA-121041.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS NC 2002 SRC, a representative sample seed of the cultivar having been deposited with the ATCC under ATCC Accession No. PTA-121041.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS NC 2002 SRC, a representative sample seed of the cultivar having been deposited with the ATCC under ATCC Accession No. PTA-121041, where the plant of tobacco cultivar CMS NC 2002 SRC is the female parent.

In another aspect, the present disclosure includes a method for producing a tobacco seed comprising crossing two tobacco plants and harvesting the resultant tobacco seed, where at least one tobacco plant is cytoplasmic male sterile (CMS), where the cytoplasmic male sterile plant is a plant of tobacco cultivar CMS NC 2002 SRC, a representative sample seed of the cultivar having been deposited with the ATCC under ATCC Accession No. PTA-121041.

In an aspect, the present disclosure also includes a container of $F_1$ progeny seeds produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2002 SRC, a representative sample seed of the cultivar having been deposited with the ATCC under ATCC Accession No. PTA-121041.

In an aspect, the present disclosure includes an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2002 SRC, a representative sample seed of the cultivar having been deposited with the ATCC under ATCC Accession No. PTA-121041.

In an aspect, the present disclosure also includes a harvested leaf of an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2002 SRC, a representative sample seed of the cultivar having been deposited with the ATCC under ATCC Accession No. PTA-121041.

In another aspect, the present disclosure further includes a harvested leaf of an $F_1$ progeny plant having a reduced amount of nornicotine and/or N'-nitrosonornicotine (NNN) produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2002 SRC, a representative sample seed of the cultivar having been deposited with the ATCC under ATCC Accession No. PTA-121041.

In an aspect, the present disclosure also includes a harvested leaf of an $F_1$ progeny plant having a reduced amount of nornicotine and/or N'-nitrosonomicotine (NNN) in a smoke stream produced from the leaf, where the plant is produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2002 SRC, a representative sample seed of the cultivar having been deposited with the ATCC under ATCC Accession No. PTA-121041.

In an aspect, the present disclosure includes a tobacco product prepared from an $F_1$ progeny tobacco plant, or part thereof, where the plant or part thereof is produced by growing an $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2002 SRC, a representative sample seed of the cultivar having been deposited with the ATCC under ATCC Accession No. PTA-121041, and where the tobacco product is selected from the group consisting of pipe tobacco, cigar tobacco, cigarette tobacco, chewing tobacco, leaf tobacco, shredded tobacco, cut tobacco and any combination thereof.

In an aspect, the present disclosure further includes a tobacco product prepared from an $F_1$ progeny tobacco plant, or part thereof, where the plant or part thereof is produced by growing an $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2002 SRC, a representative sample seed of the cultivar having been deposited with the ATCC under ATCC Accession No. PTA-121041, and where the tobacco product is selected from the group consisting of a cigarillo, a non-ventilated recess filter cigarette, a vented recess filter cigarette, a cigar, snuff, and chewing tobacco.

In an aspect, the present disclosure further includes a tobacco product prepared from an $F_1$ progeny tobacco plant, or part thereof, where the plant or part thereof is produced by growing an $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC 2002 SRC, a representative sample seed of the cultivar having been deposited with the ATCC under ATCC Accession No. PTA-121041, and where the tobacco product is selected from the group consisting of a cigarillo, a non-ventilated recess filter cigarette, a vented recess filter cigarette, a cigar, snuff, and chewing tobacco, and further where the product has a reduced amount of nornicotine and/or N'-nitrosonornicotine (NNN).

In an aspect, the present disclosure includes a method for producing a tobacco seed comprising crossing two tobacco plants and harvesting the resultant tobacco seed, where at least one tobacco plant is cytoplasmic male sterile, where the cytoplasmic male sterile plant is a plant of tobacco cultivar CMS NC 2002 SRC, a representative sample seed of the cultivar having been deposited with the ATCC under ATCC Accession No. PTA-121041.

In an aspect, the present disclosure includes a method of vegetatively propagating a plant of a tobacco cultivar comprising the steps of (a) collecting tissue capable of being propagated from a plant of a tobacco cultivar NC 2002 SRC, a representative sample seed of the cultivar having been deposited with the ATCC under ATCC Accession No. PTA-121058 or CMS NC 2002 SRC, a representative sample seed of the cultivar having been deposited with the ATCC under ATCC Accession No. PTA-121041; (b) cultivating the tissue to obtain a proliferated shoot; and (c) rooting the proliferated shoots to obtain a rooted plantlet.

In an aspect, the present disclosure includes a method of vegetatively propagating a plant of a tobacco cultivar comprising the steps of (a) collecting tissue capable of being propagated from a plant of a tobacco cultivar NC 2002 SRC, a representative sample seed of the cultivar having been deposited with the ATCC under ATCC Accession No. PTA-121058 or CMS NC 2002 SRC, a representative sample seed of the cultivar having been deposited with the ATCC under ATCC Accession No. PTA-121041; (b) cultivating the tissue to obtain a proliferated shoot; (c) rooting the proliferated shoots to obtain a rooted plantlet; and (d) growing a plant from the rooted plantlet.

In an aspect, the present disclosure includes a method of introducing a desired trait into a tobacco cultivar comprising: (a) crossing a plant of a first tobacco cultivar NC 2002 SRC, a representative sample seed of the cultivar having been deposited with the ATCC under ATCC Accession No. PTA-121058 or CMS NC 2002 SRC, a representative sample seed of the cultivar having been deposited with the ATCC under ATCC Accession No. PTA-121041, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of said first tobacco cultivar, NC 2002 SRC or CMS NC 2002 SRC; and (e) repeating steps (c) and (d) three or more times (e.g., 3, 4, 5, 6, 7, 8, 9, 10, and the like) in succession to produce selected fourth or higher backcross progeny that comprise the desired trait. In additional aspects, steps (c) and (d) can be repeated one or more times (e.g., 1, 2, 3, 4, 5, 6, 7, 8, 9, 10, and the like) in succession to produce second or higher backcross progeny comprising the desired trait.

In an aspect, the present disclosure includes a method of introducing a desired trait into a tobacco cultivar comprising: (a) crossing a plant of a first tobacco cultivar NC 2002 SRC, a representative sample seed of the cultivar having been deposited with the ATCC under ATCC Accession No. PTA-121058, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar NC 2002 SRC, a representative sample seed of the cultivar having been deposited with the ATCC under ATCC Accession No. PTA-121058 to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar, NC 2002 SRC; and (e) repeating steps (c) and (d) three or more times in succession to produce selected fourth or higher backcross progeny that comprise the desired trait, where the trait is cytoplasmic male sterility (CMS). In additional aspects, steps (c) and (d) can be repeated one or more times in succession to produce second or higher backcross progeny comprising the desired trait, where the trait is CMS.

In an aspect, the present disclosure includes a method of introducing a desired trait into a tobacco cultivar comprising: (a) crossing a plant of a first tobacco cultivar NC 2002 SRC, a representative sample seed of the cultivar having been deposited with the ATCC under ATCC Accession No. PTA-121058, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar NC 2002 SRC, a representative sample seed of the cultivar having been deposited with the ATCC under ATCC Accession No. PTA-121058 to produce a backcross $BC_1F_1$ progeny seed; (d) growing the $BC_1F_1$ progeny seed and selecting a backcross $BC_1F_1$ progeny plant comprising the desired trait and the physiological and essentially all of morphological characteristics of the first tobacco cultivar NC 2002 SRC; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of Nicotiana suaveolens or Nicotiana glauca. In additional aspects, steps (c) and (d) can be repeated one or more times in succession to produce second or higher backcross progeny comprising the desired trait, where the trait is CMS and the CMS trait is obtained from the cytoplasm of Nicotiana suaveolens or Nicotiana glauca.

In an aspect, the present disclosure includes a method of introducing a desired trait into a tobacco cultivar comprising: (a) crossing a plant of a first tobacco cultivar NC 2002 SRC, a representative sample seed of the cultivar having been deposited with the ATCC under ATCC Accession No. PTA-121058 with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar, NC 2002 SRC to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of tobacco cultivar NC 2002 SRC; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of Nicotiana suaveolens, and where the second tobacco plant is CMS NC 2002 SRC. In additional aspects, steps (c) and (d) can be repeated one or more times in succession to produce second or higher backcross progeny comprising the desired trait, where the trait is CMS and the CMS trait is obtained from the cytoplasm of Nicotiana suaveolens.

In an aspect, the present disclosure includes a tobacco plant produced by a method comprising introducing a desired trait into a tobacco cultivar comprising: (a) crossing a plant of a first tobacco cultivar NC 2002 SRC, a representative sample seed of the cultivar having been deposited with the ATCC under ATCC Accession No. PTA-121058 or CMS NC 2002 SRC, a representative sample seed of the cultivar having been deposited with the ATCC under ATCC Accession No. PTA-121041, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar NC 2002 SRC or CMS NC 2002 SRC to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar NC 2002 SRC or CMS NC 2002 SRC; and (e) repeating steps (c) and (d) three or more times in succession to produce selected fourth or higher backcross progeny that comprise the desired trait. In additional aspects, steps (c) and (d) can be repeated one or more times in succession to produce second or higher backcross progeny that comprise the desired trait.

In another aspect, the present disclosure includes a method of introducing a desired trait into a tobacco cultivar comprising: (a) crossing a plant of a first tobacco cultivar NC 2002 SRC, a representative sample seed of the cultivar having been deposited with the ATCC under ATCC Accession No. PTA-121058 or CMS NC 2002 SRC, a representative sample seed of the cultivar having been deposited with the ATCC under ATCC Accession No. PTA-121041 with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of the first tobacco cultivar NC 2002 SRC, a representative sample seed of the cultivar having been deposited with the ATCC under ATCC Accession No. PTA-121058 or CMS NC 2002 SRC, a representative sample seed of the cultivar having been deposited with the ATCC under ATCC Accession No. PTA-121041 to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, NC 2002 SRC or CMS NC 2002 SRC; and (e) repeating steps (c) and (d) one or more times in succession to produce a selected second, third, fourth or higher backcross progeny plant that comprises the desired trait and essentially all of the physiological and morphological characteristics of the first tobacco cultivar, NC 2002 SRC or CMS NC 2002 SRC.

In another aspect, the present disclosure includes a method of introducing a desired trait into a tobacco cultivar comprising: (a) crossing a plant of a first tobacco cultivar NC 2002 SRC, a representative sample seed of the cultivar having been deposited with the ATCC under ATCC Accession No. PTA-121058 or CMS NC 2002 SRC, a representative sample seed of the cultivar having been deposited with the ATCC under ATCC Accession No. PTA-121041, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of the first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, NC 2002 SRC or CMS NC 2002 SRC; and (e) repeating steps (c) and (d) one or more times in succession to produce a selected second, third, fourth or higher backcross progeny plant that comprises the desired trait and essentially all of the physiological and morphological characteristics of the first tobacco cultivar, NC 2002 SRC or CMS NC 2002 SRC.

In another aspect, the present disclosure includes a method of introducing a desired trait into a tobacco cultivar comprising: (a) crossing a plant of a first tobacco cultivar NC 2002 SRC, a representative sample seed of the cultivar having been deposited with the ATCC under ATCC Accession No. PTA-121058 or CMS NC 2002 SRC, a representative sample seed of the cultivar having been deposited with the ATCC under ATCC Accession No. PTA-121041, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of the first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, NC 2002 SRC or CMS NC 2002 SRC; and (e) repeating steps (c) and (d) one or more times in succession to produce a selected second, third, fourth or higher backcross progeny plant that comprises the desired trait and essentially all of the physiological and morphological characteristics of the first tobacco cultivar, NC 2002 SRC or CMS NC 2002 SRC, where the plant has a desired trait of disease resistance.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the first tobacco plant is a plant of tobacco cultivar NC 2002 SRC, a representative sample seed of the cultivar having been deposited with the ATCC under ATCC Accession No. PTA-121058, or tobacco cultivar CMS NC 2002 SRC, a representative sample seed of the cultivar having been deposited with the ATCC under ATCC Accession No. PTA-121041.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the third tobacco plant is a plant of tobacco cultivar NC 2002 SRC, a representative sample seed of the cultivar having been deposited with the ATCC under ATCC Accession No. PTA-121058, or tobacco cultivar CMS NC 2002 SRC, a representative sample seed of the cultivar having been deposited with the ATCC under ATCC Accession No. PTA-121041.

In another aspect, the present disclosure includes a method of producing a plant of a tobacco cultivar NC 2002 SRC, a representative sample seed of the cultivar having been deposited with the ATCC under ATCC Accession No. PTA-121058 or tobacco cultivar CMS NC 2002 SRC, a representative sample seed of the cultivar having been deposited with the ATCC under ATCC Accession No. PTA-121041 comprising at least one (e.g., 1, 2, 3, 4, 5, 6, 7, 8, and the like) additional desired trait comprising the steps of: (a) collecting tissue capable of being propagated from a plant of a tobacco cultivar NC 2002 SRC, a representative sample seed of the cultivar having been deposited with the ATCC under ATCC Accession No. PTA-121058 or CMS NC 2002 SRC, a representative sample seed of the cultivar having been deposited with the ATCC under ATCC Accession No. PTA-121041; and (b) introducing a at least one transgene (nucleic acid construct) conferring at least one desired trait into the tissue.

In another aspect, the present disclosure includes a method of producing an herbicide resistant tobacco plant comprising transforming a tobacco plant, or part thereof, produced by growing a seed of tobacco cultivar NC 2002 SRC, a representative sample seed of the cultivar having been deposited with the ATCC under ATCC Accession No. PTA-121058 or tobacco cultivar CMS NC 2002 SRC, a representative sample seed of the cultivar having been deposited with the ATCC under ATCC Accession No. PTA-121041 with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present disclosure includes an herbicide resistant tobacco plant produced by a method comprising transforming a tobacco plant, or part thereof, produced by growing a seed of a tobacco cultivar NC 2002 SRC, a representative sample seed of the cultivar having been deposited with the ATCC under ATCC Accession No. PTA-121058 or CMS NC 2002 SRC, a representative sample seed of the cultivar having been deposited with the ATCC under ATCC Accession No. PTA-121041 with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present disclosure includes a method of producing a pest and/or insect resistant tobacco plant where the method comprises transforming a tobacco plant produced by growing a seed of tobacco cultivar NC 2002 SRC, a representative sample seed of the cultivar having been deposited with the ATCC under ATCC Accession No. PTA-121058 or tobacco cultivar CMS NC 2002 SRC, a representative sample seed of the cultivar having been deposited with the ATCC under ATCC Accession No. PTA-121041, with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of tobacco cultivar NC 2002 SRC, a representative sample seed of the cultivar having been deposited with the ATCC under ATCC Accession No. PTA-121058 or tobacco cultivar CMS NC 2002 SRC, a representative sample seed of the cultivar having been deposited with the ATCC under ATCC Accession No. PTA-121041, with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of tobacco cultivar NC 2002 SRC, a representative sample seed of the cultivar having been deposited with the ATCC under ATCC Accession No. PTA-121058 or tobacco cultivar CMS NC 2002 SRC, a representative sample seed of the cultivar having been deposited with the ATCC under ATCC Accession No. PTA-121041, with at least one transgene (nucleic acid construct) that confers pest and/or insect resistance, where the transgene (nucleic acid construct) encodes a *Bacillus thuringiensis* (BT) endotoxin.

In another aspect, the present disclosure includes a method of producing a disease resistant tobacco plant, the method comprising transforming a tobacco plant produced by growing a seed of tobacco cultivar NC 2002 SRC, a representative sample seed of the cultivar having been deposited with the ATCC under ATCC Accession No. PTA-121058 or tobacco cultivar CMS NC 2002 SRC, a representative sample seed of the cultivar having been deposited with the ATCC under ATCC Accession No. PTA-121041 with at least one transgene (nucleic acid construct) that confers disease resistance.

In a further aspect, the present disclosure includes a disease resistant tobacco plant produced by transforming a tobacco plant produced by growing a seed of tobacco cultivar NC 2002 SRC, a representative sample seed of the cultivar having been deposited with the ATCC under ATCC Accession No. PTA-121058 or tobacco cultivar CMS NC 2002 SRC, a representative sample seed of the cultivar having been deposited with the ATCC under ATCC Accession No. PTA-121041 with at least one transgene (nucleic acid construct) that confers disease resistance.

In an aspect, the present disclosure includes a seed of tobacco cultivar Burley 21 SRC, a representative sample seed of the cultivar having been deposited with the American Type Culture Collection (ATCC) under ATCC Accession No. PTA-121059.

In another aspect, the present disclosure includes a tobacco plant, or part thereof, produced by growing the seed of tobacco cultivar Burley 21 SRC, a representative sample seed of the cultivar having been deposited with the ATCC under ATCC Accession No. PTA-121059.

In a further aspect, the present disclosure includes a harvested leaf, or part thereof, of a tobacco plant, or part thereof, produced by growing the seed of tobacco cultivar Burley 21 SRC, a representative sample seed of the cultivar having been deposited with the ATCC under ATCC Accession No. PTA-121059.

In an aspect, the present disclosure includes a harvested leaf, or part thereof, of a tobacco plant, produced by growing the seed of tobacco cultivar Burley 21 SRC, a representative sample seed of the cultivar having been deposited with the ATCC under ATCC Accession No. PTA-121059, where the leaf has a reduced amount of nornicotine and/or N'-nitrosonornicotine (NNN).

In an aspect, the present disclosure includes a harvested leaf, or part thereof, produced by growing the seed of tobacco cultivar Burley 21 SRC, a representative sample seed of the cultivar having been deposited with the ATCC under ATCC Accession No. PTA-121059, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar Burley 21 SRC, a representative sample seed of the cultivar having been deposited with the ATCC under ATCC Accession No. PTA-121059, where the product is selected from the group consisting of pipe tobacco, cigar tobacco, cigarette tobacco, chewing tobacco, leaf tobacco, shredded tobacco, cut tobacco and any combination thereof.

In an aspect, the present disclosure includes a tobacco product, prepared from a tobacco plant, or part thereof, produced by growing the seed of tobacco cultivar Burley 21 SRC, a representative sample seed of the cultivar having been deposited with the ATCC under ATCC Accession No. PTA-121059, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar Burley 21 SRC, a representative sample seed of the cultivar having been deposited with the ATCC under ATCC Accession No. PTA-121059, where the product is selected from the group consisting of a cigarillo, a non-ventilated recess filter cigarette, a vented recess filter cigarette, a cigar, snuff, and chewing tobacco, and where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar Burley 21 SRC, a representative sample seed of the cultivar having been deposited with the ATCC under ATCC Accession No. PTA-121059, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and second product comprises a reduced amount of nornicotine and/or N'-nitrosonornicotine (NNN).

In an aspect, the present disclosure includes a part of a tobacco plant, produced by growing the seed of tobacco cultivar Burley 21 SRC, a representative sample seed of the cultivar having been deposited with the ATCC under ATCC Accession No. PTA-121059, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present disclosure includes a tissue culture produced from a protoplast or cell from a tobacco plant, or part thereof, produced by growing the seed of tobacco cultivar Burley 21 SRC, a representative sample seed of the cultivar having been deposited with the ATCC under ATCC Accession No. PTA-121059, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar Burley 21 SRC, a representative sample seed of the cultivar having been deposited with the ATCC under ATCC Accession No. PTA-121059, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar Burley 21 SRC.

In an aspect, the present disclosure includes an $F_1$ progeny plant of tobacco cultivar Burley 21 SRC, a representative sample seed of the cultivar having been deposited with the ATCC under ATCC Accession No. PTA-121059.

In another aspect, the present disclosure includes an $F_1$ progeny plant of tobacco cultivar Burley 21 SRC, a representative sample seed of the cultivar having been deposited with the ATCC under ATCC Accession No. PTA-121059, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is a tobacco plant produced by growing the seed of tobacco cultivar Burley 21 SRC, a representative sample seed of the cultivar having been deposited with the ATCC under ATCC Accession No. PTA-121059, where at least one tobacco plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Burley 21 SRC, a representative sample seed of the cultivar having been deposited with the ATCC under ATCC Accession No. PTA-121059.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Burley 21 SRC, a representative sample seed of the cultivar having been deposited with the ATCC under ATCC Accession No. PTA-121059, where the plant of tobacco cultivar Burley 21 SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Burley 21 SRC, a representative sample seed of the cultivar having been deposited with the ATCC under ATCC Accession No. PTA-121059, where the plant of tobacco cultivar Burley 21 SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar Burley 21 SRC, a representative sample seed of the cultivar having been deposited with the ATCC under ATCC Accession No. PTA-121059, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar Burley 21 SRC, a representative sample seed of the cultivar having been deposited with the ATCC under ATCC Accession No. PTA-121059, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar Burley 21 SRC, a representative sample seed of the cultivar having been deposited with the ATCC under ATCC Accession No. PTA-121059, and where at least one tobacco plant is cytoplasmic male sterile (CMS).

In an aspect, the present disclosure also includes a harvested leaf of an $F_1$ progeny plant produced by growing a seed produced by crossing two tobacco plants and harvesting the resultant tobacco seed, where at least one tobacco plant is a tobacco plant produced by growing the seed of tobacco cultivar Burley 21 SRC, a representative sample seed of the cultivar having been deposited with the ATCC under ATCC Accession No. PTA-121059, where at least one tobacco plant is cytoplasmic male sterile (CMS).

In another aspect, the present disclosure further includes a harvested leaf of an $F_1$ progeny plant having a reduced amount of nornicotine and/or N'-nitrosonornicotine (NNN) produced by growing a seed produced by a method of comprising crossing two tobacco plants and harvesting the resultant tobacco seed, where at least one tobacco plant is a tobacco plant produced by growing the seed of tobacco cultivar Burley 21 SRC, a representative sample seed of the cultivar having been deposited with the ATCC under ATCC Accession No. PTA-121059, where at least one tobacco plant is cytoplasmic male sterile (CMS).

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar Burley 21 SRC, a representative sample seed of the cultivar having been deposited with the ATCC under ATCC Accession No. PTA-121059, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing an $F_1$ progeny seed produced by a method comprising crossing two tobacco plants and harvesting the resultant tobacco seed, where at least one tobacco plant is produced by growing a seed of tobacco cultivar Burley 21 SRC, a representative sample seed of the cultivar having been deposited with the ATCC under ATCC Accession No. PTA-121059, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present disclosure further includes a tobacco product prepared from an $F_1$ progeny tobacco plant, or part thereof, where the plant or part thereof is produced by growing an $F_1$ progeny seed produced by a method comprising crossing two tobacco plants and harvesting the resultant tobacco seed, where at least one tobacco plant is produced by growing a seed of tobacco cultivar Burley 21 SRC, a representative sample seed of the cultivar having been deposited with the ATCC under ATCC Accession No. PTA-121059, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco.

In another aspect, the present disclosure includes a seed of tobacco cultivar CMS Burley 21 SRC, a representative sample seed of the cultivar having been deposited with the ATCC under ATCC Accession No. PTA-121044.

In an aspect, the present disclosure includes a tobacco plant, or part thereof, produced by growing the seed of tobacco cultivar CMS Burley 21 SRC, a representative sample seed of the cultivar having been deposited with the ATCC under ATCC Accession No. PTA-121044.

In another aspect, the present disclosure includes a harvested leaf, or part thereof, of a tobacco plant, or part thereof, produced by growing the seed of tobacco cultivar CMS Burley 21 SRC, a representative sample seed of the cultivar having been deposited with the ATCC under ATCC Accession No. PTA-121044.

In an aspect, the present disclosure includes a harvested leaf, or part thereof, of a tobacco plant, produced by growing the seed of tobacco cultivar CMS Burley 21 SRC, a representative sample seed of the cultivar having been deposited with the ATCC under ATCC Accession No. PTA-121044, where the leaf has a reduced amount of nornicotine and/or N'-nitrosonornicotine (NNN).

In another aspect, the present disclosure includes a harvested leaf, or part thereof, produced by growing the seed of tobacco cultivar CMS Burley 21 SRC, a representative sample seed of the cultivar having been deposited with the ATCC under ATCC Accession No. PTA-121044, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar CMS Burley 21 SRC, a representative sample seed of the cultivar having been deposited with the ATCC under ATCC Accession No. PTA-121044, where the product is selected from the group consisting of pipe tobacco, cigar tobacco, cigarette tobacco, chewing tobacco, leaf tobacco, shredded tobacco, cut tobacco and any combination thereof.

In an aspect, the present disclosure includes a tobacco product, prepared from a tobacco plant, or part thereof, produced by growing the seed of tobacco cultivar CMS Burley 21 SRC, a representative sample seed of the cultivar having been deposited with the ATCC under ATCC Accession No. PTA-121044, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar CMS Burley 21 SRC, a representative sample seed of the cultivar having been deposited with the ATCC under ATCC Accession No. PTA-121044, where the product is selected from the group consisting of a cigarillo, a non-ventilated recess filter cigarette, a vented recess filter cigarette, a cigar, snuff, and chewing tobacco where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar CMS Burley 21 SRC, a representative sample seed of the cultivar having been deposited with the ATCC under ATCC Accession No. PTA-121044, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and/or the second product comprises a reduced amount of nornicotine and/or N'-nitrosonornicotine (NNN).

In an aspect, the present disclosure includes a part of a tobacco plant, produced by growing the seed of tobacco cultivar CMS Burley 21 SRC, a representative sample seed of the cultivar having been deposited with the ATCC under ATCC Accession No. PTA-121044, where the part is selected from the group consisting of leaf, pollen, ovule, embryo, cotyledon, hypocotyl, meristematic cell, protoplast, root, root tip, pistil, anther, flower, shoot, stem, pod, and petiole.

In another aspect, the present disclosure includes a tissue culture produced from a protoplast or cell from a tobacco plant, or part thereof, produced by growing the seed of tobacco cultivar CMS Burley 21 SRC, a representative sample seed of the cultivar having been deposited with the ATCC under ATCC Accession No. PTA-121044, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar CMS Burley 21 SRC, a representative sample seed of the cultivar having been deposited with the ATCC under ATCC Accession No. PTA-121044, where the cell or protoplast of the tissue culture can be produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar CMS Burley 21 SRC.

In an aspect, the present disclosure includes an $F_1$ progeny plant of tobacco cultivar CMS Burley 21 SRC, a representative sample seed of the cultivar having been deposited with the ATCC under ATCC Accession No. PTA-121044.

In another aspect, the present disclosure includes an $F_1$ progeny plant of tobacco cultivar CMS Burley 21 SRC, a representative sample seed of the cultivar having been deposited with the ATCC under ATCC Accession No. PTA-121044, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is cytoplasmic male sterile (CMS), where the cytoplasmic male sterile plant is a plant of tobacco cultivar CMS Burley 21 SRC, a representative sample seed of the cultivar having been deposited with the ATCC under ATCC Accession No. PTA-121044.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS Burley 21 SRC, a representative sample seed of the cultivar having been deposited with the ATCC under ATCC Accession No. PTA-121044.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS Burley 21 SRC, a representative sample seed of the cultivar having been deposited with the ATCC under ATCC Accession No. PTA-121044, where the plant of tobacco cultivar CMS Burley 21 SRC is the female parent.

In another aspect, the present disclosure includes a method for producing a tobacco seed comprising crossing two tobacco plants and harvesting the resultant tobacco seed, where at least one tobacco plant is cytoplasmic male sterile (CMS), where the cytoplasmic male sterile plant is a plant of tobacco cultivar CMS Burley 21 SRC, a representative sample seed of the cultivar having been deposited with the ATCC under ATCC Accession No. PTA-121044.

In an aspect, the present disclosure also includes a container of $F_1$ progeny seeds produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Burley 21 SRC, a representative sample seed of the cultivar having been deposited with the ATCC under ATCC Accession No. PTA-121044.

In an aspect, the present disclosure includes an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Burley 21 SRC, a representative sample seed of the cultivar having been deposited with the ATCC under ATCC Accession No. PTA-121044.

In an aspect, the present disclosure also includes a harvested leaf of an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Burley 21 SRC, a representative sample seed of the cultivar having been deposited with the ATCC under ATCC Accession No. PTA-121044.

In another aspect, the present disclosure further includes a harvested leaf of an $F_1$ progeny plant having a reduced amount of nornicotine and/or N'-nitrosonornicotine (NNN) produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Burley 21 SRC, a representative sample seed of the cultivar having been deposited with the ATCC under ATCC Accession No. PTA-121044.

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Burley 21 SRC, a representative sample seed of the cultivar having been deposited with the ATCC under ATCC Accession No. PTA-121044.

In an aspect, the present disclosure includes a tobacco product prepared from an $F_1$ progeny tobacco plant, or part thereof, where the plant or part thereof is produced by growing an $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Burley 21 SRC, a representative sample seed of the cultivar having been deposited with the ATCC under ATCC Accession No. PTA-121044, and where the tobacco product is selected from the group consisting of pipe tobacco, cigar tobacco, cigarette tobacco, chewing tobacco, leaf tobacco, shredded tobacco, cut tobacco and any combination thereof.

In an aspect, the present disclosure further includes a tobacco product prepared from an $F_1$ progeny tobacco plant, or part thereof, where the plant or part thereof is produced by growing an $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Burley 21 SRC, a representative sample seed of the cultivar having been deposited with the ATCC under ATCC Accession No. PTA-121044, and where the tobacco product is selected from the group consisting of a cigarillo, a non-ventilated recess filter cigarette, a vented recess filter cigarette, a cigar, snuff, and chewing tobacco.

In an aspect, the present disclosure further includes a tobacco product prepared from an $F_1$ progeny tobacco plant, or part thereof, where the plant or part thereof is produced by growing an $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS Burley 21 SRC, a representative sample seed of the cultivar having been deposited with the ATCC under ATCC Accession No. PTA-121044, and where the tobacco product is selected from the group consisting of a cigarillo, a non-ventilated recess filter cigarette, a vented recess filter cigarette, a cigar, snuff, and chewing tobacco, and further where the product has a reduced amount of nornicotine and/or N'-nitrosonornicotine (NNN).

In an aspect, the present disclosure further includes a method of producing a tobacco product, comprising: (a) providing cured tobacco from a tobacco plant of a cultivar or a hybrid produced from said cultivar, wherein said cultivar is selected from the group consisting of Banket A1 SRC, CMS Banket A1 SRC, NC 2000 SRC, CMS NC 2000 SRC, NC 2002 SRC, CMS NC 2002 SRC, Burley 21 SRC, and CMS Burley 21 SRC; and (b) preparing a tobacco product from said cured tobacco, wherein representative sample seeds of said Banket A1 SRC, CMS Banket A1 SRC, NC 2000 SRC, CMS NC 2000 SRC, NC 2002 SRC, CMS NC 2002 SRC, Burley 21 SRC, and CMS Burley 21 SRC have been deposited at the ATCC with the following ATCC Accession Nos.: PTA-121043 for Banket A1 SRC, PTA-121054 for CMS Banket A1 SRC, PTA-121053 for NC 2000 SRC, PTA-121045 for CMS NC 2000 SRC, PTA-121058 for NC 2002 SRC, PTA-121041 for CMS NC 2002 SRC, PTA-121059 for Burley 21 SRC, and PTA-121044 for CMS Burley 21 SRC.

In an aspect, the present disclosure includes a method for producing a tobacco seed comprising crossing two tobacco plants and harvesting the resultant tobacco seed, where at least one tobacco plant is cytoplasmic male sterile, where the cytoplasmic male sterile plant is a plant of tobacco cultivar CMS Burley 21 SRC, a representative sample seed of the cultivar having been deposited with the ATCC under ATCC Accession No. PTA-121044.

In an aspect, the present disclosure includes a method of vegetatively propagating a plant of a tobacco cultivar comprising the steps of (a) collecting tissue capable of being propagated from a plant of a tobacco cultivar Burley 21 SRC, a representative sample seed of the cultivar having been deposited with the ATCC under ATCC Accession No. PTA-121059 or CMS Burley 21 SRC, a representative sample seed of the cultivar having been deposited with the ATCC under ATCC Accession No. PTA-121044; (b) cultivating the tissue to obtain a proliferated shoot; and (c) rooting the proliferated shoots to obtain a rooted plantlet.

In an aspect, the present disclosure includes a method of vegetatively propagating a plant of a tobacco cultivar comprising the steps of (a) collecting tissue capable of being propagated from a plant of a tobacco cultivar Burley 21 SRC, a representative sample seed of the cultivar having been deposited with the ATCC under ATCC Accession No. PTA-121059 or CMS Burley 21 SRC, a representative sample seed of the cultivar having been deposited with the ATCC under ATCC Accession No. PTA-121044; (b) cultivating the tissue to obtain a proliferated shoot; (c) rooting the proliferated shoots to obtain a rooted plantlet; and (d) growing a plant from the rooted plantlet.

In an aspect, the present disclosure includes a method of introducing a desired trait into a tobacco cultivar comprising: (a) crossing a plant of a first tobacco cultivar Burley 21 SRC, a representative sample seed of the cultivar having been deposited with the ATCC under ATCC Accession No. PTA-121059 or CMS Burley 21 SRC, a representative sample seed of the cultivar having been deposited with the ATCC under ATCC Accession No. PTA-121044, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of said first tobacco cultivar, Burley 21 SRC or CMS Burley 21 SRC; and (e) repeating steps (c) and (d) three or more times (e.g., 3, 4, 5, 6, 7, 8, 9, 10, and the like) in succession to produce selected fourth or higher backcross progeny that comprise the desired trait. In additional aspects, steps (c) and (d) can be repeated one or more times (e.g., 1, 2, 3, 4, 5, 6, 7, 8, 9, 10, and the like) in succession to produce second or higher backcross progeny comprising the desired trait.

In an aspect, the present disclosure includes a method of introducing a desired trait into a tobacco cultivar comprising: (a) crossing a plant of a first tobacco cultivar Burley 21 SRC, a representative sample seed of the cultivar having been deposited with the ATCC under ATCC Accession No. PTA-121059, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar Burley 21 SRC, a representative sample seed of the cultivar having been deposited with the ATCC under ATCC Accession No. PTA-121059 to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar, Burley 21 SRC; and (e) repeating steps (c) and (d) three or more times in succession to produce selected fourth or higher backcross progeny that comprise the desired trait, where the trait is cytoplasmic male sterility (CMS). In additional aspects, steps (c) and (d) can be repeated one or more times in succession to produce second or higher backcross progeny comprising the desired trait, where the trait is CMS.

In an aspect, the present disclosure includes a method of introducing a desired trait into a tobacco cultivar comprising: (a) crossing a plant of a first tobacco cultivar Burley 21 SRC, a representative sample seed of the cultivar having been deposited with the ATCC under ATCC Accession No. PTA-121059, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar Burley 21 SRC, a representative sample seed of the cultivar having been deposited with the ATCC under ATCC Accession No. PTA-121059 to produce a backcross $BC_1F_1$ progeny seed;

(d) growing the $BC_1F_1$ progeny seed and selecting a backcross $BC_1F_1$ progeny plant comprising the desired trait and the physiological and essentially all of morphological characteristics of the first tobacco cultivar Burley 21 SRC; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens* or *Nicotiana glauca*. In additional aspects, steps (c) and (d) can be repeated one or more times in succession to produce second or higher backcross progeny comprising the desired trait, where the trait is CMS and the CMS trait is obtained from the cytoplasm of *Nicotiana suaveolens* or *Nicotiana glauca*.

In an aspect, the present disclosure includes a method of introducing a desired trait into a tobacco cultivar comprising: (a) crossing a plant of a first tobacco cultivar Burley 21 SRC, a representative sample seed of the cultivar having been deposited with the ATCC under ATCC Accession No. PTA-121059 with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar, Burley 21 SRC to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of tobacco cultivar Burley 21 SRC; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens*, and where the second tobacco plant is CMS Burley 21 SRC. In additional aspects, steps (c) and (d) can be repeated one or more times in succession to produce second or higher backcross progeny comprising the desired trait, where the trait is CMS and the CMS trait is obtained from the cytoplasm of *Nicotiana suaveolens*.

In an aspect, the present disclosure includes a tobacco plant produced by a method comprising introducing a desired trait into a tobacco cultivar comprising: (a) crossing a plant of a first tobacco cultivar Burley 21 SRC, a representative sample seed of the cultivar having been deposited with the ATCC under ATCC Accession No. PTA-121059 or CMS Burley 21 SRC, a representative sample seed of the cultivar having been deposited with the ATCC under ATCC Accession No. PTA-121044, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar Burley 21 SRC or CMS Burley 21 SRC to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar Burley 21 SRC or CMS Burley 21 SRC; and (e) repeating steps (c) and (d) three or more times in succession to produce selected fourth or higher backcross progeny that comprise the desired trait. In additional aspects, steps (c) and (d) can be repeated one or more times in succession to produce second or higher backcross progeny that comprise the desired trait.

In another aspect, the present disclosure includes a method of introducing a desired trait into a tobacco cultivar comprising: (a) crossing a plant of a first tobacco cultivar Burley 21 SRC, a representative sample seed of the cultivar having been deposited with the ATCC under ATCC Accession No. PTA-121059 or CMS Burley 21 SRC, a representative sample seed of the cultivar having been deposited with the ATCC under ATCC Accession No. PTA-121044 with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of the first tobacco cultivar Burley 21 SRC, a representative sample seed of the cultivar having been deposited with the ATCC under ATCC Accession No. PTA-121059 or CMS Burley 21 SRC, a representative sample seed of the cultivar having been deposited with the ATCC under ATCC Accession No. PTA-121044 to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, Burley 21 SRC or CMS Burley 21 SRC; and (e) repeating steps (c) and (d) one or more times in succession to produce a selected second, third, fourth or higher backcross progeny plant that comprises the desired trait and essentially all of the physiological and morphological characteristics of the first tobacco cultivar, Burley 21 SRC or CMS Burley 21 SRC.

In another aspect, the present disclosure includes a method of introducing a desired trait into a tobacco cultivar comprising: (a) crossing a plant of a first tobacco cultivar Burley 21 SRC, a representative sample seed of the cultivar having been deposited with the ATCC under ATCC Accession No. PTA-121059 or CMS Burley 21 SRC, a representative sample seed of the cultivar having been deposited with the ATCC under ATCC Accession No. PTA-121044, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of the first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, Burley 21 SRC or CMS Burley 21 SRC;

and (e) repeating steps (c) and (d) one or more times in succession to produce a selected second, third, fourth or higher backcross progeny plant that comprises the desired trait and essentially all of the physiological and morphological characteristics of the first tobacco cultivar, Burley 21 SRC or CMS Burley 21 SRC.

In another aspect, the present disclosure includes a method of introducing a desired trait into a tobacco cultivar comprising: (a) crossing a plant of a first tobacco cultivar Burley 21 SRC, a representative sample seed of the cultivar having been deposited with the ATCC under ATCC Accession No. PTA-121059 or CMS Burley 21 SRC, a representative sample seed of the cultivar having been deposited with the ATCC under ATCC Accession No. PTA-121044, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of the first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, Burley 21 SRC or CMS Burley 21 SRC; and (e) repeating steps (c) and (d) one or more times in succession to produce a selected second, third, fourth or higher backcross progeny plant that comprises the desired trait and essentially all of the physiological and morphological characteristics of the first tobacco cultivar, Burley 21 SRC or CMS Burley 21 SRC, where the plant has a desired trait of disease resistance.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the first tobacco plant is a plant of tobacco cultivar Burley 21 SRC, a representative sample seed of the cultivar having been deposited with the ATCC under ATCC Accession No. PTA-121059, or tobacco cultivar CMS Burley 21 SRC, a representative sample seed of the cultivar having been deposited with the ATCC under ATCC Accession No. PTA-121044.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the third tobacco plant is a plant of tobacco cultivar Burley 21 SRC, a representative sample seed of the cultivar having been deposited with the ATCC under ATCC Accession No. PTA-121059, or tobacco cultivar CMS Burley 21 SRC, a representative sample seed of the cultivar having been deposited with the ATCC under ATCC Accession No. PTA-121044.

In another aspect, the present disclosure includes a method of producing a plant of a tobacco cultivar Burley 21 SRC, a representative sample seed of the cultivar having been deposited with the ATCC under ATCC Accession No. PTA-121059 or tobacco cultivar CMS Burley 21 SRC, a representative sample seed of the cultivar having been deposited with the ATCC under ATCC Accession No. PTA-121044 comprising at least one (e.g., 1, 2, 3, 4, 5, 6, 7, 8, and the like) additional desired trait comprising the steps of: (a) collecting tissue capable of being propagated from a plant of a tobacco cultivar Burley 21 SRC, a representative sample seed of the cultivar having been deposited with the ATCC under ATCC Accession No. PTA-121059 or CMS Burley 21 SRC, a representative sample seed of the cultivar having been deposited with the ATCC under ATCC Accession No. PTA-121044; and (b) introducing a at least one transgene (nucleic acid construct) conferring at least one desired trait into the tissue.

In another aspect, the present disclosure includes a method of producing an herbicide resistant tobacco plant comprising transforming a tobacco plant, or part thereof, produced by growing a seed of tobacco cultivar Burley 21 SRC, a representative sample seed of the cultivar having been deposited with the ATCC under ATCC Accession No. PTA-121059 or tobacco cultivar CMS Burley 21 SRC, a representative sample seed of the cultivar having been deposited with the ATCC under ATCC Accession No. PTA-121044 with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present disclosure includes an herbicide resistant tobacco plant produced by a method comprising transforming a tobacco plant, or part thereof, produced by growing a seed of a tobacco cultivar Burley 21 SRC, a representative sample seed of the cultivar having been deposited with the ATCC under ATCC Accession No. PTA-121059 or CMS Burley 21 SRC, a representative sample seed of the cultivar having been deposited with the ATCC under ATCC Accession No. PTA-121044 with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present disclosure includes a method of producing a pest and/or insect resistant tobacco plant where the method comprises transforming a tobacco plant produced by growing a seed of tobacco cultivar Burley 21 SRC, a representative sample seed of the cultivar having been deposited with the ATCC under ATCC Accession No. PTA-121059 or tobacco cultivar CMS Burley 21 SRC, a representative sample seed of the cultivar having been deposited with the ATCC under ATCC Accession No. PTA-121044, with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of tobacco cultivar Burley 21 SRC, a representative sample seed of the cultivar having been deposited with the ATCC under ATCC Accession No. PTA-121059 or tobacco cultivar CMS Burley 21 SRC, a representative sample seed of the cultivar having been deposited with the ATCC under ATCC Accession No. PTA-121044, with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of tobacco cultivar Burley 21 SRC, a representative sample seed of the cultivar having been deposited with the ATCC under ATCC Accession No. PTA-121059 or tobacco cultivar CMS Burley 21 SRC, a representative sample seed of the cultivar having been deposited with the ATCC under ATCC Accession No. PTA-121044, with at least one transgene (nucleic acid construct) that confers pest and/or insect resistance, where the transgene (nucleic acid construct) encodes a *Bacillus thuringiensis* (BT) endotoxin.

In another aspect, the present disclosure includes a method of producing a disease resistant tobacco plant, the method comprising transforming a tobacco plant produced by growing a seed of tobacco cultivar Burley 21 SRC, a representative sample seed of the cultivar having been deposited with the ATCC under ATCC Accession No. PTA-121059 or tobacco cultivar CMS Burley 21 SRC, a representative sample seed of the cultivar having been deposited with the ATCC under ATCC Accession No. PTA-121044 with at least one transgene (nucleic acid construct) that confers disease resistance.

In a further aspect, the present disclosure includes a disease resistant tobacco plant produced by transforming a tobacco plant produced by growing a seed of tobacco cultivar Burley 21 SRC, a representative sample seed of the cultivar having been deposited with the ATCC under ATCC Accession No. PTA-121059 or tobacco cultivar CMS Burley 21 SRC, a representative sample seed of the cultivar having been deposited with the ATCC under ATCC Accession No. PTA-121044 with at least one transgene (nucleic acid construct) that confers disease resistance.

BRIEF DESCRIPTION OF THE SEQUENCES

SEQ ID NO: 1 sets forth a cyp82e4 W329Stop nucleotide sequence.
SEQ ID NO: 2 sets forth a cyp82e5v2 W422Stop nucleotide sequence.
SEQ ID NO: 3 sets forth a cyp82e4 W329Stop amino acid sequence.
SEQ ID NO: 4 sets forth a cyp82e5v2 W422Stop amino acid sequence.
SEQ ID NO: 5 sets forth a CYP82E4 wild-type nucleotide sequence.
SEQ ID NO: 6 sets forth a CYP82E5v2 wild-type nucleotide sequence.
SEQ ID NO: 7 sets forth a CYP82E4 wild-type amino acid sequence.
SEQ ID NO: 8 sets forth a CYP82E5v2 wild-type amino acid sequence.
SEQ ID NO: 9 sets forth a CYP82E10 wild-type nucleotide sequence.
SEQ ID NO: 10 sets forth a CYP82E10 wild-type amino acid sequence.
SEQ ID NO: 11 sets forth a CYP82E10 P381S nucleotide sequence.
SEQ ID NO: 12 sets forth a CYP82E10 P381S amino acid sequence.

All three tobacco Nicotine Demethylase genes (CYP82E4, CYP82E5v2, CYP82E10) share a common structure: a 939 bp exon 1 and a 612 bp exon 2 separated by a large intron, whose length varies among the three genes. See Lewis et al., "Three nicotine demethylase genes mediate nornicotine biosynthesis in *Nicotiana tabacum* L.: Functional characterization of the CYP82E10 gene," *Phytochemistry*, 71 (2010), 1988-1998. SEQ ID NOs: 1, 2, 5, 6, 9, and 11 set forth wild-type or mutant versions of coding sequences of CYP82E4, CYP82E5v2, and CYP82E10. It is understood that, used herein, a plant comprising, having, or homozygous for a sequence selected from SEQ ID NOs: 1, 2, 5, 6, 9, and 11 refers to a plant comprising at the CYP82E4, CYP82E5v2, or CYP82E10 endogenous locus a genomic sequence comprising the coding sequence of SEQ ID NO: 1, 2, 5, 6, 9, or 11.

DETAILED DESCRIPTION OF THE DISCLOSURE

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. Hence, the following descriptions are intended to illustrate some particular embodiments of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed disclosure. Thus, the term "consisting essentially of" when used in a claim of this disclosure is not intended to be interpreted to be equivalent to "comprising."

"Introducing," in the context of a polynucleotide sequence (e.g., a recombinant polynucleotide and/or expression cassette of the disclosure), means presenting a polynucleotide sequence to the plant, plant part, and/or plant cell in such a manner that the polynucleotide sequence gains access to the interior of a cell. Where more than one polynucleotide sequence is to be introduced these polynucleotide sequences can be assembled as part of a single polynucleotide or nucleic acid construct, or as separate polynucleotide or nucleic acid constructs, and can be located on the same or different transformation vectors. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient. Thus, in some embodiments, a plant cell, plant part or plant of this disclosure can be stably transformed with a recombinant polynucleotide of the disclosure. In other embodiments, a plant cell, plant part or plant of this disclosure can be transiently transformed with a recombinant polynucleotide of the disclosure.

"Tobacco product" is defined as "any product made or derived from tobacco that is intended for human use or consumption, including any component, part, or accessory of a tobacco product (except for raw materials other than tobacco used in manufacturing a component, part, or accessory of a tobacco product)" (section 201 of the FD&C Act; 21 U.S.C. 321). The label and packaging is part of a tobacco product.

Terms "nicotine conversion rate," "percent nicotine conversion," and "percentage nicotine conversion" are used interchangeably. Percent nicotine demethylation in a sample is calculated by dividing the level of nornicotine by the combined level of nicotine and nornicotine as measured in the sample, and multiplying by 100.

Banket A1 SRC

In some aspects, the present disclosure provides tobacco cultivars, and parts thereof, from Banket A1 SRC, representative sample seeds of this cultivar having been deposited with the ATCC under ATCC Accession No. PTA-121043. In other aspects, the present disclosure provides a tobacco plant, or part thereof, produced by growing a seed of Banket A1 SRC. In further aspects, a plant of the present disclosure can include a plant with all, or essentially all, of the morphological and physiological characteristics of cultivar Banket A1 SRC.

While not being limited by process, Banket A1 SRC is a result of the introduction of three mutated CYP82E genes in a burley tobacco cultivar Banket A1. The three genes are a mutated CYP82E4 gene recited as 325-6 #775 in Lewis et al. ("Three nicotine demethylase genes mediate nornicotine biosynthesis in *Nicotiana tabacum* L.: Functional characterization of the CYP82E10 gene," *Phytochemistry*, 71 (2010), 1988-1998 (SEQ ID NO: 1, which sets forth a cyp82e4 W329Stop, hereby incorporated by reference in its entirety)), a mutated CYP82E5v2 recited in Lewis et al. (supra) as 325-6 #1-13 (SEQ ID NO: 2, which sets forth a cyp82e5v2 W422Stop, hereby incorporated by reference in its entirety), and a mutated CYP82E10 recited in Lewis et al. (supra) as 325-6 #1041 (SEQ ID NO:11, which sets forth a cyp82e10 P381S, hereby incorporated by reference in its entirety). Mutations cyp82e4 W329Stop and cyp82e5v2 W422Stop result in truncated proteins while cyp82E10 P381S results in a nonfunctional protein. A cyp82e4 W329Stop ("e4"), a cyp82e5v2 W422Stop ("e5"), and a cyp82e10 P381S ("e10") mutation are introduced from a e4e4|e5e5|e10e10 triple mutant from a strong converter burley background, line DH98-325-6, as listed in Table 4 of Lewis et al. (supra) into a burley tobacco cultivar Banket A1 background.

Banket A1 SRC is the result of seven backcrosses with burley cultivar Banket A1 as the recurrent parent, followed by two rounds of selfing with selection for homozygosity for the cyp82e4 W329Stop, the cyp82e5v2 W422Stop, and cyp82e10 P381S mutations to yield $BC_7F_3$ plants (Banket A1 SRC) in which the wild-type CYP82E4, CYP82E5v2 and CYP82E10 alleles of Banket A1 are replaced by the mutant alleles (e.g., cyp82e4 W329Stop, cyp82e5v2 W422Stop, and cyp82e10 P381S).

Banket A1 SRC progeny plants have genetic backgrounds that are at least 95%, at least 97%, at least 98%, or at least 99% similar to Banket A1. Banket A1 SRC plants exhibit low nornicotine levels and produce leaves with reduced potential for accumulating derived NNN during curing, storage, and smoking.

CMS Banket A1 SRC

In some aspects, the present disclosure provides tobacco cultivars, and parts thereof, from CMS Banket A1 SRC, representative sample seeds of this cultivar having been deposited with the ATCC under ATCC Accession No. PTA-121054. In further aspects, the present disclosure also includes a tobacco plant, or part thereof, produced by growing a seed of CMS Banket A1 SRC. In still further aspects, a plant of the present disclosure can include a plant with all, or essentially all, of the morphological and physiological characteristics of cultivar CMS Banket A1 SRC. CMS Banket A1 SRC is a male-sterile (CMS) version of Banket A1 SRC (CMS Banket A1 SRC) produced by crossing a plant of CMS Banket A1 as a female with pollen of Banket A1 SRC $BC_6F_1$ to produce male-sterile plants heterozygous for all three mutations. The CMS progeny plants of the CMS Banket A1×Banket A1 SRC $BC_6F_1$ cross are male sterile. A plurality of CMS Banket A1×Banket A1 SRC $BC_6F_1$ x CMS plants (e.g., CMS $F_1$ progeny plants) are screened for the cyp82e4 W329Stop, cyp82e5v2 W422Stop, and cyp82e10 P381S mutations to identify plants heterozygous for all three mutations. A single male-sterile plant resulting from this cross is backcrossed as a female to Banket A1 SRC to prepare $BC_7F_1$ CMS progeny. $BC_7F_1$ CMS progeny homozygous for the cyp82e4 W329Stop, the cyp82e5v2 W422Stop, and cyp82e10 P381S mutations are identified by genotyping and designated as CMS Banket A1 SRC. Because the CMS Banket A1 SRC line is male sterile, it is maintained via pollination with Banket A1 SRC. Banket A1 SRC is crossed as the male parent to CMS Banket A1 SRC to prepare CMS Banket A1 SRC $F_1$ progeny plants.

CMS Banket A1 SRC and CMS Banket A1 SRC $F_1$ progeny plants have genetic backgrounds that are at least 95%, at least 97%, at least 98%, or at least 99% similar to Banket A1. CMS Banket A1 SRC and CMS Banket A1 SRC $F_1$ progeny plants exhibit low nornicotine levels and produce leaves with reduced potential for accumulating derived NNN during curing, storage, and smoking.

NC 2000 SRC

In some aspects, the present disclosure provides tobacco cultivars, and parts thereof, from NC 2000 SRC, representative sample seeds of this cultivar having been deposited with the ATCC under ATCC Accession No. PTA-121053. In other aspects, the present disclosure provides a tobacco plant, or part thereof, produced by growing a seed of NC 2000 SRC. In further aspects, a plant of the present disclosure can include a plant with all, or essentially all, of the morphological and physiological characteristics of cultivar NC 2000 SRC.

While not being limited by process, NC 2000 SRC is a result of the introduction of three mutated CYP82E genes in a burley tobacco cultivar NC 2000. The three genes are a mutated CYP82E4 gene recited as 325-6 #775 in Lewis et al. ("Three nicotine demethylase genes mediate nornicotine biosynthesis in Nicotiana tabacum L.: Functional characterization of the CYP82E10 gene," Phytochemistry, 71 (2010), 1988-1998 (SEQ ID NO: 1, which sets forth a cyp82e4 W329Stop, hereby incorporated by reference in its entirety)), a mutated CYP82E5v2 recited in Lewis et al. (supra) as 325-6 #1-13 (SEQ ID NO: 2, which sets forth a cyp82e5v2 W422Stop, hereby incorporated by reference in its entirety), and a mutated CYP82E10 recited in Lewis et al. (supra) as 325-6 #1041 (SEQ ID NO:11, which sets forth a cyp82e10 P381S, hereby incorporated by reference in its entirety). Mutations cyp82e4 W329Stop and cyp82e5v2 W422Stop result in truncated proteins while cyp82E10 P381S results in a nonfunctional protein. A cyp82e4 W329Stop ("e4"), a cyp82e5v2 W422Stop ("e5"), and a cyp82e10 P381S ("e10") mutation are introduced from a e4e4|e5e5|e10e10 triple mutant from a strong converter burley background, line DH98-325-6, as listed in Table 4 of Lewis et al. (supra) into a burley tobacco cultivar NC 2000 background.

NC 2000 SRC is the result of seven backcrosses with burley cultivar NC 2000 as the recurrent parent, followed by two rounds of selfing with selection for homozygosity for the cyp82e4 W329Stop, the cyp82e5v2 W422Stop, and cyp82e10 P381S mutations to yield $BC_7F_3$ plants (NC 2000 SRC) in which the wild-type CYP82E4, CYP82E5v2 and CYP82E10 alleles of NC 2000 are replaced by the mutant alleles (e.g., cyp82e4 W329Stop, cyp82e5v2 W422Stop, and cyp82e10 P381S).

NC 2000 SRC progeny plants have genetic backgrounds that are at least 95%, at least 97%, at least 98%, or at least 99% similar to NC 2000. NC 2000 SRC plants exhibit low nornicotine levels and produce leaves with reduced potential for accumulating derived NNN during curing, storage, and smoking.

CMS NC 2000 SRC

In some aspects, the present disclosure provides tobacco cultivars, and parts thereof, from CMS NC 2000 SRC, representative sample seeds of this cultivar having been deposited with the ATCC under ATCC Accession No. PTA-121045. In further aspects, the present disclosure also includes a tobacco plant, or part thereof, produced by growing a seed of CMS NC 2000 SRC. In still further aspects, a plant of the present disclosure can include a plant with all, or essentially all, of the morphological and physiological characteristics of cultivar CMS NC 2000 SRC. CMS NC 2000 SRC is a male-sterile (CMS) version of NC 2000 SRC (CMS NC 2000 SRC) produced by crossing a plant of CMS NC 2000 as a female with pollen of NC 2000 SRC $BC_6F_1$ to produce male-sterile plants heterozygous for all three mutations. The CMS progeny plants of the CMS NC 2000×NC 2000 SRC $BC_6F_1$ cross are male sterile. A plurality of CMS NC 2000×NC 2000 SRC $BC_6F_1$×plants (e.g., CMS $F_1$ progeny plants) are screened for the cyp82e4 W329Stop, cyp82e5v2 W422Stop, and cyp82e10 P381S mutations to identify plants heterozygous for all three mutations. A single male-sterile plant resulting from this cross is backcrossed as a female to NC 2000 SRC to prepare $BC_7F_1$ CMS progeny. $BC_7F_1$ CMS progeny homozygous for the cyp82e4 W329Stop, the cyp82e5v2 W422Stop, and cyp82e10 P381S mutations are identified by genotyping and designated as CMS NC 2000 SRC. Because the CMS NC 2000 SRC line is male sterile, it is maintained via pollination with NC 2000 SRC. NC 2000 SRC is crossed as the male parent to CMS NC 2000 SRC to prepare CMS NC 2000 SRC $F_1$ progeny plants. CMS NC 2000 SRC and CMS NC 2000 SRC $F_1$ progeny plants have genetic backgrounds that are at least 95%, at least 97%, at least 98%, or at least 99% similar to NC 2000. CMS NC 2000 SRC and CMS NC 2000 SRC $F_1$ progeny plants exhibit low nornicotine levels and produce leaves with reduced potential for accumulating derived NNN during curing, storage, and smoking.

NC 2002 SRC

In some aspects, the present disclosure provides tobacco cultivars, and parts thereof, from NC 2002 SRC, representative sample seeds of this cultivar having been deposited with the ATCC under ATCC Accession No. PTA-121058. In other aspects, the present disclosure provides a tobacco plant, or part thereof, produced by growing a seed of NC 2002 SRC. In further aspects, a plant of the present disclosure can include a plant with all, or essentially all, of the morphological and physiological characteristics of cultivar NC 2002 SRC.

While not being limited by process, NC 2002 SRC is a result of the introduction of three mutated CYP82E genes in a burley tobacco cultivar NC 2002LC. The three genes are a mutated CYP82E4 gene recited as 325-6 #775 in Lewis et al. ("Three nicotine demethylase genes mediate nornicotine biosynthesis in *Nicotiana tabacum* L.: Functional characterization of the CYP82E10 gene," Phytochemistry, 71 (2010), 1988-1998 (SEQ ID NO: 1, which sets forth a cyp82e4 W329Stop, hereby incorporated by reference in its entirety)), a mutated CYP82E5v2 recited in Lewis et al. (supra) as 325-6 #1-13 (SEQ ID NO: 2, which sets forth a cyp82e5v2 W422Stop, hereby incorporated by reference in its entirety), and a mutated CYP82E10 recited in Lewis et al. (supra) as 325-6 #1041 (SEQ ID NO:11, which sets forth a cyp82e10 P381S, hereby incorporated by reference in its entirety). Mutations cyp82e4 W329Stop and cyp82e5v2 W422Stop result in truncated proteins while cyp82E10 P381S results in a nonfunctional protein. A cyp82e4 W329Stop ("e4"), a cyp82e5v2 W422Stop ("e5"), and a cyp82e10 P381 S ("e10") mutation are introduced from a e4e4|e5e5|e10e10 triple mutant from a strong converter burley background, line DH98-325-6, as listed in Table 4 of Lewis et al. (supra) into a burley tobacco cultivar NC 2002LC background.

NC 2002 SRC is the result of seven backcrosses with burley cultivar NC 2002LC as the recurrent parent, followed by two rounds of selfing with selection for homozygosity for the cyp82e4 W329Stop, the cyp82e5v2 W422Stop, and cyp82e10 P381S mutations to yield $BC_7F_3$ plants (NC 2002 SRC) in which the wild-type CYP82E4, CYP82E5v2 and CYP82E10 alleles of NC 2002LC are replaced by the mutant alleles (e.g., cyp82e4 W329Stop, cyp82e5v2 W422Stop, and cyp82e10 P381S).

NC 2002 SRC progeny plants have genetic backgrounds that are at least 95%, at least 97%, at least 98%, or at least 99% similar to NC 2002LC. NC 2002 SRC plants exhibit low nornicotine levels and produce leaves with reduced potential for accumulating derived NNN during curing, storage, and smoking.

CMS NC 2002 SRC

In some aspects, the present disclosure provides tobacco cultivars, and parts thereof, from CMS NC 2002 SRC, representative sample seeds of this cultivar having been deposited with the ATCC under ATCC Accession No. PTA-121041. In further aspects, the present disclosure also includes a tobacco plant, or part thereof, produced by growing a seed of CMS NC 2002 SRC. In still further aspects, a plant of the present disclosure can include a plant with all, or essentially all, of the morphological and physiological characteristics of cultivar CMS NC 2002 SRC. CMS NC 2002 SRC is a male-sterile (CMS) version of NC 2002 SRC (CMS NC 2002 SRC) produced by crossing a plant of CMS NC 2002LC as a female with pollen of NC 2002 SRC $BC_6F_1$ to produce male-sterile plants heterozygous for all three mutations. The CMS progeny plants of the CMS NC 2002LC×NC 2002 SRC $BC_6F_1$ cross are male sterile. A plurality of CMS NC 2002LC×NC 2002 SRC $BC_6F_1$×plants (e.g., CMS $F_1$ progeny plants) are screened for the cyp82e4 W329Stop, cyp82e5v2 W422Stop, and cyp82e10 P381 S mutations to identify plants heterozygous for all three mutations. A single male-sterile plant resulting from this cross is backcrossed as a female to NC 2002 SRC to prepare $BC_7F_1$ CMS progeny. $BC_7F_1$ CMS progeny homozygous for the cyp82e4 W329Stop, the cyp82e5v2 W422Stop, and cyp82e10 P381S mutations are identified by genotyping and designated as CMS NC 2002 SRC. Because the CMS NC 2002 SRC line is male sterile, it is maintained via pollination with NC 2002 SRC. NC 2002 SRC is crossed as the male parent to CMS NC 2002 SRC to prepare CMS NC 2002 SRC $F_1$ progeny plants.

CMS NC 2002 SRC and CMS NC 2002 SRC $F_1$ progeny plants have genetic backgrounds that are at least 95%, at least 97%, at least 98%, or at least 99% similar to NC 2002LC. CMS NC 2002 SRC and CMS NC 2002 SRC $F_1$ progeny plants exhibit low nornicotine levels and produce leaves with reduced potential for accumulating derived NNN during curing, storage, and smoking.

Burley 21 SRC

In some aspects, the present disclosure provides tobacco cultivars, and parts thereof, from Burley 21 SRC, representative sample seeds of this cultivar having been deposited with the ATCC under ATCC Accession No. PTA-121059. In other aspects, the present disclosure provides a tobacco plant, or part thereof, produced by growing a seed of Burley 21 SRC. In further aspects, a plant of the present disclosure can include a plant with all, or essentially all, of the morphological and physiological characteristics of cultivar Burley 21 SRC.

While not being limited by process, Burley 21 SRC is a result of the introduction of three mutated CYP82E genes in a burley tobacco cultivar Burley 21 SRC. The three genes are a mutated CYP82E4 gene recited as 325-6 #775 in Lewis et al. ("Three nicotine demethylase genes mediate nornicotine biosynthesis in *Nicotiana tabacum* L.: Functional characterization of the CYP82E10 gene," Phytochemistry, 71 (2010), 1988-1998 (SEQ ID NO: 1, which sets forth a cyp82e4 W329Stop, hereby incorporated by reference in its entirety)), a mutated CYP82E5v2 recited in Lewis et al. (supra) as 325-6 #1-13 (SEQ ID NO: 2, which sets forth a cyp82e5v2 W422Stop, hereby incorporated by reference in its entirety), and a mutated CYP82E10 recited in Lewis et al. (supra) as 325-6 #1041 (SEQ ID NO:11, which sets forth a cyp82e10 P381 S, hereby incorporated by reference in its entirety). Mutations cyp82e4 W329Stop and cyp82e5v2 W422Stop result in truncated proteins while cyp82E10 P381S results in a nonfunctional protein. A cyp82e4 W329Stop ("e4"), a cyp82e5v2 W422Stop ("e5"), and a cyp82e10 P381S ("e10") mutation are introduced from a e4e4|e5e5|e10e10 triple mutant from a strong converter burley background, line DH98-325-6, as listed in Table 4 of Lewis et al. (supra) into a burley tobacco cultivar Burley 21 SRC background.

Burley 21 SRC is the result of seven backcrosses with burley cultivar Burley 21 SRC as the recurrent parent, followed by two rounds of selfing with selection for homozygosity for the cyp82e4 W329Stop, the cyp82e5v2 W422Stop, and cyp82e10 P381S mutations to yield $BC_7F_3$ plants (Burley 21 SRC) in which the wild-type CYP82E4, CYP82E5v2 and CYP82E10 alleles of Burley 21 SRC are replaced by the mutant alleles (e.g., cyp82e4 W329Stop, cyp82e5v2 W422Stop, and cyp82e10 P381S).

Burley 21 SRC progeny plants have genetic backgrounds that are at least 95%, at least 97%, at least 98%, or at least 99% similar to Burley 21 SRC. Burley 21 SRC plants exhibit low nornicotine levels and produce leaves with reduced potential for accumulating derived NNN during curing, storage, and smoking.

CMS Burley 21 SRC

In some aspects, the present disclosure provides tobacco cultivars, and parts thereof, from CMS Burley 21 SRC, representative sample seeds of this cultivar having been deposited with the ATCC under ATCC Accession No. PTA-121044. In further aspects, the present disclosure also includes a tobacco plant, or part thereof, produced by growing a seed of CMS Burley 21 SRC. In still further aspects, a plant of the present disclosure can include a plant with all, or essentially all, of the morphological and physiological characteristics of cultivar CMS Burley 21 SRC. CMS Burley 21 SRC is a male-sterile (CMS) version of Burley 21 SRC (CMS Burley 21 SRC) produced by crossing a plant of CMS Burley 21 as a female with pollen of Burley 21 SRC BC$_6$F$_1$ to produce male-sterile plants heterozygous for all three mutations. The CMS progeny plants of the CMS Burley 21×Burley 21 SRC BC$_6$F$_1$ cross are male sterile. A plurality of CMS Burley 21×Burley 21 SRC BC$_6$F$_1$×plants (e.g., CMS F$_1$ progeny plants) are screened for the cyp82e4 W329Stop, cyp82e5v2 W422Stop, and cyp82e10 P381S mutations to identify plants heterozygous for all three mutations. A single male-sterile plant resulting from this cross is backcrossed as a female to Burley 21 SRC to prepare BC$_7$F$_1$ CMS progeny. BC$_7$F$_1$ CMS progeny homozygous for the cyp82e4 W329Stop, the cyp82e5v2 W422Stop, and cyp82e10 P381 S mutations are identified by genotyping and designated as CMS Burley 21 SRC. Because the CMS Burley 21 SRC line is male sterile, it is maintained via pollination with Burley 21 SRC. Burley 21 SRC is crossed as the male parent to CMS Burley 21 SRC to prepare CMS Burley 21 SRC F$_1$ progeny plants.

CMS Burley 21 SRC and CMS Burley 21 SRC F$_1$ progeny plants have genetic backgrounds that are at least 95%, at least 97%, at least 98%, or at least 99% similar to Burley 21 SRC. CMS Burley 21 SRC and CMS Burley 21 SRC F$_1$ progeny plants exhibit low nornicotine levels and produce leaves with reduced potential for accumulating derived NNN during curing, storage, and smoking.

Other Plants

The present disclosure includes a tobacco seed produced by crossing two parent tobacco plants and harvesting the resultant tobacco seed, where at least one parent tobacco plant is Banket A1 SRC. In one aspect, the Banket A1 SRC is the male parent plant. In another aspect, the CMS Banket A1 SRC is the female parent plant. One aspect of the present disclosure provides tobacco plants that are homozygous at the cyp82e4, cyp82e5v2, and cyp82E10 loci for SEQ ID NO: 1, SEQ ID NO: 2, and SEQ ID NO: 11, respectively, and which share a genetic background that is greater than about 75%, 80%, 85%, 90%, 95%, 98%, or 99% similar to Banket A1 or CMS Banket A1. In one aspect, approximately or greater than about 50%, 75%, or 100% of a progeny's genetics is provided by a plant of the present disclosure that is homozygous at the cyp82e4, cyp82e5v2, and cyp82E10 loci for SEQ ID NO: 1, SEQ ID NO: 2, and SEQ ID NO: 11, respectively. In one aspect, a plant of the present disclosure has a genetic background that is at least 95%, at least 97%, at least 98%, or at least 99% similar to Banket A1 or CMS Banket A1. In another aspect, a plant of the present disclosure exhibits low nornicotine and is not subject to conversion to high nornicotine. In one aspect, a plant of the present disclosure is the progeny plant of a female or male parent plant that is *Fusarium* wilt resistant. In another aspect, a plant of Banket A1 SRC has low resistance to black shank and moderate resistance to bacterial wilt.

The present disclosure includes a tobacco seed produced by crossing two parent tobacco plants and harvesting the resultant tobacco seed, where at least one parent tobacco plant is NC 2000 SRC. In one aspect, the NC 2000 SRC is the male parent plant. In another aspect, the CMS NC 2000 SRC is the female parent plant. One aspect of the present disclosure provides tobacco plants that are homozygous at the cyp82e4, cyp82e5v2, and cyp82E10 loci for SEQ ID NO: 1, SEQ ID NO: 2, and SEQ ID NO: 11, respectively, and which share a genetic background that is greater than about 75%, 80%, 85%, 90%, 95%, 98%, or 99% similar to NC 2000 or CMS NC 2000. In one aspect, approximately or greater than about 50%, 75%, or 100% of a progeny's genetics is provided by a plant of the present disclosure that is homozygous at the cyp82e4, cyp82e5v2, and cyp82E10 loci for SEQ ID NO: 1, SEQ ID NO: 2, and SEQ ID NO: 11, respectively. In one aspect, a plant of the present disclosure has a genetic background that is at least 95%, at least 97%, at least 98%, or at least 99% similar to NC 2000 or CMS NC 2000. In another aspect, a plant of the present disclosure exhibits low nornicotine and is not subject to conversion to high nornicotine. In one aspect, a plant of the present disclosure is the progeny plant of a female or male parent plant that is *Fusarium* wilt resistant. In another aspect, a plant of NC 2000 SRC has low resistance to black shank and moderate resistance to bacterial wilt.

The present disclosure includes a tobacco seed produced by crossing two parent tobacco plants and harvesting the resultant tobacco seed, where at least one parent tobacco plant is NC 2002 SRC. In one aspect, the NC 2002 SRC is the male parent plant. In another aspect, the CMS NC 2002 SRC is the female parent plant. One aspect of the present disclosure provides tobacco plants that are homozygous at the cyp82e4, cyp82e5v2, and cyp82E10 loci for SEQ ID NO: 1, SEQ ID NO: 2, and SEQ ID NO: 11, respectively, and which share a genetic background that is greater than about 75%, 80%, 85%, 90%, 95%, 98%, or 99% similar to NC 2002LC or CMS NC 2002LC. In one aspect, approximately or greater than about 50%, 75%, or 100% of a progeny's genetics is provided by a plant of the present disclosure that is homozygous at the cyp82e4, cyp82e5v2, and cyp82E10 loci for SEQ ID NO: 1, SEQ ID NO: 2, and SEQ ID NO: 11, respectively. In one aspect, a plant of the present disclosure has a genetic background that is at least 95%, at least 97%, at least 98%, or at least 99% similar to NC 2002LC or CMS NC 2002LC. In another aspect, a plant of the present disclosure exhibits low nornicotine and is not subject to conversion to high nornicotine. In one aspect, a plant of the present disclosure is the progeny plant of a female or male parent plant that is *Fusarium* wilt resistant. In another aspect, a plant of NC 2002 SRC has low resistance to black shank and moderate resistance to bacterial wilt.

The present disclosure includes a tobacco seed produced by crossing two parent tobacco plants and harvesting the resultant tobacco seed, where at least one parent tobacco plant is Burley 21 SRC. In one aspect, the Burley 21 SRC is the male parent plant. In another aspect, the CMS Burley 21 SRC is the female parent plant. One aspect of the present disclosure provides tobacco plants that are homozygous at the cyp82e4, cyp82e5v2, and cyp82E10 loci for SEQ ID NO: 1, SEQ ID NO: 2, and SEQ ID NO: 11, respectively, and which share a genetic background that is greater than about 75%, 80%, 85%, 90%, 95%, 98%, or 99% similar to Burley 21 SRC or CMS Burley 21. In one aspect, approximately or greater than about 50%, 75%, or 100% of a progeny's genetics is provided by a plant of the present disclosure that is homozygous at the cyp82e4, cyp82e5v2, and cyp82E10 loci for SEQ ID NO: 1, SEQ ID NO: 2, and SEQ ID NO: 11, respectively. In one aspect, a plant of the present disclosure has a genetic background that is at least 95%, at least 97%, at least 98%, or at least 99% similar to Burley 21 SRC or CMS Burley 21. In another aspect, a plant of the present disclosure exhibits low nornicotine and is not subject to conversion to high nornicotine. In one aspect, a plant of the present disclosure is the progeny plant of a female or male parent plant that is *Fusarium* wilt resistant.

In another aspect, a plant of Burley 21 SRC has low resistance to black shank and moderate resistance to bacterial wilt.

In one aspect, a plant of the present disclosure is a medium-late maturing variety with moderately high yield potential. In another aspect, a plant of the present disclosure offers a broad range of important agronomic characteristics. In a further aspect, a plant of the present disclosure has one, two, three, four or more of the traits including moderate resistance to black shank, some tolerance to blue mold, black root rot resistance, and resistance to common virus diseases. In another aspect, a plant of the present disclosure has blue mold tolerance and level 4 resistance to both races of black shank and high root rot resistance. In one aspect, a plant of the present disclosure, such as Banket A1 SRC, CMS Banket A1 SRC, NC 2000 SRC, CMS NC 2000 SRC, NC 2002 SRC, CMS NC 2002 SRC, Burley 21 SRC, or CMS Burley 21 SRC, lacks *Fusarium* wilt resistance. In another aspect, a plant of the present disclosure is *Fusarium* wilt resistant. In another aspect, a plant of the present disclosure has low resistance to black shank and moderate resistance to bacterial wilt.

In an aspect, the plants of the present disclosure have reduced or eliminated ability to convert nicotine to nornicotine. In an aspect, the percentage nicotine conversion can be less than about 75%, 70%, 60%, 50%, or 25% of that found in Banket A1. In other aspects, the nicotine conversion in plants of the present disclosure, including, e.g., Banket A1 SRC or CMS Banket A1 SRC, can be less than about 4%, about 3.5%, about 3%, about 2.5%, about 2%, about 1.5%, about 1%, or any range therein. In still other aspects, the nicotine conversion in plants of the present disclosure, including, e.g., Banket A1 SRC or CMS Banket A1 SRC, can be in a range from about 3% to about 1%, about 3% to about 0.5%, or about 2% to about 0.5%. In a preferred aspect, the percentage nicotine conversion is less than about 25%, 10%, 5%, or 2% of that found in Banket A1 without the cyp82e4 W329Stop, the cyp82e5v2 W422Stop, and cyp82e10 P381 S mutations.

In an aspect, the plants of the present disclosure have reduced or eliminated ability to convert nicotine to nornicotine. In an aspect, the percentage nicotine conversion can be less than about 75%, 70%, 60%, 50%, or 25% of that found in NC 2000. In other aspects, the nicotine conversion in plants of the present disclosure, including, e.g., NC 2000 SRC or CMS NC 2000 SRC, can be less than about 4%, about 3.5%, about 3%, about 2.5%, about 2%, about 1.5%, about 1%, or any range therein. In still other aspects, the nicotine conversion in plants of the present disclosure, including, e.g., NC 2000 SRC or CMS NC 2000 SRC, can be in a range from about 3% to about 1%, about 3% to about 0.5%, or about 2% to about 0.5%. In a preferred aspect, the percentage nicotine conversion is less than about 25%, 10%, 5%, or 2% of that found in NC 2000 without the cyp82e4 W329Stop, the cyp82e5v2 W422Stop, and cyp82e10 P381S mutations.

In an aspect, the plants of the present disclosure have reduced or eliminated ability to convert nicotine to nornicotine. In an aspect, the percentage nicotine conversion can be less than about 75%, 70%, 60%, 50%, or 25% of that found in NC 2002. In other aspects, the nicotine conversion in plants of the present disclosure, including, e.g., NC 2002 SRC or CMS NC 2002 SRC, can be less than about 4%, about 3.5%, about 3%, about 2.5%, about 2%, about 1.5%, about 1%, or any range therein. In still other aspects, the nicotine conversion in plants of the present disclosure, including, e.g., NC 2002 SRC or CMS NC 2002 SRC, can be in a range from about 3% to about 1%, about 3% to about 0.5%, or about 2% to about 0.5%. In a preferred aspect, the percentage nicotine conversion is less than about 25%, 10%, 5%, or 2% of that found in NC 2002LC without the cyp82e4 W329Stop, the cyp82e5v2 W422Stop, and cyp82e10 P381S mutations. In an aspect, the tobacco plants of the present disclosure can have a nicotine conversion rate of about 3.5, 3.25, 3.0 or 2.75% or less.

In an aspect, the plants of the present disclosure have reduced or eliminated ability to convert nicotine to nornicotine. In an aspect, the percentage nicotine conversion can be less than about 75%, 70%, 60%, 50%, or 25% of that found in Burley 21 SRC. In other aspects, the nicotine conversion in plants of the present disclosure, including, e.g., Burley 21 SRC or CMS Burley 21 SRC, can be less than about 4%, about 3.5%, about 3%, about 2.5%, about 2%, about 1.5%, about 1%, or any range therein. In still other aspects, the nicotine conversion in plants of the present disclosure, including, e.g., Burley 21 SRC or CMS Burley 21 SRC, can be in a range from about 3% to about 1%, about 3% to about 0.5%, or about 2% to about 0.5%. In a preferred aspect, the percentage nicotine conversion is less than about 25%, 10%, 5%, or 2% of that found in Burley 21 SRC without the cyp82e4 W329Stop, the cyp82e5v2 W422Stop, and cyp82e10 P381S mutations.

In an aspect, the tobacco plants of the present disclosure can have a nicotine conversion rate of about 3.5, 3.25, 3.0 or 2.75% or less. In another aspect, the nicotine conversion rate of tobacco plants of the present disclosure can be about 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5% or less or any range therein. In another aspect, the nicotine conversion rate of tobacco plants of the present disclosure can be about 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6% or less or any range therein. In another aspect, the nicotine conversion rates can be in a range from about 0.5% to about 0.9%, about 0.5% to about 1.5%, about 0.5% to about 2.0%, about 0.5% to about 2.5%, about 0.5% to about 2.75%, and about 0.5% to about 3.0%. In another aspect, the nicotine conversion rates can be in a range from about 1.0% to about 1.5%, about 1.0% to about 1.75%, about 1.0% to about 2.0%, about 1.0% to about 2.5%, about 1.0% to about 2.75%, or about 1.0% to about 3.0%. In another aspect, the nicotine conversion rate in a plant of the present disclosure can be less than about 2.9, 2.75, 2.5, 2.25, 2.0, 1.9, 1.8, 1.7, 1.6, 1.5, 1.4, 1.3, 1.2, 1.1 or 1.0% or any range therein.

In another aspect, the tobacco plants of the present disclosure typically have a reduced amount of nornicotine of less than about 0.10% dry weight. For example, the nornicotine content in such plants can be about 1.2, 1.0, 0.7, 0.5, 0.4, 0.2, 0.1, 0.09, 0.085, 0.08, 0.075, 0.07, 0.065, 0.06, 0.055, 0.05, 0.045, 0.04, 0.035, 0.025, 0.01, 0.009, 0.0075, 0.005, 0.0025, 0.001, 0.0009, 0.00075, 0.0005, 0.00025, or 0.0001% dry weight, or undetectable, or any range therein. In another aspect, the nornicotine content can be less than about 1.2, 1.0, 0.9, 0.8, 0.7, 0.5, 0.4, 0.2, 0.1, 0.075, 0.05, 0.025, 0.01, 0.009, 0.0075, 0.005, 0.0025, 0.001, 0.0009, 0.00075, 0.0005, 0.00025, or 0.0001% dry weight, or any range therein. In another aspect, the nornicotine content in such plants can be in a range from about 1.2% to about 1.0%, about 0.7% to about 0.5%, about 0.4% to about 0.2%, about 0.1% to about 0.075%, about 0.05% to about 0.025%, about 0.01% to about 0.0075%, about 0.005% to about 0.0025%, about 0.001% to about 0.00075%, about 0.0005% to about 0.00025%, or about 0.0005% to about 0.0001% dry weight.

In some aspects, in a plant of the present disclosure, the nornicotine is a relatively small percentage of total alkaloids in the plant compared to a commercial seedlot of Banket A1, NC 2000, NC 2002, or Burley 21. In some aspects, the nornicotine in a plant of the present disclosure can be about 2% to about 1%, less than 3%, about 2%, about 1.5%, about 1%, or 0.75% of total alkaloids. Tobacco products having a reduced amount of nitrosamine content can be manufactured using tobacco plant material from plants and plant parts of the present disclosure. Thus, in some embodiments, a tobacco product manufactured using tobacco plant material from plants and plant parts of the present disclosure can comprise a reduced amount of nornicotine of less than about 3 mg/g. For example, the nornicotine content in such a product can be 3.0 mg/g, 2.5 mg/g, 2.0 mg/g, 1.5 mg/g, 1.0 mg/g, 750 µg/g, 500 µg/g, 250 µg/g, 100 µg/g, 75 µg/g, 50 µg/g, 25 µg/g, 10 µg/g, 5 µg/g, 1 µg/g, 750 ng/g, 500 ng/g, 250 ng/g, 100 ng/g, 75 ng/g, 50 ng/g, 25 ng/g, 10 ng/g, 5 ng/g, 1 ng/g, 750 pg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, and the like, or undetectable, or any range therein. The tobacco product typically has a reduced amount of NNN of less than about 10 pg/g. For example, the NNN content in such a product can be about 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, and the like, or undetectable, or any range therein. The percentage of secondary alkaloids relative to total alkaloid content contained in a plant of the present disclosure may not be statistically different than from a commercial seedlot of Banket A1, NC 2000, NC 2002, or Burley 21.

Differences between two inbred tobacco varieties or two hybrid tobacco varieties can be evaluated using statistical approaches. Statistical analysis includes the calculation of mean values, determination of the statistical significance of the sources of variation, and the calculation of the appropriate variance components. Methods for determining statistical significance are known in the art. Statistical software is available, for example, the PROC GLM function of SAS. Significance is generally presented as a "p-value." A statistically significant p-value is less than 0.10. In a preferred aspect, the p-value is less than or equal to 0.05. In another aspect, the p-value is 0.04 or less, 0.03 or less, or 0.02 or less. In yet another aspect, a statistically significant value is less than 0.01. In yet another aspect, it can be less than 0.009, less than 0.008, less than 0.007, less than 0.006, less than 0.005, less than 0.004, less than 0.003, less than 0.002, or less than 0.001.

Tobacco plants of the present disclosure that are homozygous for the cyp82e4 W329Stop, the cyp82e5v2 W422Stop, and cyp82e10 P381S alleles have a reversion rate that is statistically significantly lower than corresponding control low-converter plants having wild type nicotine demethylase CYP82E4, E5, and E10 genes. In addition, homozygous CYP82E4, CYP82E5, and CYP82E10 triple mutant tobacco plants have a percent conversion to nornicotine of less than about 2.0%, e.g., undetectable to about 2.0%, 1.9%, 1.8%, 1.7%, 1.6%, 1.5%, 1.4%, 1.3%, 1.2%, 1.1%, 1.0%, 0.9%, 0.8%, or any range therein. In some aspects, the triple mutant tobacco plants have a percent conversion to nornicotine in a range from, for example, about 1.0% to 2.0%, 0.8% to 1.8%, 0.8% to 2.0%, or 1.0% to 2.0%.

Nicotine and nornicotine can be measured in ethylene-treated leaves using methods known in the art (e.g., gas chromatography). Percent nicotine demethylation in a sample is calculated by dividing the level of nornicotine by the combined level of nicotine and nornicotine as measured in the sample, and multiplying by 100. Percent nicotine demethylation in a sample from a plant of the present disclosure is about 50, 40, 30, 20, or 10 percent of a sample from an individual plant grown from a commercial seedlot of Banket A1, NC 2000, NC 2002, or Burley 21.

In an aspect, the tobacco plants of the present disclosure have a USDA quality index of about 73, about 72, about 71, about 70, about 69, about 68, about 67 or about 66 or any range therein. In an aspect, the tobacco plants of the present disclosure have a USDA quality index of about 65. In another aspect, the quality index may be at least about 55, 60, 62.5 or greater, or any range therein. In another aspect, tobacco plants of the present disclosure can have a quality index in the range of about 60 to about 65, about 60 to about 70, about 62.5 to about 65, about 62.5 to about 70, or about 65 to about 70.

A plant of the present disclosure, including, but not limited to, Banket A1 SRC, CMS Banket A1 SRC, NC 2000 SRC, CMS NC 2000 SRC, NC 2002 SRC, CMS NC 2002 SRC, Burley 21 SRC, and CMS Burley 21 SRC, can have any yield potential, including high (e.g., over 3000 lbs/A), moderately high (e.g., 2200-3000 lbs/A), and moderate (e.g., less than 2000 lbs/A) yield potential.

In another aspect, the present disclosure also provides for a plant grown from the seed of a Banket A1 SRC or CMS Banket A1 SRC plant in which alkaloids obtained from tobacco plants grown for the seed have decreased nornicotine, as well as plant parts and tissue cultures from such plants, representative sample seeds of these cultivars having been deposited with the ATCC, for example, under ATCC Accession No. PTA-121043 for Banket A1 SRC and ATCC Accession No. PTA-121054 for CMS Banket A1 SRC.

An aspect of the present disclosure provides for parts of the cultivars Banket A1 SRC and CMS Banket A1 SRC. A part of a cultivar can comprise any plant part and includes, but is not limited to, leaves, pollen, embryos, cotyledons, hypocotyls, roots, root tips, anthers, flowers, ovules, shoots, stems, stalks, pith and capsules, tissue culture comprising tissue, callus, cells or protoplasts of the cultivars Banket A1 SRC and CMS Banket A1 SRC. In another aspect, the present disclosure provides for parts from hybrids of cultivars Banket A1 SRC and CMS Banket A1 SRC derived tobacco plants. In yet another aspect, the present disclosure provides for parts from genetically modified (e.g., by conventional breeding or genetic engineering techniques) forms of the foregoing plants and tissue culture.

In another aspect, the present disclosure also provides for a plant grown from the seed of a NC 2000 SRC or CMS NC 2000 SRC plant in which alkaloids obtained from tobacco plants grown for the seed have decreased nornicotine, as well as plant parts and tissue cultures from such plants, representative sample seeds of these cultivars having been deposited with the ATCC, for example, under ATCC Accession No. PTA-121053 for NC 2000 SRC and ATCC Accession No. PTA-121045 for CMS NC 2000 SRC.

An aspect of the present disclosure provides for parts of the cultivars NC 2000 SRC and CMS NC 2000 SRC. A part of a cultivar can comprise any plant part and includes, but is not limited to, leaves, pollen, embryos, cotyledons, hypocotyls, roots, root tips, anthers, flowers, ovules, shoots, stems, stalks, pith and capsules, tissue culture comprising tissue, callus, cells or protoplasts of the cultivars NC 2000 SRC and CMS NC 2000 SRC. In another aspect, the present disclosure provides for parts from hybrids of cultivars NC 2000 SRC and CMS NC 2000 SRC derived tobacco plants. In yet another aspect, the present disclosure provides for parts from genetically modified (e.g., by conventional breeding or genetic engineering techniques) forms of the foregoing plants and tissue culture.

In another aspect, the present disclosure also provides for a plant grown from the seed of a NC 2002 SRC or CMS NC 2002 SRC plant in which alkaloids obtained from tobacco plants grown for the seed have decreased nornicotine, as well as plant parts and tissue cultures from such plants, representative sample seeds of these cultivars having been deposited with the ATCC, for example, under ATCC Accession No. PTA-121058 for NC 2002 SRC and ATCC Accession No. PTA-121041 for CMS NC 2002 SRC.

An aspect of the present disclosure provides for parts of the cultivars NC 2002 SRC and CMS NC 2002 SRC. A part of a cultivar can comprise any plant part and includes, but is not limited to, leaves, pollen, embryos, cotyledons, hypocotyls, roots, root tips, anthers, flowers, ovules, shoots, stems, stalks, pith and capsules, tissue culture comprising tissue, callus, cells or protoplasts of the cultivars NC 2002 SRC and CMS NC 2002 SRC. In another aspect, the present disclosure provides for parts from hybrids of cultivars NC 2002 SRC and CMS NC 2002 SRC derived tobacco plants. In yet another aspect, the present disclosure provides for parts from genetically modified (e.g., by conventional breeding or genetic engineering techniques) forms of the foregoing plants and tissue culture.

In another aspect, the present disclosure also provides for a plant grown from the seed of a Burley 21 SRC or CMS Burley 21 SRC plant in which alkaloids obtained from tobacco plants grown for the seed have decreased nornicotine, as well as plant parts and tissue cultures from such plants, representative sample seeds of these cultivars having been deposited with the ATCC, for example, under ATCC Accession No. PTA-121059 for Burley 21 SRC and ATCC Accession No. PTA-121044 for CMS Burley 21 SRC.

An aspect of the present disclosure provides for parts of the cultivars Burley 21 SRC and CMS Burley 21 SRC. A part of a cultivar can comprise any plant part and includes, but is not limited to, leaves, pollen, embryos, cotyledons, hypocotyls, roots, root tips, anthers, flowers, ovules, shoots, stems, stalks, pith and capsules, tissue culture comprising tissue, callus, cells or protoplasts of the cultivars Burley 21 SRC and CMS Burley 21 SRC. In another aspect, the present disclosure provides for parts from hybrids of cultivars Burley 21 SRC and CMS Burley 21 SRC derived tobacco plants. In yet another aspect, the present disclosure provides for parts from genetically modified (e.g., by conventional breeding or genetic engineering techniques) forms of the foregoing plants and tissue culture.

Additional aspects of the present disclosure provide products comprising tobacco from the plants of the present disclosure, and parts thereof. Other aspects of the disclosure provide cured plant parts, which include, but are not limited to, a leaf, pollen, ovule, embryo, cotyledon, hypocotyl, meristematic cell, protoplast, root, root tip, pistil, anther, flower, shoot, stem, pod, petiole, and the like, and combinations thereof.

Thus, in some aspects, the present disclosure provides a cured tobacco comprising the leaves of the tobacco plant designated Banket A1 SRC, a representative sample seed of said cultivar having been deposited with the ATCC under ATCC Accession No. PTA-121043. In another aspect, the present disclosure provides a cured tobacco comprising the leaves of the tobacco plant designated CMS Banket A1 SRC, a representative sample seed of said cultivar having been deposited with the ATCC under ATCC Accession No. PTA-121054.

In an aspect, the present disclosure provides a cured tobacco comprising the stems of the tobacco plant designated Banket A1 SRC, a representative sample seed of said cultivar having been deposited with the ATCC under ATCC Accession No. PTA-121043. In another aspect, the present disclosure provides a cured tobacco comprising the stems of the tobacco plant designated CMS Banket A1 SRC, a representative sample seed of said cultivar having been deposited with the ATCC under ATCC Accession No. PTA-121054.

In an aspect, the present disclosure provides a cured tobacco comprising the leaves and stems of the tobacco plants designated Banket A1 SRC, a representative sample seed of said cultivar having been deposited with the ATCC under ATCC Accession No. PTA-121043. In another aspect, the present disclosure provides a cured tobacco comprising the leaves and stems of the tobacco plants designated CMS Banket A1 SRC, a representative sample seed of said cultivar having been deposited with the ATCC under ATCC Accession No. PTA-121054.

In some aspects, the present disclosure provides a cured tobacco comprising the leaves of the tobacco plant designated NC 2000 SRC, a representative sample seed of said cultivar having been deposited with the ATCC under ATCC Accession No. PTA-121053. In another aspect, the present disclosure provides a cured tobacco comprising the leaves of the tobacco plant designated CMS NC 2000 SRC, a representative sample seed of said cultivar having been deposited with the ATCC under ATCC Accession No. PTA-121045.

In an aspect, the present disclosure provides a cured tobacco comprising the stems of the tobacco plant designated NC 2000 SRC, a representative sample seed of said cultivar having been deposited with the ATCC under ATCC Accession No. PTA-121053. In another aspect, the present disclosure provides a cured tobacco comprising the stems of the tobacco plant designated CMS NC 2000 SRC, a representative sample seed of said cultivar having been deposited with the ATCC under ATCC Accession No. PTA-121045.

In an aspect, the present disclosure provides a cured tobacco comprising the leaves and stems of the tobacco plants designated NC 2000 SRC, a representative sample seed of said cultivar having been deposited with the ATCC under ATCC Accession No. PTA-121053. In another aspect, the present disclosure provides a cured tobacco comprising the leaves and stems of the tobacco plants designated CMS NC 2000 SRC, a representative sample seed of said cultivar having been deposited with the ATCC under ATCC Accession No. PTA-121045.

In some aspects, the present disclosure provides a cured tobacco comprising the leaves of the tobacco plant designated NC 2002 SRC, a representative sample seed of said cultivar having been deposited with the ATCC under ATCC Accession No. PTA-121058. In another aspect, the present disclosure provides a cured tobacco comprising the leaves of the tobacco plant designated CMS NC 2002 SRC, a representative sample seed of said cultivar having been deposited with the ATCC under ATCC Accession No. PTA-121041.

In an aspect, the present disclosure provides a cured tobacco comprising the stems of the tobacco plant designated NC 2002 SRC, a representative sample seed of said cultivar having been deposited with the ATCC under ATCC Accession No. PTA-121058. In another aspect, the present disclosure provides a cured tobacco comprising the stems of the tobacco plant designated CMS NC 2002 SRC, a representative sample seed of said cultivar having been deposited with the ATCC under ATCC Accession No. PTA-121041.

In an aspect, the present disclosure provides a cured tobacco comprising the leaves and stems of the tobacco plants designated NC 2002 SRC, a representative sample seed of said cultivar having been deposited with the ATCC under ATCC Accession No. PTA-121058. In another aspect, the present disclosure provides a cured tobacco comprising the leaves and stems of the tobacco plants designated CMS NC 2002 SRC, a representative sample seed of said cultivar having been deposited with the ATCC under ATCC Accession No. PTA-121041.

The present disclosure also provides a container of Banket A1 SRC or CMS Banket A1 SRC seeds or other seeds of the present disclosure in which alkaloids obtained from tobacco plants grown from greater than about 50% of the seeds have decreased nornicotine.

In another aspect, alkaloids obtained from Banket A1 SRC or CMS Banket A1 SRC plants or other plants of the present disclosure grown from greater than about 55%, 60%, 65%, 70%, 75%, 80%, 85%, 90%, or 95% of the seeds in the container have decreased nornicotine, representative samples of seeds of these cultivars having been deposited with the ATCC, for example, under ATCC Accession No. PTA-121043 for Banket A1 SRC and/or ATCC Accession No. PTA-121054 for CMS Banket A1 SRC.

The container of Banket A1 SRC or CMS Banket A1 SRC seeds or other seeds of the present disclosure may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Representative samples of seeds of these cultivars having been deposited with the ATCC, for example, under ATCC Accession No. PTA-121043 for Banket A1 SRC and/or ATCC Accession No. PTA-121054 for CMS Banket A1 SRC.

Containers of Banket A1 SRC or CMS Banket A1 SRC seeds or other seeds of the present disclosure may be any container available in the art. By way of a non-limiting example, a container may be a box, a bag, a packet, a pouch, a tape roll, a pail, a foil, or a tube. Representative samples of seeds of these cultivars having been deposited with the ATCC, for example, under ATCC Accession No. PTA-121043 for Banket A1 SRC and/or ATCC Accession No. PTA-121054 for CMS Banket A1 SRC.

In another aspect, the present disclosure also provides a container of Banket A1 SRC or CMS Banket A1 SRC in which greater than about 50% of Banket A1 SRC or CMS Banket A1 SRC seeds or other seeds of the present disclosure have decreased nornicotine. Representative samples of seeds of these cultivars having been deposited with the ATCC, for example under ATCC Accession No. PTA-121043 for Banket A1 SRC and/or ATCC Accession No. PTA-121054 for CMS Banket A1 SRC.

In one aspect, the present disclosure provides a seed of a Banket A1 SRC or CMS Banket A1 SRC plant or other plant of the present disclosure in which a plant grown from said seed is male sterile. Representative samples of seeds of these cultivars having been deposited with the ATCC, for example, under ATCC Accession No. PTA-121043 for Banket A1 SRC and/or ATCC Accession No. PTA-121054 for CMS Banket A1 SRC.

The present disclosure also provides a container of NC 2000 SRC or CMS NC 2000 SRC seeds or other seeds of the present disclosure in which alkaloids obtained from tobacco plants grown from greater than about 50% of the seeds have decreased nornicotine. In another aspect, alkaloids obtained from NC 2000 SRC or CMS NC 2000 SRC plants or other plants of the present disclosure grown from greater than about 55%, 60%, 65%, 70%, 75%, 80%, 85%, 90%, or 95% of the seeds in the container have decreased nornicotine, representative samples of seeds of these cultivars having been deposited with the ATCC, for example, under ATCC Accession No. PTA-121053 for NC 2000 SRC and/or ATCC Accession No. PTA-121045 for CMS NC 2000 SRC.

The container of NC 2000 SRC or CMS NC 2000 SRC seeds or other seeds of the present disclosure may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Representative samples of seeds of these cultivars having been deposited with the ATCC, for example, under ATCC Accession No. PTA-121053 for NC 2000 SRC and/or ATCC Accession No. PTA-121045 for CMS NC 2000 SRC.

Containers of NC 2000 SRC or CMS NC 2000 SRC seeds or other seeds of the present disclosure may be any container available in the art. By way of a non-limiting example, a container may be a box, a bag, a packet, a pouch, a tape roll, a pail, a foil, or a tube. Representative samples of seeds of these cultivars having been deposited with the ATCC, for example, under ATCC Accession No. PTA-121053 for NC 2000 SRC and/or ATCC Accession No. PTA-121045 for CMS NC 2000 SRC.

In another aspect, the present disclosure also provides a container of NC 2000 SRC or CMS NC 2000 SRC in which greater than about 50% of NC 2000 SRC or CMS NC 2000 SRC seeds or other seeds of the present disclosure have decreased nornicotine. Representative samples of seeds of these cultivars having been deposited with the ATCC, for example under ATCC Accession No. PTA-121053 for NC 2000 SRC and/or ATCC Accession No. PTA-121045 for CMS NC 2000 SRC.

In one aspect, the present disclosure provides a seed of a NC 2000 SRC or CMS NC 2000 SRC plant or other plant of the present disclosure in which a plant grown from said seed is male sterile. Representative samples of seeds of these cultivars having been deposited with the ATCC, for example, under ATCC Accession No. PTA-121053 for NC 2000 SRC and/or ATCC Accession No. PTA-121045 for CMS NC 2000 SRC.

The present disclosure also provides a container of NC 2002 SRC or CMS NC 2002 SRC seeds or other seeds of the present disclosure in which alkaloids obtained from tobacco plants grown from greater than about 50% of the seeds have decreased nornicotine. In another aspect, alkaloids obtained from NC 2002 SRC or CMS NC 2002 SRC plants or other plants of the present disclosure grown from greater than about 55%, 60%, 65%, 70%, 75%, 80%, 85%, 90%, or 95% of the seeds in the container have decreased nornicotine, representative samples of seeds of these cultivars having been deposited with the ATCC, for example, under ATCC Accession No. PTA-121058 for NC 2002 SRC and/or ATCC Accession No. PTA-121041 for CMS NC 2002 SRC.

The container of NC 2002 SRC or CMS NC 2002 SRC seeds or other seeds of the present disclosure may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Representative samples of seeds of these cultivars having been deposited with the ATCC, for example, under ATCC Accession No. PTA-121058 for NC 2002 SRC and/or ATCC Accession No. PTA-121041 for CMS NC 2002 SRC.

Containers of NC 2002 SRC or CMS NC 2002 SRC seeds or other seeds of the present disclosure may be any container available in the art. By way of a non-limiting example, a container may be a box, a bag, a packet, a pouch, a tape roll, a pail, a foil, or a tube. Representative samples of seeds of these cultivars having been deposited with the ATCC, for example, under ATCC Accession No. PTA-121058 for NC 2002 SRC and/or ATCC Accession No. PTA-121041 for CMS NC 2002 SRC.

In another aspect, the present disclosure also provides a container of NC 2002 SRC or CMS NC 2002 SRC in which greater than about 50% of NC 2002 SRC or CMS NC 2002 SRC seeds or other seeds of the present disclosure have decreased nornicotine. Representative samples of seeds of these cultivars having been deposited with the ATCC, for example under ATCC Accession No. PTA-121058 for NC 2002 SRC and/or ATCC Accession No. PTA-121041 for CMS NC 2002 SRC.

In one aspect, the present disclosure provides a seed of a NC 2002 SRC or CMS NC 2002 SRC plant or other plant of the present disclosure in which a plant grown from said seed is male sterile. Representative samples of seeds of these cultivars having been deposited with the ATCC, for example, under ATCC Accession No. PTA-121058 for NC 2002 SRC and/or ATCC Accession No. PTA-121041 for CMS NC 2002 SRC.

The present disclosure also provides a container of Burley 21 SRC or CMS Burley 21 SRC seeds or other seeds of the present disclosure in which alkaloids obtained from tobacco plants grown from greater than about 50% of the seeds have decreased nornicotine. In another aspect, alkaloids obtained from Burley 21 SRC or CMS Burley 21 SRC plants or other plants of the present disclosure grown from greater than about 55%, 60%, 65%, 70%, 75%, 80%, 85%, 90%, or 95% of the seeds in the container have decreased nornicotine, representative samples of seeds of these cultivars having been deposited with the ATCC, for example, under ATCC Accession No. PTA-121059 for Burley 21 SRC and/or ATCC Accession No. PTA-121044 for CMS Burley 21 SRC.

The container of Burley 21 SRC or CMS Burley 21 SRC seeds or other seeds of the present disclosure may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Representative samples of seeds of these cultivars having been deposited with the ATCC, for example, under ATCC Accession No. PTA-121059 for Burley 21 SRC and/or ATCC Accession No. PTA-121044 for CMS Burley 21 SRC.

Containers of Burley 21 SRC or CMS Burley 21 SRC seeds or other seeds of the present disclosure may be any container available in the art. By way of a non-limiting example, a container may be a box, a bag, a packet, a pouch, a tape roll, a pail, a foil, or a tube. Representative samples of seeds of these cultivars having been deposited with the ATCC, for example, under ATCC Accession No. PTA-121059 for Burley 21 SRC and/or ATCC Accession No. PTA-121044 for CMS Burley 21 SRC.

In another aspect, the present disclosure also provides a container of Burley 21 SRC or CMS Burley 21 SRC in which greater than about 50% of Burley 21 SRC or CMS Burley 21 SRC seeds or other seeds of the present disclosure have decreased nornicotine. Representative samples of seeds of these cultivars having been deposited with the ATCC, for example under ATCC Accession No. PTA-121059 for Burley 21 SRC and/or ATCC Accession No. PTA-121044 for CMS Burley 21 SRC.

In one aspect, the present disclosure provides a seed of a Burley 21 SRC or CMS Burley 21 SRC plant or other plant of the present disclosure in which a plant grown from said seed is male sterile. Representative samples of seeds of these cultivars having been deposited with the ATCC, for example, under ATCC Accession No. PTA-121059 for Burley 21 SRC and/or ATCC Accession No. PTA-121044 for CMS Burley 21 SRC.

Tobacco material obtained from the tobacco lines, varieties or hybrids of the present disclosure can be used to make tobacco products including, without limitation, cigarette products (e.g., cigarettes and bidi cigarettes), cigar products (e.g., cigar wrapping tobacco and cigarillos), pipe tobacco products, smokeless cigarette products, smokeless tobacco products (e.g., moist snuff, dry snuff, and chewing tobacco), films, chewables, tabs, shaped parts, gels, consumable units, insoluble matrices, hollow shapes and the like. See, e.g., U.S. Patent Publication No. US 2006/0191548, which is herein incorporated by reference in its entirety.

Tobacco products derived from plants of the present disclosure also include cigarettes and other smoking articles, particularly those smoking articles including filter elements, wherein the rod of smokeable material includes cured tobacco within a tobacco blend. In an aspect, a tobacco product can include but is not limited to pipe tobacco, cigar tobacco, cigarette tobacco, chewing tobacco, leaf tobacco, shredded tobacco, and/or cut tobacco or any combination thereof.

In an aspect, the tobacco product of the present disclosure can be a blended tobacco product. In other aspects of the disclosure, the tobacco product of the present disclosure can be a reduced nicotine tobacco product. In still other aspects, the tobacco product of the present disclosure can be a blended tobacco product with reduced nicotine content. Thus, the tobacco product of the present disclosure can be a blended reduced nicotine tobacco product. Tobacco product material comprises a blend of tobacco materials from the present disclosure, wherein the blend comprises at least about 5, 10, 20, 30, 40, 50, 60, 70, 80, 90, or 95 percent by weight of a cured tobacco, or any range therein, based on the dry weight of the tobacco material. US 2008/0245377 is herein incorporated by reference for blend mixtures in its entirety.

In an aspect, tobacco products having a reduced amount of nitrosamine content can be manufactured using tobacco plant material from plants and plant parts of the present disclosure. Thus, in some aspects, a tobacco product manufactured using tobacco plant material from plants and plant parts of the present disclosure can comprise a reduced amount of nornicotine of less than about 3 mg/g. For example, the nornicotine content in such a product can be 3.0 mg/g, 2.5 mg/g, 2.0 mg/g, 1.5 mg/g, 1.0 mg/g, 750 µg/g, 500 µg/g, 250 µg/g, 100 µg/g, 75 µg/g, 50 µg/g, 25 µg/g, 10 µg/g, 5 µg/g, 1 µg/g, 750 ng/g, 500 ng/g, 250 ng/g, 100 ng/g, 75 ng/g, 50 ng/g, 25 ng/g, 10 ng/g, 5 ng/g, 1 ng/g, 750 pg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable, or any range therein. The tobacco product typically has a reduced amount of NNN of less than about 10 pg/g. For example, the NNN content in such a product can be about 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable, or any range therein. The percentage of secondary alkaloids relative to total alkaloid content contained in a plant of the present disclosure may not be statistically different than from a commercial seedlot of Banket A1, NC 2000, NC 2002, or Burley 21.

A tobacco plant of the present disclosure designated Banket A1 SRC, CMS Banket A1 SRC, NC 2000 SRC, CMS NC 2000 SRC, NC 2002 SRC, CMS NC 2002 SRC, Burley 21 SRC, or CMS Burley 21 SRC carrying the cyp82e4 W329Stop, the cyp82e5v2 W422Stop, and cyp82e10 P381S alleles can be used in a plant breeding program to create useful lines, cultivars, varieties, progeny, inbreds, and hybrids. Thus, in some aspects, an $F_1$, $F_2$, $F_3$, or later generation tobacco plant containing the cyp82e4 W329Stop, the cyp82e5v2 W422Stop, and cyp82e10 P381S alleles is crossed with a second Nicotiana plant, and progeny of the cross are identified in which the cyp82e4 W329Stop, the cyp82e5v2 W422Stop, and cyp82e10 P381 S alleles are present. It will be appreciated that the second Nicotiana plant can be Banket A1, NC 2000, NC 2002, Burley 21 or any other Nicotiana species or line, optionally with an additional desirable trait, such as herbicide resistance.

In still other aspects, methods of the present disclosure further include self-pollinating or pollinating a male sterile pollen acceptor with a pollen donor capable of being used in production of a progeny plant of the present disclosure, such as a male sterile hybrid of the present disclosure. Either the male sterile pollen acceptor plant or the pollen donor plant has at least one mutant allele, two, or even three mutant alleles at a nicotine demethylase locus, such as the cyp82e4 W329Stop allele, the cyp82e5v2 W422Stop allele, and/or the cyp82e10 P381S allele. In an aspect, all three alleles at each nicotine demethylase locus are mutant alleles, making the plant homozygous for cyp82e4 W329Stop, cyp82e5v2 W422Stop, and cyp82e10 P381S.

Breeding can be carried out via any known procedures. DNA fingerprinting, SNP or similar technologies may be used in a marker-assisted selection (MAS) breeding program to transfer or breed mutant alleles of a nicotine demethylase gene into other tobaccos. For example, a breeder can create segregating populations from hybridizations of a genotype containing cyp82e4 W329Stop, cyp82e5v2 W422Stop, and cyp82e10 P381 S alleles with an agronomically desirable genotype. Plants in the $F_2$ or backcross generations can be screened using a marker developed from cyp82e4 W329Stop, cyp82e5v2 W422Stop, or cyp82e10 P381S alleles or a fragment thereof, using one of the techniques known in the art or disclosed herein. Plants identified as possessing one or more cyp82e4 W329Stop, cyp82e5v2 W422Stop, and cyp82e10 P381S alleles can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered. A recurrent parent in the present disclosure can be Banket A1 SRC, CMS Banket A1 SRC, NC 2000 SRC, CMS NC 2000 SRC, NC 2002 SRC, CMS NC 2002 SRC, Burley 21 SRC, or CMS Burley 21 SRC. Other breeding techniques can be found, for example, in Wernsman, E. A., and Rufty, R. C., 1987. Chapter Seventeen. Tobacco. pages 669-698 In: Cultivar Development. Crop Species. W. H. Fehr (ed.), MacMillan Publishing Go., Inc., New York, N.Y., incorporated herein by reference in their entireties.

Nicotiana species which exhibit breeding compatibility with Nicotiana tabacum include Nicotiana amplexicaulis, PI 271989; Nicotiana benthamiana PI 555478; Nicotiana bigelovii PI 555485; Nicotiana debneyi; Nicotiana excelsior PI 224063; Nicotiana glutinosa PI 555507; Nicotiana goodspeedii PI 241012; Nicotiana gossei PI 230953; Nicotiana hesperis PI 271991; Nicotiana knightiana PI 555527; Nicotiana maritima PI 555535; Nicotiana megalosiphon PI 555536; Nicotiana nudicaulis PI 555540; Nicotiana paniculata PI 555545; Nicotiana plumbaginifolia PI 555548; Nicotiana repanda PI 555552; Nicotiana rustica; Nicotiana suaveolens PI 230960; Nicotiana sylvestris PI 555569; Nicotiana tomentosa PI 266379; Nicotiana tomentosiformis; and Nicotiana trigonophylla PI 555572. See also, Compendium of Tobacco Diseases published by American Phytopathology Society, or The Genus Nicotiana Illustrated, published by Japan Tobacco Inc, hereby incorporated by reference in their entireties.

The result of a plant breeding program using the mutant tobacco plants described herein includes useful lines, cultivars, varieties, progeny, inbreds, and hybrids. As used herein, the term "cultivar" or "variety" refers to a population of plants that share constant characteristics which separate them from other plants of the same species. A cultivar or variety is often, although not always, sold commercially. While possessing one or more distinctive traits, a cultivar or variety is further characterized by a very small overall variation between individuals within that cultivar or variety. A "pure line" variety may be created by several generations of self-pollination and selection, or vegetative propagation from a single parent using tissue or cell culture techniques. A cultivar or variety can be essentially derived from another cultivar, line, or variety. As defined by the International Convention for the Protection of New Varieties of Plants (Dec. 2, 1961, as revised at Geneva on Nov. 10, 1972, on Oct. 23, 1978, and on Mar. 19, 1991), a cultivar or variety is "essentially derived" from an initial cultivar or variety if: a) it is predominantly derived from the initial cultivar or variety, or from a cultivar or variety that is predominantly derived from the initial cultivar or variety, while retaining the expression of the essential characteristics that result from the genotype or combination of genotypes of the initial cultivar or variety; b) it is clearly distinguishable from the initial cultivar or variety; and c) except for the differences which result from the act of derivation, it conforms to the initial cultivar or variety in the expression of the essential characteristics that result from the genotype or combination of genotypes of the initial cultivar or variety. Essentially derived varieties can be obtained, for example, by the selection of a natural or induced mutant, a somaclonal variant, a variant individual from plants of the initial cultivar or variety, backcrossing, or transformation. A "line" as distinguished from a cultivar or variety most often denotes a group of plants used non-commercially, for example in plant research. A line typically displays little overall variation between individuals for one or more traits of interest, although there may be some variation between individuals for other traits.

Hybrid tobacco varieties can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In aspects in which the female parent plants are CMS, pollen may be harvested from male fertile plants and applied manually to the stigmas of CMS female parent plants, and the resulting $F_1$ seed is harvested.

Plants can be used to form single-cross tobacco $F_1$ hybrids. In such an aspect, the plants of the parent varieties can be grown as substantially homogeneous adjoining populations to facilitate natural cross-pollination from the male parent plants to the female parent plants. The $F_1$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

Successful crosses yield $F_1$ plants that are fertile, have cyp82e4 W329Stop, cyp82e5v2 W422Stop, and cyp82e10 P381S alleles, and can be backcrossed with one of the parents, such as Banket A1 SRC, CMS Banket A1 SRC, NC 2000 SRC, CMS NC 2000 SRC, NC 2002 SRC, CMS NC 2002 SRC, Burley 21 SRC, or CMS Burley 21 SRC, if desired. In some aspects, a plant population in the $F_2$ generation is screened for cyp82e4 W329Stop, the cyp82e5v2 W422Stop, and cyp82e10 P381S alleles. Selected plants can be crossed with one of the parents and the first backcross (BC1) generation plants are self-pollinated to produce a BC1 $F_2$ population that is again screened for variant nicotine demethylase gene expression (e.g., the null version of the nicotine demethylase gene). The process of backcrossing, self-pollination, and screening is repeated, for example, at least four times, until the final screening produces a plant that is fertile and reasonably similar to the recurrent parent. This plant, if desired, is self-pollinated and the progeny are subsequently screened again to confirm that the plant exhibits the same low nicotine conversion phenotype as Banket A1 SRC, CMS Banket A1 SRC, NC 2000 SRC, CMS NC 2000 SRC, NC 2002 SRC, CMS NC 2002 SRC, Burley 21 SRC, or CMS Burley 21 SRC. Breeder's seed of the selected plant is produced using standard methods including, for example, field testing, confirmation of the null condition for nicotine demethylase, chemical analyses of cured leaf to determine the level of alkaloids and/or chemical analyses of cured leaf to determine the ratio of nornicotine to nicotine+nornicotine.

In one aspect, an $F_1$ progeny is the result of a cross between Banket A1 SRC and CMS Banket A1 SRC, between NC 2000 SRC and CMS NC 2000 SRC, between NC 2002 SRC and CMS NC 2002 SRC, or between Burley 21 SRC and CMS Burley 21 SRC to generate $F_1$ progeny that are male sterile. Male sterile tobacco plants may be produced by any method known in the art. Methods of producing male sterile tobacco are described in Wernsman, E. A., and Rufty, R. C., 1987. Chapter Seventeen. Tobacco. pages 669-698 In: Cultivar Development. Crop Species. W. H. Fehr (ed.), MacMillan Publishing Go., Inc., New York, N.Y. 761 pp.

The present disclosure further provides methods of producing a tobacco plant by crossing one of cultivars Banket A1 SRC, CMS Banket A1 SRC, NC 2000 SRC, CMS NC 2000 SRC, NC 2002 SRC, CMS NC 2002 SRC, Burley 21 SRC, or CMS Burley 21 SRC with itself or a different tobacco line. The disclosure further relates to methods for producing other tobacco cultivars or breeding lines derived from cultivars Banket A1 SRC, CMS Banket A1 SRC, NC 2000 SRC, CMS NC 2000 SRC, NC 2002 SRC, CMS NC 2002 SRC, Burley 21 SRC, or CMS Burley 21 SRC by crossing a plant of cultivars Banket A1 SRC, CMS Banket A1 SRC, NC 2000 SRC, CMS NC 2000 SRC, NC 2002 SRC, CMS NC 2002 SRC, Burley 21 SRC, or CMS Burley 21 SRC with a second tobacco plant and growing the progeny seed to yield a Banket A1 SRC, CMS Banket A1 SRC, NC 2000 SRC, CMS NC 2000 SRC, NC 2002 SRC, CMS NC 2002 SRC, Burley 21 SRC, or CMS Burley 21 SRC—derived tobacco plant. An additional aspect of the present disclosure provides a method for producing a tobacco plant that contains in its genetic material one or more transgenes, comprising crossing cultivars of the present disclosure with a second cultivar containing one or more transgenes wherein progeny are produced, so that the genetic material of the progeny that result from the cross comprise the transgene(s) optionally operably linked to one or more regulatory elements. In one aspect, the second cultivar may be a plant derived from cultivars Banket A1 SRC, CMS Banket A1 SRC, NC 2000 SRC, CMS NC 2000 SRC, NC 2002 SRC, CMS NC 2002 SRC, Burley 21 SRC, or CMS Burley 21 SRC transformed with one or more transgenes.

The disclosure further provides for the vegetative propagation of a plant of cultivars Banket A1 SRC, CMS Banket A1 SRC, NC 2000 SRC, CMS NC 2000 SRC, NC 2002 SRC, CMS NC 2002 SRC, Burley 21 SRC, or CMS Burley 21 SRC and progeny thereof. In one aspect, the disclosure provides for a method of vegetatively propagating a plant of a tobacco cultivar comprising collecting tissue capable of being propagated from a plant of cultivars Banket A1 SRC, CMS Banket A1 SRC, NC 2000 SRC, CMS NC 2000 SRC, NC 2002 SRC, CMS NC 2002 SRC, Burley 21 SRC, or CMS Burley 21 SRC, cultivating the tissue to obtain a proliferated shoot and rooting the proliferated shoots to obtain a rooted plantlet. In another aspect, the plant tissue may be collected from an $F_1$ hybrid of a plant of cultivars Banket A1 SRC, CMS Banket A1 SRC, NC 2000 SRC, CMS NC 2000 SRC, NC 2002 SRC, CMS NC 2002 SRC, Burley 21 SRC, or CMS Burley 21 SRC. In an aspect, the plant tissue may be collected from an $F_2$, $F_3$, $F_4$ or later progeny plant obtained by breeding a plant of cultivars Banket A1 SRC, CMS Banket A1 SRC, NC 2000 SRC, CMS NC 2000 SRC, NC 2002 SRC, CMS NC 2002 SRC, Burley 21 SRC, or CMS Burley 21 SRC.

A plant comprising a mutation in a nicotine demethylase gene can be identified by selecting or screening the mutagenized plant material, or progeny thereof. Such screening and selection methodologies are known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

It is understood that a tobacco plant of the present disclosure, including, but not limited to, Banket A1 SRC, CMS Banket A1 SRC, NC 2000 SRC, CMS NC 2000 SRC, NC 2002 SRC, CMS NC 2002 SRC, Burley 21 SRC, and CMS Burley 21 SRC, can be transformed by a genetic construct (nucleic acid construct) or transgene using any technique known in the art. Without limitation, an example of a desired trait can include herbicide resistance, pest resistance, disease resistance, high yield, high grade index, curability, curing quality, mechanical harvestability, holding ability, leaf quality, height, plant maturation (e.g., early maturing, early to medium maturing, medium maturing, medium to late maturing, or late maturing), stalk size (e.g., small, medium, or large stalk), or leaf number per plant (e.g., small (e.g., 5-10 leaves), medium (e.g., 11-15 leaves), or large (e.g., 16-21) number of leaves), or any combination. Any plant of the present disclosure can be used as a basis for tissue culture, regeneration, transformed, or a combination of any of these. In an aspect, a plant of the present disclosure derived by tissue culture, transformation, or both has all, or essentially all, of the morphological and physiological characteristics of cultivar Banket A1 SRC, CMS Banket A1 SRC, NC 2000 SRC, CMS NC 2000 SRC, NC 2002 SRC, CMS NC 2002 SRC, Burley 21 SRC, or CMS Burley 21 SRC.

Having now generally described the disclosure, the same will be more readily understood through reference to the following examples that are provided by way of illustration, and are not intended to be limiting of the present disclosure, unless specified.

EXAMPLES

Example 1

Breeding of Homozygous cyp82e4 W329Stop, the cyp82e5v2 W422Stop, and cyp82e10 P381S Mutant Plants into the Banket A1 Burley Tobacco Cultivar Banket A1 SRC is a backcross-derived version of burley tobacco cultivar Banket A1 carrying introduced mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., Phytochemistry, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN), a potent carcinogen found in many tobacco products. The mutation in CYP82E4 (cyp82e4 W329Stop (SEQ ID NO: 1)) also provides phenotypic stability for the "nicotine conversion" trait and eliminates the requirement to utilize the cumbersome "LC" method for reducing levels of nornicotine in tobacco cultivars (see e.g., Jack et al. 2007. Implications of reducing nornicotine accumulation in burley tobacco: appendix A—the LC protocol. *Rec. Adv. Tob. Sci.* 33: 58-79).

The original tobacco cultivar Banket A1 is a fertile inbred line. CMS Banket A1 is a cytoplasmic male-sterile version of Banket A1. To develop Banket A1 SRC, an individual plant of Banket A1 is pollinated with a plant of the genetic background DH98-325-6 carrying mutations in each of the three nicotine demethylase genes. $F_1$ individuals originating from this cross and heterozygous for each mutation are backcrossed to the recurrent parent, Banket A1, to produce $BC_1F_1$ progeny. $BC_1F_1$ progeny are screened using genotyping methodologies to identify individuals heterozygous for all three mutations. A single triple heterozygous $BC_1F_1$ plant is backcrossed to Banket A1 to produce $BC_2F_1$ progeny. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. A single $BC_7F_2$ plant homozygous for all three mutations is self-pollinated to produce a $BC_7F_3$ family (Banket A1 SRC) in which the wild-type CYP82E4, CYP82E5v2, and CYP82E10 alleles of Banket A1 were replaced by the mutant alleles (cyp82e4 W329Stop, cyp82e5v2 W422Stop, and cyp82e10 P381S).

The male-sterile (CMS) version of Banket A1 SRC (CMS Banket A1 SRC) is produced by crossing a plant of CMS Banket A1 as a female with pollen of Banket A1 SRC to produce male-sterile plants heterozygous for all three mutations. A single male-sterile plant resulting from this cross is then subsequently backcrossed as a female to Banket A1 SRC to produce progeny that are segregating for individuals homozygous for all three mutations. Triple homozygous individuals are identified by DNA genotyping to produce the CMS Banket A1 SRC line. Because the line is male-sterile, it is maintained via pollination with Banket A1 SRC.

Commercial Banket A1 SRC is produced by pollinating plants of CMS Banket A1 SRC with pollen of Banket A1 SRC.

Example 2

Testing of Banket A1 SRC

Banket A1 SRC is evaluated for cured leaf chemistry, yield, and physical quality at three North Carolina field research locations during 2013 (Reidsville and Waynesville). Banket A1 is included for comparison. The experimental design at each location is a randomized complete block design with four replications. Experimental units are single 20-plant plots. Plots are harvested and air-cured. Plot weights are used to determine per acre yields. Cured leaf is evaluated by a former USDA tobacco grader. Fifty gram composite leaf samples are collected from each plot and analyzed for percent nicotine, nornicotine, anatabine, anabasine, and percent nicotine conversion using gas chromatography equipment.

Comparisons using the least significant difference (LSD) test indicates that Banket A1 SRC has significantly (P<0.05) lower levels of nornicotine and percent nicotine conversion relative to Banket A1 (Table 1). Banket A1 and Banket A1 SRC are not significantly different from each other for percent nicotine, yield, percent anabasine, percent anatabine, or percent total alkaloids.

Example 3

Breeding of Homozygous cyp82e4 W329Stop, the cyp82e5v2 W422Stop, and cyp82e10 P381S Mutant Plants into the NC 2000 Burley Tobacco Cultivar NC 2000 SRC is a backcross-derived version of burley tobacco cultivar NC 2000 carrying introduced mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., Phytochemistry, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381 S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN), a potent carcinogen found in many tobacco products. The mutation in CYP82E4 (cyp82e4 W329Stop (SEQ ID NO: 1)) also provides phenotypic stability for the "nicotine conversion" trait and eliminates the requirement to utilize the cumbersome "LC" method for reducing levels of nornicotine in tobacco cultivars (see e.g., Jack et al. 2007. Implications of reducing nornicotine accumulation in burley tobacco: appendix A—the LC protocol. Rec. Adv. Tob. Sci. 33: 58-79).

The original tobacco cultivar NC 2000 is a fertile inbred line. CMS NC 2000 is a cytoplasmic male-sterile version of NC 2000. To develop NC 2000 SRC, an individual plant of NC 2000 is pollinated with a plant of the genetic background DH98-325-6 carrying mutations in each of the three nicotine demethylase genes. $F_1$ individuals originating from this cross and heterozygous for each mutation are backcrossed to the recurrent parent, NC 2000, to produce $BC_1F_1$ progeny. $BC_1F_1$ progeny are screened using genotyping methodologies to identify individuals heterozygous for all three mutations. A single triple heterozygous $BC_1F_1$ plant is backcrossed to NC 2000 to produce $BC_2F_1$ progeny. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. A single $BC_7F_2$ plant homozygous for all three mutations is self-pollinated to produce a $BC_7F_3$ family (NC 2000 SRC) in which the wild-type CYP82E4, CYP82E5v2, and CYP82E10 alleles of NC 2000 were replaced by the mutant alleles (cyp82e4 W329Stop, cyp82e5v2 W422Stop, and cyp82e10 P381S).

The male-sterile (CMS) version of NC 2000 SRC (CMS NC 2000 SRC) is produced by crossing a plant of CMS NC 2000 as a female with pollen of NC 2000 SRC to produce male-sterile plants heterozygous for all three mutations. A single male-sterile plant resulting from this cross is then subsequently backcrossed as a female to NC 2000 SRC to produce progeny that are segregating for individuals homozygous for all three mutations. Triple homozygous individuals are identified by DNA genotyping to produce the CMS NC 2000 SRC line. Because the line is male-sterile, it is maintained via pollination with NC 2000 SRC.

Commercial NC 2000 SRC is produced by pollinating plants of CMS NC 2000 SRC with pollen of NC 2000 SRC.

Example 4

Testing of NC 2000 SRC

NC 2000 SRC is evaluated for cured leaf chemistry, yield, and physical quality at two North Carolina field research locations during 2013 (Reidsville and Waynesville). NC 2000 is included for comparison. The experimental design at each location is a randomized complete block design with four replications. Experimental units are single 20-plant plots. Plots are harvested and air-cured. Plot weights are used to determine per acre yields. Cured leaf is evaluated by a former USDA tobacco grader. Fifty gram composite leaf samples are collected from each plot and analyzed for percent nicotine, nornicotine, anatabine, anabasine, and percent nicotine conversion using gas chromatography equipment.

Comparisons using the least significant difference (LSD) test indicates that NC 2000 SRC has significantly (P<0.05) lower levels of nornicotine and percent nicotine conversion relative to NC 2000 (Table 2). NC 2000 and NC 2000 SRC are not significantly different from each other for percent nicotine, yield, percent anabasine, percent anatabine, or percent total alkaloids.

Example 5

Breeding of Homozygous cyp82e4 W329Stop, the cyp82e5v2 W422Stop, and cyp82e10 P381S Mutant Plants into the NC 2002LC Burley Tobacco Cultivar NC 2002 SRC is a backcross-derived version of burley tobacco cultivar NC 2002LC carrying introduced mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., Phytochemistry, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN), a potent carcinogen found in many tobacco products. The mutation in CYP82E4 (cyp82e4 W329Stop (SEQ ID NO: 1)) also provides phenotypic stability for the "nicotine conversion" trait and eliminates the requirement to utilize the cumbersome "LC" method for reducing levels of nornicotine in tobacco cultivars (see e.g., Jack et al. 2007. Implications of reducing nornicotine accumulation in burley tobacco: appendix A—the LC protocol. *Rec. Adv. Tob. Sci.* 33: 58-79).

The original tobacco cultivar NC 2002LC is a fertile inbred line. CMS NC 2002LC is a cytoplasmic male-sterile version of NC 2002LC. To develop NC 2002 SRC, an individual plant of NC 2002LC is pollinated with a plant of the genetic background DH98-325-6 carrying mutations in each of the three nicotine demethylase genes. $F_1$ individuals originating from this cross and heterozygous for each mutation are backcrossed to the recurrent parent, NC 2002LC, to produce $BC_1F_1$ progeny. $BC_1F_1$ progeny are screened using genotyping methodologies to identify individuals heterozygous for all three mutations. A single triple heterozygous $BC_1F_1$ plant is backcrossed to NC 2002LC to produce $BC_2F_1$ progeny. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. A single $BC_7F_2$ plant homozygous for all three mutations is self-pollinated to produce a $BC_7F_3$ family (NC 2002 SRC) in which the wild-type CYP82E4, CYP82E5v2, and CYP82E10 alleles of NC 2002LC were replaced by the mutant alleles (cyp82e4 W329Stop, cyp82e5v2 W422Stop, and cyp82e10 P381S).

The male-sterile (CMS) version of NC 2002 SRC (CMS NC 2002 SRC) is produced by crossing a plant of CMS NC 2002LC as a female with pollen of NC 2002 SRC to produce male-sterile plants heterozygous for all three mutations. A single male-sterile plant resulting from this cross is then subsequently backcrossed as a female to NC 2002 SRC to produce progeny that are segregating for individuals homozygous for all three mutations. Triple homozygous individuals are identified by DNA genotyping to produce the CMS NC 2002 SRC line. Because the line is male-sterile, it is maintained via pollination with NC 2002 SRC.

Commercial NC 2002 SRC is produced by pollinating plants of CMS NC 2002 SRC with pollen of NC 2002 SRC.

Example 6

Testing of NC 2002 SRC

NC 2002 SRC is evaluated for cured leaf chemistry, yield, and physical quality at two North Carolina field research locations during 2013 (Reidsville and Waynesville). NC 2002LC is included for comparison. The experimental design at each location is a randomized complete block design with four replications. Experimental units are single 20-plant plots. Plots are harvested and air-cured. Plot weights are used to determine per acre yields. Cured leaf is evaluated by a former USDA tobacco grader. Fifty gram composite leaf samples are collected from each plot and analyzed for percent nicotine, nornicotine, anatabine, anabasine, and percent nicotine conversion using gas chromatography equipment.

Comparisons using the least significant difference (LSD) test indicates that NC 2002 SRC has significantly (P<0.05) lower levels of nornicotine and percent nicotine conversion relative to NC 2002LC (Table 2). NC 2002LC and NC 2002 SRC are not significantly different from each other for percent nicotine, yield, percent anabasine, percent anatabine, or percent total alkaloids.

Example 7

Breeding of Homozygous cyp82e4 W329Stop, the cyp82e5v2 W422Stop, and cyp82e10 P381S Mutant Plants into the Burley 21 SRC Burley Tobacco Cultivar Burley 21 SRC is a backcross-derived version of burley tobacco cultivar Burley 21 SRC carrying introduced mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., *Phytochemistry*, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN), a potent carcinogen found in many tobacco products. The mutation in CYP82E4 (cyp82e4 W329Stop (SEQ ID NO: 1)) also provides phenotypic stability for the "nicotine conversion" trait and eliminates the requirement to utilize the cumbersome "LC" method for reducing levels of nornicotine in tobacco cultivars (see e.g., Jack et al. 2007. Implications of reducing nornicotine accumulation in burley tobacco: appendix A—the LC protocol. *Rec. Adv. Tob. Sci.* 33: 58-79).

The original tobacco cultivar Burley 21 SRC is a fertile inbred line. CMS Burley 21 is a cytoplasmic male-sterile version of Burley 21 SRC. To develop Burley 21 SRC, an individual plant of Burley 21 SRC is pollinated with a plant of the genetic background DH98-325-6 carrying mutations in each of the three nicotine demethylase genes. $F_1$ individuals originating from this cross and heterozygous for each mutation are backcrossed to the recurrent parent, Burley 21 SRC, to produce $BC_1F_1$ progeny. $BC_1F_1$ progeny are screened using genotyping methodologies to identify individuals heterozygous for all three mutations. A single triple heterozygous $BC_1F_1$ plant is backcrossed to Burley 21 SRC to produce $BC_2F_1$ progeny. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. A single $BC_7F_2$ plant homozygous for all three mutations is self-pollinated to produce a $BC_7F_3$ family (Burley 21 SRC) in which the wild-type CYP82E4, CYP82E5v2, and CYP82E10 alleles of Burley 21 SRC were replaced by the mutant alleles (cyp82e4 W329Stop, cyp82e5v2 W422Stop, and cyp82e10 P381S).

The male-sterile (CMS) version of Burley 21 SRC (CMS Burley 21 SRC) is produced by crossing a plant of CMS Burley 21 as a female with pollen of Burley 21 SRC to produce male-sterile plants heterozygous for all three mutations. A single male-sterile plant resulting from this cross is then subsequently backcrossed as a female to Burley 21 SRC to produce progeny that are segregating for individuals homozygous for all three mutations. Triple homozygous individuals are identified by DNA genotyping to produce the CMS Burley 21 SRC line. Because the line is male-sterile, it is maintained via pollination with Burley 21 SRC.

Commercial Burley 21 SRC is produced by pollinating plants of CMS Burley 21 SRC with pollen of Burley 21 SRC.

Example 8

Testing of Burley 21 SRC

Burley 21 SRC is evaluated for cured leaf chemistry, yield, and physical quality at two North Carolina field research locations during 2013 (Reidsville and Waynesville). Burley 21 SRC is included for comparison. The experimental design at each location is a randomized complete block design with four replications. Experimental units are single 20-plant plots. Plots are harvested and air-cured. Plot weights are used to determine per acre yields. Cured leaf is evaluated by a former USDA tobacco grader. Fifty gram composite leaf samples are collected from each plot and analyzed for percent nicotine, nornicotine, anatabine, anabasine, and percent nicotine conversion using gas chromatography equipment.

Comparisons using the least significant difference (LSD) test indicates that Burley 21 SRC has significantly (P<0.05) lower levels of nornicotine and percent nicotine conversion relative to Burley 21 SRC (Table 1). Burley 21 SRC and Burley 21 SRC are not significantly different from each other for percent nicotine, yield, percent anabasine, percent anatabine, or percent total alkaloids.

TABLE 1

Entry means for experiment EX14-157 entries evaluated in two 2013 North Carolina environments (Reidsville and Waynesville).

| Variety | Yield (lbs/A) | Grade Index | Nicotine (%) | Nornicotine (%) | Anabasine (%) | Anatabine (%) | Total Alkaloids (%) | Nicotine Conversion (%) |
|---|---|---|---|---|---|---|---|---|
| Banket A1 | 2071 | 72.4 | 2.757 | 0.049 | 0.017 | 0.258 | 3.081 | 1.796 |
| Banket A1 SRC | 1948 | 72.2 | 3.214 | 0.018* | 0.019 | 0.284 | 3.535 | 0.594* |
| Burley 21 | 1985 | 72.7 | 2.250 | 0.060 | 0.012 | 0.174 | 2.495 | 2.649 |
| Burley 21 SRC | 1897 | 74.7 | 2.881 | 0.018* | 0.014 | 0.218 | 3.130 | 0.631* |
| NC 3LC | 2168 | 73.9 | 1.921 | 0.117 | 0.012 | 0.180 | 2.230 | 5.523 |
| NC 3 SRC | 2097 | 75.9 | 2.154 | 0.011* | 0.011 | 0.175 | 2.351 | 0.504* |
| NC 4 SRC | 2143 | 74.6 | 2.395 | 0.013* | 0.012 | 0.217 | 2.637 | 0.554* |
| NC 6LC | 2275 | 75.7 | 2.093 | 0.221 | 0.012 | 0.204 | 2.530 | 8.965 |
| NC 6 SRC | 2245 | 72.1 | 2.380 | 0.010* | 0.012 | 0.199 | 2.601 | 0.431* |
| DH98-325-5 | 2187 | 72.1 | 2.066 | 0.045 | 0.012 | 0.200 | 2.323 | 2.205 |
| DH98-325-5 SRC | 2086 | 72.5 | 2.332 | 0.013* | 0.012 | 0.205 | 2.562 | 0.533* |
| DH19 | 1898 | 70.7 | 1.854 | 0.044 | 0.011 | 0.158 | 2.066 | 2.257 |
| DH19 SRC | 2242 | 72.5 | 1.870 | 0.018* | 0.012 | 0.159 | 2.058 | 0.998* |
| NC1426-17 | 1924 | 71.8 | 1.802 | 0.046 | 0.012 | 0.211 | 2.072 | 2.565 |
| NC1426-17 SRC | 2056 | 75.2 | 2.030 | 0.012* | 0.012 | 0.214 | 2.269 | 0.614* |
| NC1426-11 | 2415 | 71.2 | 2.228 | 0.078 | 0.013 | 0.232 | 2.551 | 3.513 |
| NC1426-11 SRC | 2056* | 75.4* | 2.121 | 0.011* | 0.011 | 0.181* | 2.324 | 0.524* |
| VA 509LC | 1975 | 72.9 | 2.197 | 0.169 | 0.013 | 0.187 | 2.567 | 7.107 |
| Ky 14 LC | 2237 | 74.2 | 2.151 | 0.072 | 0.012 | 0.209 | 2.444 | 3.407 |

Banket A1 is a fertile burley inbred variety. Banket A1 SRC is a backcross-derived version of Banket A1 carrying introduced mutations in three genes (cyp82e4 W329Stop, cyp82e5v2 W422Stop, and cyp82e10 P381S).
Burley 21 is a fertile burley inbred variety. Burley 21 SRC is a backcross-derived version of Burley 21 carrying introduced mutations in three genes (cyp82e4 W329Stop, cyp82e5v2 W422Stop, and cyp82e10 P381S).
Tobacco cultivar NC 3LC is a hybrid generated by pollinating plants of a male-sterile breeding line CMS NC1209-23 with pollen produced by fertile breeding line DH19. Tobacco cultivar NC 3 SRC is a hybrid generated by pollinating plants of a male-sterile breeding line CMS NC1209-23 SRC with pollen produced by fertile breeding line DH19 SRC.
Tobacco cultivar NC 4 SRC is a hybrid generated by pollinating plants of a male-sterile breeding line CMS NC1426-11 SRC with pollen produced by fertile breeding line NC1426-17 SRC. Tobacco cultivar NC 6LC is a hybrid generated by pollinating plants of a male-sterile breeding line CMS NC1209-23 with pollen produced by fertile breeding line DH98-325-5.
Tobacco cultivar NC 6 SRC is a hybrid generated by pollinating plants of a male-sterile breeding line CMS NC1209-23 SRC with pollen produced by fertile breeding line DH98-325-5 SRC.
DH98-325-5 is a fertile burley inbred variety. DH98-325-5 SRC is a backcross-derived version of DH98-325-5 carrying introduced mutations in three genes (cyp82e4 W329Stop, cyp82e5v2 W422Stop, and cyp82e10 P381S).
DH 19 is a fertile burley inbred variety. DH 19 SRC is a backcross-derived version of DH 19 carrying introduced mutations in three genes (cyp82e4 W329Stop, cyp82e5v2 W422Stop, and cyp82e10 P381S).
NC1426-17 is a fertile burley inbred variety. NC1426-17 SRC is a backcross-derived version of NC1426-17 carrying introduced mutations in three genes (cyp82e4 W329Stop, cyp82e5v2 W422Stop, and cyp82e10 P381S).
NC1426-11 is a fertile burley inbred variety. NC1426-11 SRC is a backcross-derived version of NC1426-11 carrying introduced mutations in three genes (cyp82e4 W329Stop, cyp82e5v2 W422Stop, and cyp82e10 P381S).
KY 14 LC and VA 509 LC are LC-selected burley tobacco varieties KY 14 and VA 509.
*Indicates significantly different (P < 0.05) from the nearly isogenic LC variety or regular breeding line. Significance tests were based upon log transformed valued for % nicotine, % nornicotine, % anabasine, % anatabine, and % nicotine conversion. Significance tests were based upon non-transformed values for the remainder of the measured characteristics.

TABLE 2

Entry means for experiment EX13-158 entries evaluated in two 2013 North Carolina environments (Reidsville and Waynesville).

| Variety | Yield (lbs/A) | Grade Index | Nicotine (%) | Nornicotine (%) | Anabasine (%) | Anatabine (%) | Total Alkaloids (%) | Nicotine Conversion (%) |
|---|---|---|---|---|---|---|---|---|
| NC 174 | 1769 | 65.2 | 2.180 | 0.061 | 0.012 | 0.167 | 2.420 | 2.689 |
| NC 174 SRC | 1489 | 67.7 | 1.606* | 0.013* | 0.010 | 0.117* | 1.746 | 0.826* |
| NC821-11 | 1671 | 66.6 | 1.708 | 0.045 | 0.012 | 0.241 | 2.005 | 2.658 |

TABLE 2-continued

Entry means for experiment EX13-158 entries evaluated in two 2013 North Carolina environments (Reidsville and Waynesville).

| Variety | Yield (lbs/A) | Grade Index | Nicotine (%) | Nornicotine (%) | Anabasine (%) | Anatabine (%) | Total Alkaloids (%) | Nicotine Conversion (%) |
|---|---|---|---|---|---|---|---|---|
| NC821-11 SRC | 1588 | 66.5 | 1.535 | 0.013* | 0.010 | 0.170* | 1.728 | 0.803* |
| NC 2000LC | 1750 | 71.5 | 2.651 | 0.076 | 0.015 | 0.230 | 2.973 | 2.834 |
| NC 2000 SRC | 1652 | 68.9 | 2.914 | 0.021* | 0.017 | 0.238 | 3.191 | 0.705* |
| NC 2002LC | 1722 | 71.9 | 2.143 | 0.091 | 0.014 | 0.191 | 2.439 | 4.280 |
| NC 2002 SRC | 1596 | 69.0 | 1.856 | 0.015* | 0.009* | 0.127* | 2.007 | 0.788* |
| NC 5LC | 1769 | 65.7 | 1.575 | 0.123 | 0.011 | 0.170 | 1.879 | 7.363 |
| NC 5 SRC | 1897 | 66.5 | 1.701 | 0.014* | 0.010 | 0.155 | 1.880 | 0.781* |
| NC 645 | 1919 | 72.9 | 2.134 | 0.078 | 0.012 | 0.177 | 2.402 | 3.226 |
| NC645 BmrBmr SRC | 1748 | 72.1 | 2.717 | 0.024* | 0.014 | 0.225 | 2.980 | 0.892* |
| NC 775 | 1741 | 69.2 | 1.938 | 0.123 | 0.012 | 0.151 | 2.224 | 6.004 |
| NC 775 BmrBmr SRC | 1805 | 69.3 | 2.008 | 0.014* | 0.011 | 0.156 | 2.189 | 0.716* |
| NC 8 SRC | 1845 | 69.3 | 2.432 | 0.020* | 0.013 | 0.191 | 2.657 | 0.857* |
| Ky 14LC | 1847 | 68.0 | 1.833 | 0.043 | 0.012 | 0.156 | 2.044 | 2.216 |
| VA 509LC | 1756 | 69.8 | 2.145 | 0.079 | 0.013 | 0.167 | 2.404 | 3.642 |

NC 174 is a fertile burley inbred variety. NC 174 SRC is a backcross-derived version of NC 174 carrying introduced mutations in three genes (cyp82e4 W329Stop, cyp82e5v2 W422Stop, and cyp82e10 P381S).
NC821-11 is a fertile burley inbred variety. NC821-11 SRC is a backcross-derived version of NC821-11 carrying introduced mutations in three genes (cyp82e4 W329Stop, cyp82e5v2 W422Stop, and cyp82e10 P381S).
NC 2000LC is a LC-selected fertile burley inbred variety NC 2000. NC 2000 SRC is a backcross-derived version of NC 2000 carrying introduced mutations in three genes (cyp82e4 W329Stop, cyp82e5v2 W422Stop, and cyp82e10 P381S).
NC 2002LC is a LC-selected fertile burley inbred variety NC 2002. NC 2002 SRC is a backcross-derived version of NC 2002 carrying introduced mutations in three genes (cyp82e4 W329Stop, cyp82e5v2 W422Stop, and cyp82e10 P381S).
Tobacco cultivar NC 5LC is a hybrid generated by pollinating plants of a male-sterile breeding line CMS NC174 with pollen produced by fertile breeding line NC821-11. Tobacco cultivar NC 5 SRC is a hybrid generated by pollinating plants of a male-sterile breeding line CMS NC174 SRC with pollen produced by fertile breeding line NC821-11 SRC.
NC 645 is a fertile burley inbred variety. NC645 BmrBmr SRC is a backcross-derived version of NC645 carrying introduced mutations in three genes (cyp82e4 W329Stop, cyp82e5v2 W422Stop, and cyp82e10 P381S) and homozygous for an introduced major blue mold resistance gene designated as Bmr.
NC 775 is a fertile burley inbred variety. NC775 BmrBmr SRC is a backcross-derived version of NC775 carrying introduced mutations in three genes (cyp82e4 W329Stop, cyp82e5v2 W422Stop, and cyp82e10 P381S) and homozygous for an introduced major blue mold resistance gene designated as Bmr.
Hybrid cultivar NC 8 SRC is produced by pollinating plants of CMS NC775 Bmr/Bmr SRC with pollen of NC645 Bmr/Bmr SRC.
KY 14LC and VA 509LC are LC-selected burley tobacco varieties KY 14 and VA 509, respectively.
*Indicates significantly different (P < 0.05) from the nearly isogenic LC variety or regular breeding line. Significance tests are based upon log transformed valued for % nicotine, % nornicotine, % anabasine, % anatabine, and % nicotine conversion. Significance tests are based upon non-transformed values for the remainder of the measured characteristics.

DEPOSIT INFORMATION

A deposit of the proprietary inbred plant lines disclosed above and recited in the appended claims have been made with American Type Culture Collection (ATCC), 10801 University Boulevard, Manassas, Va. 20110. The date of deposit for Banket A1 SRC, CMS Banket A1 SRC, NC 2000 SRC, CMS NC 2000 SRC, NC 2002 SRC, CMS NC 2002 SRC, Burley 21 SRC, and CMS Burley 21 SRC was Feb. 26, 2014. The deposits of 2500 seeds for each variety was taken from the same deposits maintained since prior to the filing date of this application. Upon issuance of a patent, all restrictions upon the deposits will be irrevocalbly removed, and the deposits are intended by Application to meet all of the requirements of 37 C.F.R. §1.801-1.809. The ATCC has issued the following accession numbers: PTA-121043 for Banket A1 SRC, PTA-121054 for CMS Banket A1 SRC, PTA-121053 for NC 2000 SRC, PTA-121045 for CMS NC 2000 SRC, PTA-121058 for NC 2002 SRC, PTA-121041 for CMS NC 2002 SRC, PTA-121059 for Burley 21 SRC, and PTA-121044 for CMS Burley 21 SRC. These deposits will be maintained in the depository for a period of 30 years, or 5 years after the last request, or for the effective life of the patent, whichever is longer, and will be replaced as necessary during that period. Applicants do not waive any infringement of their rights granted under this patent or under the Plant Variety Protection Act (7 U.S.C. 2321 et seq.).

What is claimed is:

1. Cured tobacco or a tobacco product prepared therefrom,
wherein said cured tobacco is from a tobacco plant of a cultivar or a hybrid produced from said cultivar,
wherein said cultivar is selected from the group consisting of Banket A1 SRC, CMS Banket A1 SRC, NC 2000 SRC, CMS NC 2000 SRC, NC 2002 SRC, CMS NC 2002 SRC, Burley 21 SRC, and CMS Burley 21 SRC;
and wherein representative sample seeds of said Banket A1 SRC, CMS Banket A1 SRC, NC 2000 SRC, CMS NC 2000 SRC, NC 2002 SRC, CMS NC 2002 SRC, Burley 21 SRC, and CMS Burley 21 SRC have been deposited at the ATCC with the following ATCC Accession Nos.: PTA-121043 for Banket A1 SRC, PTA-121054 for CMS Banket A1 SRC, PTA-121053 for NC 2000 SRC, PTA-121045 for CMS NC 2000 SRC, PTA-121058 for NC 2002 SRC, PTA-121041 for CMS NC 2002 SRC, PTA-121059 for Burley 21 SRC, and PTA-121044 for CMS Burley 21 SRC, wherein said hybrid comprises essentially all of the morphological and physiological characteristics of the corresponding deposited cultivar used to produce said progeny hybrid.

2. The tobacco product of claim 1, wherein said tobacco product is selected from the group consisting of a tobacco blend, a pipe tobacco, a cigar tobacco, a cigarette tobacco, a chewing tobacco, a leaf tobacco, a shredded tobacco, and a cut tobacco.

3. The tobacco product of claim 1, wherein said tobacco product is selected from the group consisting of a cigarillo, a non-ventilated recess filter cigarette, a vented recess filter cigarette, a cigar, snuff, and a chewing tobacco.

4. The tobacco product of claim 3, wherein said tobacco product has an amount of nornicotine of less than about 3 mg/g.

5. The tobacco product of claim 4, wherein said amount of nornicotine is selected from the group consisting of 3.0 mg/g, 2.5 mg/g, 2.0 mg/g, 1.5 mg/g, 1.0 mg/g, 750 µg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, and undetectable.

6. The tobacco product of claim 3, wherein said tobacco product has an amount of N'-nitrosonornicotine (NNN) of less than about 10 pg/g.

7. The tobacco product of claim 6, wherein said amount of NNN is selected from the group consisting of 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, and undetectable.

8. The tobacco product of claim 1, wherein said cured tobacco is at least about 5% by dry weight of the total tobacco in said tobacco product.

9. The tobacco product of claim 8, wherein said cured tobacco has a dry weight percentage of said total cured tobacco selected from the group consisting of at least about 10%, at least about 20%, at least about 30%, at least about 40%, at least about 50%, at least about 60%, at least about 70%, at least about 80%, at least about 90%, and at least about 95%.

10. A method of producing a tobacco product, comprising:
a. providing cured tobacco from a tobacco plant of a cultivar or a progeny hybrid produced from said cultivar, wherein said cultivar is selected from the group consisting of Banket A1 SRC, CMS Banket A1 SRC, NC 2000 SRC, CMS NC 2000 SRC, NC 2002 SRC, CMS NC 2002 SRC, Burley 21 SRC, and CMS Burley 21 SRC;
b. preparing a tobacco product from said cured tobacco, wherein representative sample seeds of said Banket A1 SRC, CMS Banket A1 SRC, NC 2000 SRC, CMS NC 2000 SRC, NC 2002 SRC, CMS NC 2002 SRC, Burley 21 SRC, and CMS Burley 21 SRC have been deposited at the ATCC with the following ATCC Accession Nos.: PTA-121043 for Banket A1 SRC, PTA-121054 for CMS Banket A1 SRC, PTA-121053 for NC 2000 SRC, PTA-121045 for CMS NC 2000 SRC, PTA-121058 for NC 2002 SRC, PTA-121041 for CMS NC 2002 SRC, PTA-121059 for Burley 21 SRC, and PTA-121044 for CMS Burley 21 SRC, wherein said progeny hybrid comprises essentially all of the morphological and physiological characteristics of the corresponding deposited cultivar used to produce said progeny hybrid.

11. A seed of tobacco cultivar selected from the group consisting of Banket A1 SRC, CMS Banket A1 SRC, NC 2000 SRC, CMS NC 2000 SRC, NC 2002 SRC, CMS NC 2002 SRC, Burley 21 SRC, and CMS Burley 21 SRC; wherein representative sample seeds of said Banket A1 SRC, CMS Banket A1 SRC, NC 2000 SRC, CMS NC 2000 SRC, NC 2002 SRC, CMS NC 2002 SRC, Burley 21 SRC, and CMS Burley 21 SRC have been deposited at the ATCC with the following ATCC Accession Nos.: PTA-121043 for Banket A1 SRC, PTA-121054 for CMS Banket A1 SRC, PTA-121053 for NC 2000 SRC, PTA-121045 for CMS NC 2000 SRC, PTA-121058 for NC 2002 SRC, PTA-121041 for CMS NC 2002 SRC, PTA-121059 for Burley 21 SRC, and PTA-121044 for CMS Burley 21 SRC.

12. A tobacco plant, or part thereof, produced from said seed of claim 11.

13. The part of the plant of claim 12, wherein said part is selected from the group consisting of a harvested leaf, a pollen, an ovule, an embryo, a cotyledon, a hypocotyl, a meristematic cell, a protoplast, a root, a root tip, a pistil, an anther, a flower, a shoot, a stem, a pod, a petiole, and combinations thereof.

14. A harvested leaf of said tobacco plant of claim 12.

15. The harvested leaf of claim 14, wherein said leaf has a reduced amount of nornicotine and/or N'-nitrosonornicotine (NNN).

16. The harvested leaf of claim 15, wherein said reduced amount of nornicotine and/or N-nitrosonomicotine (NNN) is reduced in a smoke stream produced from said leaf.

17. The cured tobacco material or a tobacco product of claim 1, wherein said cured tobacco material is from a tobacco plant, or part thereof, of said hybrid or said cultivar.

* * * * *

UNITED STATES PATENT AND TRADEMARK OFFICE
CERTIFICATE OF CORRECTION

PATENT NO. : 9,596,823 B2
APPLICATION NO. : 14/636876
DATED : March 21, 2017
INVENTOR(S) : Lewis et al.

Page 1 of 1

It is certified that error appears in the above-identified patent and that said Letters Patent is hereby corrected as shown below:

In the Specification

Column 62, Line 46: Insert a paragraph break between "SRC $F_1$ progeny plants." and "CMS NC 2000 SRC and CMS NC" so that it reads as follows:

-- SRC $F_1$ progeny plants.
    CMS NC 2000 SRC and CMS NC --

Column 67, Line 39: Delete "P381 S mutations." and insert -- P381S mutations. --

Column 89, Line 47: Delete "will be irrevocalbly removed," and insert -- will be irrevocably removed, --
    Line 48: Delete "by Application to meet all of" and insert -- by Applicant to meet all of --

In the Claims

Column 115, Claim 1, Line 30: delete "hybrid comprises" and insert -- progeny hybrid comprises --

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*